(12) United States Patent
Sixto, Jr. et al.

(10) Patent No.: US 6,966,919 B2
(45) Date of Patent: Nov. 22, 2005

(54) INSTRUMENT FOR APPLYING A SURGICAL FASTENER PARTICULARLY FOR THE TRANSORAL TREATMENT OF GASTROESOPHAGEAL REFLUX DISEASE (GERD)

(75) Inventors: Robert Sixto, Jr., Miami, FL (US); Kevin W. Smith, Coral Gables, FL (US); Juergen A. Kortenbach, Miami Springs, FL (US); Michael Sean McBrayer, Miami, FL (US); Charles R. Slater, Fort Lauderdale, FL (US)

(73) Assignee: ID, LLC, Miami, FL (US)

( * ) Notice: Subject to any disclaimer, the term of this patent is extended or adjusted under 35 U.S.C. 154(b) by 0 days.

(21) Appl. No.: 10/252,069

(22) Filed: Sep. 20, 2002

(65) Prior Publication Data

US 2004/0059349 A1  Mar. 25, 2004

(51) Int. Cl.[7] ............................................. A61B 17/08
(52) U.S. Cl. ...................... 606/153; 606/139; 606/220
(58) Field of Search .................... 606/153, 205–207, 606/219, 220, 157; 227/175.1

(56) References Cited

U.S. PATENT DOCUMENTS

| | | |
|---|---|---|
| 65,407 A | 6/1867 | Lusk, Jr. |
| 2,108,206 A | 2/1938 | Meeker |
| 3,551,987 A | 1/1971 | Wilkinson |
| 3,814,104 A | 6/1974 | Irnich et al. |
| 4,060,897 A | 12/1977 | Greenstein |
| 4,416,267 A | 11/1983 | Garren et al. |
| 5,037,433 A | 8/1991 | Wilk |
| 5,088,979 A | 2/1992 | Filipi et al. |
| 5,222,963 A | 6/1993 | Brinkerhoff et al. |
| 5,254,126 A | 10/1993 | Filipi et al. |
| 5,346,504 A | 9/1994 | Ortiz et al. |
| 5,395,030 A | 3/1995 | Kuramoto et al. |
| 5,403,326 A | 4/1995 | Harrison et al. |
| 5,433,721 A | 7/1995 | Hooven et al. |
| 5,465,894 A * | 11/1995 | Clark et al. .............. 227/175.1 |
| 5,558,665 A | 9/1996 | Kieturakis |
| 5,571,116 A | 11/1996 | Bolanos et al. |
| 5,573,496 A | 11/1996 | McPherson et al. |
| 5,676,674 A | 10/1997 | Bolanos et al. |

(Continued)

FOREIGN PATENT DOCUMENTS

EP    0480428 A2    4/1992

(Continued)

OTHER PUBLICATIONS

L. K. Nathanson et al.: "Laparoscopic ligamentum teres (round ligament) cardiopexy", Br. J. Surg. 1991, vol. 78, Aug., pp. 947-951.

(Continued)

*Primary Examiner*—Julian W. Woo
(74) *Attorney, Agent, or Firm*—Gregory L. Mayback

(57) ABSTRACT

A surgical instrument includes an end effector having a clevis and first and second jaws mutually rotatable between open and closed positions. The jaws are proximally directed and laterally displaced relative to a longitudinal axis of a control shaft of the instrument. The jaws hold first and second parts of a fastener, respectively. The first part includes a base having upstanding tissue piercing posts, and the second part includes another base defining apertures for receiving the posts, as well as a portion movable relative to the second base. When the upstanding posts are inserted into the apertures, the movable portion can be moved into a second configuration to lock the parts of the fastener together. The instrument is adapted to move the second part into the second configuration. A method for using the apparatus and fastener are also provided.

43 Claims, 41 Drawing Sheets

U.S. PATENT DOCUMENTS

| | | |
|---|---|---|
| 5,787,897 A | 8/1998 | Kieturakis |
| 5,792,153 A | 8/1998 | Swain et al. |
| 5,810,882 A | 9/1998 | Bolduc et al. |
| 5,868,141 A | 2/1999 | Ellias |
| 5,887,594 A | 3/1999 | LoCicero, III |
| 5,897,562 A | 4/1999 | Bolanos et al. |
| 5,901,895 A | 5/1999 | Heaton et al. |
| 5,984,932 A | 11/1999 | Yoon |
| 6,009,877 A | 1/2000 | Edwards |
| 6,067,990 A | 5/2000 | Kieturakis |
| 6,086,600 A | 7/2000 | Kortenbach |
| 6,113,609 A | 9/2000 | Adams |
| 6,139,563 A * | 10/2000 | Cosgrove et al. ........... 606/205 |
| 6,206,897 B1 | 3/2001 | Jamiolkowski et al. |
| 6,312,437 B1 | 11/2001 | Kortenbach |
| 6,325,503 B1 | 12/2001 | McCue, Jr. et al. |
| 6,387,104 B1 | 5/2002 | Pugsley, Jr. et al. |
| 6,461,366 B1 | 10/2002 | Seguin |
| 6,663,639 B1 | 12/2003 | Laufer et al. |
| 6,663,640 B2 | 12/2003 | Kortenbach |
| 6,669,713 B2 | 12/2003 | Adams |
| 6,736,828 B1 | 5/2004 | Adams et al. |
| 6,821,285 B2 | 11/2004 | Laufer et al. |
| 2001/0049469 A1 | 12/2001 | Kortenbach |
| 2002/0035370 A1 | 3/2002 | Kortenbach |
| 2002/0040226 A1 | 4/2002 | Laufer et al. |
| 2002/0193816 A1 | 12/2002 | Laufer et al. |
| 2003/0055442 A1 * | 3/2003 | Laufer et al. |
| 2003/0065340 A1 | 4/2003 | Geitz |
| 2003/0120285 A1 | 6/2003 | Kortenbach |
| 2003/0208211 A1 | 11/2003 | Kortenbach |
| 2003/0236536 A1 | 12/2003 | Grigoryants et al. |
| 2004/0010271 A1 | 1/2004 | Kortenbach |
| 2004/0087976 A1 | 5/2004 | DeVries et al. |
| 2004/0097986 A1 | 5/2004 | Adams |
| 2004/0158264 A1 | 8/2004 | Adams et al. |
| 2004/0162568 A1 | 8/2004 | Saadat et al. |
| 2004/0193117 A1 | 9/2004 | Laufer et al. |
| 2004/0193184 A1 | 9/2004 | Laufer et al. |
| 2004/0193193 A1 | 9/2004 | Laufer et al. |
| 2004/0193194 A1 | 9/2004 | Laufer et al. |
| 2004/0194790 A1 | 10/2004 | Laufer et al. |
| 2004/0225305 A1 | 11/2004 | Ewers et al. |

FOREIGN PATENT DOCUMENTS

| | | |
|---|---|---|
| EP | 0576265 A2 | 12/1993 |
| EP | 0646356 A2 | 4/1995 |
| EP | 1277442 A1 | 1/2003 |
| EP | 1 447 052 A2 | 8/2004 |
| EP | 1452 125 A2 | 9/2004 |
| FR | 2768324 | 3/1999 |
| GB | 2 128 478 A | 5/1984 |
| WO | 99/22649 | 5/1999 |
| WO | 02/24080 A2 | 3/2002 |
| WO | 02/094105 A2 | 11/2002 |
| WO | 2004/019788 A2 | 3/2004 |
| WO | 2004019787 A2 | 3/2004 |

OTHER PUBLICATIONS

Ronald A. Hinder et al.: "The Surgical Option for Gastroesophageal Reflux Disease", The American Journal of Medicine, vol. 103 (5A), Nov. 24, 1997, pp. 144S-148S.

Glyn G. Jamieson et al., "Laparoscopic Nissen Fundoplication", Ann. Surg., vol. 220, No. 2, 1994, B. Lippincott Company, pp. 137-145.

Alex G. Little: "Mechanisms of Action of Antireflux Surgery: Theory and Fact", World J. Surg., vol. 16, No. 2, Mar./Apr. 1992, pp. 320-325.

G.G. Jamieson: "Anti-reflux operations: how to they work?", Br. J. Surg. 1987, vol. 74, Mar., pp. 155-156.

Lucius D. Hill: "Myths of the esophagus", The Journal of Thoracic and Cardiovascular Surgery, vol. 98, No. 1, pp. 1-10.

D.I. Watson et al.: "Comparison of anterior, posterior and total fundoplication using a viscera model", International Society for Diseases of the Esophagus (1997) 10, pp. 110-114.

I.M.C. Janssen et al.: "Prospective randomized comparison of teres cardiopexy and Nissen fundoplication in the surgical therapy of gastro-oesophageal reflux disease", Br. J. Surg., 1993, vol. 80, Jul., pp. 875-878.

Karem Slim et al.: "Intraoperative Esophageal Manometry and Fundoplications: Prospective Study", World J. Surg. 20, 1996, pp. 55-59.

Paulo J.P.C. Carvalho et al.: "Endoscopic Sclerosis Prevents Experimental Reflux for Longer Than 12 Months: Reinforcement of the Gastric Component of the Reflux Barrier?", Thirty-first Annual University Surgical Resident' Conference, Feb. 10, 1989, Baltimore, Maryland, pp. 20-22.

T. Ismail et al.: "Yield pressure, anatomy of the cardia and gastro-oesophageal reflux", British Journal of Surgery 1995, 82, pp. 943-947.

Dominic J. Cirillo et al.: "Lipids and Pulmonary Function in the Third National Health and Nutrition Examination Survey", American Journal of Epidemiology, vol. 155, No. 9, 2002, pp. 842-848.

S.S. Kadirkamanathan et al.: "An ambulant porcine model of acid reflux used to evaluate endoscopic gastroplasty", Jan. 13, 1999, pp. 782-788.

T. Ismail et al.: "Yield Pressure: A New Concept in the Evaluation of Gerd?", AJG, vol. 91, No. 3, 1996, pp. 616-617.

R C M McGouran et al.: "Does measurement of yield pressure at the cardia during endoscopy provide information on the function of the lower oesophageal sphincter mechanism?", Gut, 1988, 29, pp. 275-278.

A. Cuschieri et al.: "Multicenter prospective evaluation of laparoscopic antireflux surgery", Surgical Endoscopy, Springer-Verlag, New York, 1993, pp. 505-510.

David B. Skinner et al.: "Surgical management of esophageal reflux and hiatus hernia", Journal of Thoracic and Cardiovascular Surgery, 1966, pp. 33-54.

Jorge A. Tocornali et al.: "A mucosol flap valve mechanism to prevent gastroesophageal reflux and esophagitis", Surgery, vol. 64, No. 2, Aug. 1968, pp. 519-523.

I. Boerema: "Hiatus hernia: Repair by right-sided, subhepatic, anterior gastopexy", Surgery, vol. 65, No. 6, Jun. 1969, pp. 884-893.

James R. Starling et al.: "Assessment of the Angelchik Prosthesis for Treatment of Symptomatic Esophageal Reflux", World Journal of Surgery, 11, 1987, pp. 350-355.

Gregory L. Falk et al.: "Laparoscopic Fundoplication: A Preliminary Report of the Technique and Postoperative Care", Aus. N.Z.J. Surg. 1992, No. 62, pp. 969-972.

M. Rampal et al.: "Traitment des hernies hiatales et du reflux oesophagien par la cardio-pexie avec le ligament rond du foie", Le Presse Medicale, Mar. 1967, pp. 617-619.

Peter J. Kahrilas: "Gastroesophageal Reflux Disease", JAMA, Sep. 25, 1996, vol. 276, No. 12, pp. 983-988.

R C M McGouran et al.: "Is yield pressure at the cardia increased by effective fundoplication?" Gut, 1989, 30, pp. 1309-1312.

Tom R. DeMeester et al.: "Nissen Fundoplication for Gastroesophageal Reflux Disease", Ann. Surg., vol. 204, No. 1, Jul. 1986, pp. 9-20.

Kent C. Westerbrook et al.: "Posterior Surgical Approaches to the Rectum", Ann. Surg., vol. 195, No. 6, Jun. 1982, pp. 677-685.

Hiram C. Polk et al.: "A Survey of Indications for Operation and Technic and Results of Fundoplication", Ann. Surg. vol. 173, No. 5, May 1971, pp. 775-781.

Glyn G. Jamieson: "Mechanisms of Gastro-Oesophageal Reflux", Aus. N.Z.J. Surg. 58, 1998, pp. 193-195.

Ismail T. Bancewicz et al.: "Yield Pressure: A New Concept in the Evaluation of Gerd?", AJG, vol. 91, No. 3, 1996, pp. 616-617.

J. T. Cramer et al.: "Mechanomyographic and electromyographic amplitude and frequency responses from the superficial quadriceps femoris muscles during maximal, eccentric isokinetic muscle actions", Electromyogr. Clin. Neurophysiol. 42, 2002, pp. 337-346.

Philip E. Donahue et al.: "Endoscopic Control of Gastro-Esophageal Reflux: Status Report", World J. Surg. 16, 1992, pp. 343-346.

Timothy H. Rupp et al.: "Endoscopic Antireflux Techniques", Experimental and Investigational Endoscopy, vol. 4, No. 2, Apr. 1994. pp. 353-364.

Lucius D. Hill: "Intraoperative measurement of lower esophageal sphincter pressure", The Journal of Thoracic and Cardiovascular Surgery, vol. 75, No. 3, Mar. 1978, pp. 378-382.

R.C.M. McGouran et al.: "A laser-induced scar at the cardia increases the yield pressure of the lower esophageal sphincter", Gastrointestinal Endoscopy, vol. 36, No. 5, 1990, pp. 439-443.

Ivan Cecconello et al.: "Esophagogastric Anastomosis with Valvuloplasty: An Experimental Study", Int. Surg. 1982, pp. 121-124.

J.B. McKernan: "Laparoscopic repair of gastroesophageal reflux disease", Surg Enodsc 8, Springer-Verlag, New York, 1994, pp. 851-856.

Kjell B. Å. Thor et al.: "Reappraisal of the Flap Valve Mechanism in the Gastroesophageal Junction", Acta Chir Scand 153, 1987, pp. 23-28.

J. Leigh Collis: "Surgical Control of Reflux in Hiatus Hernia", American Journal of Surgery, vol. 115, Apr. 1968, pp. 465-471.

Katherine W. O'Connor et al.: "An experimental endoscopic technique for reversing gastroesophageal reflux in dogs by injecting inert material in the distal esophagus", Gastrointestinal Endoscopy, vol. 30, No. 5, 1984, pp. 275-280.

P.J. Klingler et al.: "Laparoskopische Antirefluxverfahren", Chirug 69, 1998, pp. 148-157.

A Shafik: "Intraesophageal Polytef injection for the treatment of reflux esophagitis", Surg. Endos., 10, Springer Verlag, New York, 1996, pp. 329-331.

WJ Brown et al.: "Relationships between body mass index and well-being in young Australian women", International Journal of Obesity 24, 2000, pp. 1360-1368.

K.W. O'Connor et al.: "Endoscopic placement of collagen at the lower esophageal sphincter to inhibit gastroesophageal reflux: a pilot study of 10 medically intractable patients", Gastrointestinal Endoscopy, vol. 34, No. 2, 1988, pp. 106-112.

Pat Rich: "Simple GERD treatment offers new alternative", www.medicalpost.com, vol. 35, Issue 11, Mar. 16, 1999, pp. 1-2.

Stefan J.M. Kraemer et al. "Laparoscopic Hill repair", Gastrointestinal Endoscopy Online, vol. 40, No. 2, Mar./Apr. 1994, pp. 1-9.

Lucius D. Hill: "The Gastroesophageal Flap Valve", Journal of Clinical Gastroenterology, Apr. 28, 1999, pp. 194-197.

Rodney J. Mason et al.: "Nissen Fundoplication Prevents Shortening of the Sphincter During Gastric Distention", Archives of Surgery, vol. 132, Jul. 1997, pp. 719-724.

Sritharan S. Kadirkamanathan et al.: "Antireflux operations at flexible endoscopy using endoluminal stitching techniques: an experimental study", Gastrointestinal Endoscopy Online, vol. 44, No. 2, Aug. 1996, pp. 1-28.

Lucius D. Hill et al. "The gastroesophageal flap valve: in vitro and in vivo observations", Gastrointestinal Endoscopy, vol. 44, No. 5, Nov. 1996, pp. 1-12.

Russell W. Jennings et al.: "A Novel Endoscopic Transgastric Fundoplication Procedure for Gastroesophageal Reflux: An Initial Animal Evaluation", Journal of Laparoendoscopic Surgery, vol. 2, No. 5, 1992, pp. 207-213.

Rodney J. Mason et al.: "A new intraluminal antigastroesophageal reflux procedure in baboons", Gastrointestinal Endoscopy, vol. 45, No. 3, 1997, pp. 283-290.

PE Donahue et al.: "Floppy Dor fundoplication after esophagocardiomyotomy for achalasia", National Library of Medicine, Oct. 2002, discussion 722-3, pp. 1-2.

Lucius D. Hill et al.: "Surgery for Peptic Esophageal Stricture", The Esophagus: Medical and Surgical Management, 1988, WB Saunders Company, pp. 139-140.

R. Nissen: "Eine einfache Operation zur Beeinflussung der Refluxoesophagitis", Universitätsklinik Basel, pp. 590-529.

* cited by examiner

INSTRUMENT FOR APPLYING A SURGICAL FASTENER PARTICULARLY FOR THE TRANSORAL TREATMENT OF GASTROESOPHAGEAL REFLUX DISEASE (GERD)

BACKGROUND OF THE INVENTION

1. Field of the Invention

The invention relates to surgical fasteners, endoscopic surgical instruments, and procedures. More particularly, the invention relates to surgical fasteners, endoscopic instruments, and procedures for the transoral plication and fastening together of portions of the stomach for the treatment of GERD.

2. State of the Art

Gastroesophageal reflux disease (GERD) or persistent heartburn is caused by an improper relaxation of the lower esophageal sphincter (LES) that allows the frequent regurgitation of acidic stomach contents into the esophagus. If left untreated, chronic reflux may cause esophageal stricture, bleeding ulcers, perforation, and scarring. Continued reflux may lead to Barrett's esophagus, which involves changes in the cells that make up the esophagus and may lead to cancer.

The current mode of treatment is primarily pharmacological starting with antacids and progressing to proton pump inhibitors (PPIs). The progression of the disease is noted by the development of a hiatal hernia caused by the stomach being forced into the thoracic cavity. The pharmacological treatment ends with double and triple dosing of PPIs. At the point that the patient is not responding to the PPIs, surgical intervention is often recommended.

The current standard for surgery is the Nissen fundoplication. The fundoplication procedure involves wrapping the fundus of the stomach around the lower end of the esophagus and fastening it in place to make the lower esophageal sphincter (LES) less compliable. Traditionally, this procedure is accomplished via open surgery with the use of sutures to secure the plicated fundus of the stomach around the esophagus without penetrating (incising) the stomach. However, with the advent of laparoscopic surgery came the development of a corresponding laparoscopic Nissen procedure.

In an effort to further reduce the invasiveness of treatment for GERD, endoscopic techniques are being explored. Techniques that are currently under trials include the implantation of bulking agents, cautery techniques to produce scarring, and suturing or otherwise fastening internal tissue.

For example, U.S. Pat. No. 5,403,326 to Harrison et al. discloses a method of performing endoscopic fundoplication using surgical staples or two-part surgical fasteners. The procedure disclosed by Harrison et al. involves performing two percutaneous endoscopic gastrotomies (incisions through the skin into the stomach) and the installation of two ports through which a stapler, an endoscope, and an esophageal manipulator (invagination device) are inserted. Under view of the endoscope, the esophageal manipulator is used to pull the interior of the esophagus into the stomach. When the esophagus is in position, with the fundus of the stomach plicated, the stapler is moved into position around the lower end of the esophagus and the plicated fundus is stapled to the esophagus. The process is repeated at different axial and rotary positions until the desired fundoplication is achieved. While, the procedure disclosed by Harrison et al. is a vast improvement over open surgery, it is still relatively invasive requiring two incisions through the stomach.

U.S. Pat. No. 5,571,116 to Bolanos et al. discloses a non-invasive treatment of gastroesophageal reflux disease which utilizes a remotely operable invagination device and a remotely operable surgical stapler, both of which are inserted transorally through the esophagus. According to the methods disclosed by Bolanos et al., the invagination device is inserted first and is used to clamp the gastroesophageal junction. The device is then moved distally, pulling the clamped gastroesophageal junction into the stomach, thereby invaginating the junction and involuting the surrounding fundic wall. The stapler is then inserted transorally and delivered to the invaginated junction where it is used to staple the fundic wall.

Bolanos et al. disclose several different invagination devices and several different staplers. Generally, each of the staplers disclosed by Bolanos et al. has an elongate body and a spring biased anvil which is rotatable approximately 15 degrees away from the body in order to locate the invaginated gastroesophageal junction between the body and the anvil. The body contains a staple cartridge holding a plurality of staples, and a staple firing knife. Each of the invagination devices disclosed by Bolanos et al. has a jaw member which is rotatable by at least 45 degrees and in some cases more than 90 degrees to an open position for grasping the gastroesophageal junction. One of the chief disadvantages of the methods and apparatus disclosed by Bolanos et al. is that the stapler and the invagination device are separately inserted but must both be present in the esophagus at the same time. With some of the embodiments disclosed, the presence of both instruments is significantly challenged by the size of the esophagus. Moreover, the esophagus cannot form a seal about both the instruments and, thus, it is difficult to insufflate the stomach to facilitate the procedure. In addition, the actuating mechanism of the device disclosed by Bolanos et al. is awkward. In particular, the stapler anvil is biased to the open position, and it is not clear whether or not the stapler anvil can be locked in a closed position without continuously holding down a lever. In addition, it appears that the staple firing trigger can be inadvertently operated before the anvil is in the closed position. This would result in inadvertent ejection of staples into the stomach or the esophagus of the patient.

U.S. Pat. No. 6,086,600 to Kortenbach discloses an endoscopic surgical instrument adapted to perform fundoplication, between the stomach wall and the esophagus. The instrument includes a flexible tube, a grasping and fastening end effector coupled to the distal end of the tube, and a manual actuator coupled to the proximal end of the tube. The manual actuator is coupled to the end effector by a plurality of flexible cables which extend through the tube. The tube contains a lumen for receiving a manipulable endoscope and the end effector includes a passage for the distal end of the endoscope. The end effector has a store for a plurality of male fastener parts, a store for a plurality of female fastener parts, a rotatable grasper, a rotatable fastener head for aligning a female fastener part and a male fastener part with tissues therebetween, and a firing member for pressing a male fastener part through tissues grasped by the grasper and into a female fastener part. According to a stated preferred embodiment, the overall diameters of the flexible tube and the end effector (when rotated to the open position) do not exceed approximately 20 mm so that the instrument may be delivered transorally to the fundus of the stomach.

While transoral fundoplication devices and methods hold promise, it is still difficult to deliver and manipulate the necessary apparatus transorally. One reason for the difficulty is that the overall diameter, or more accurately the cross sectional area, of the equipment is too large. Moreover, even if the Kortenbach device could be reduced to 20 mm in diameter (314 mm$^2$ cross sectional area), it would still be difficult to manipulate. Those skilled in the art will appreciate that larger instruments are less pliable and the plication and fastening procedure requires that the instruments be retroflexed nearly 180 degrees. Moreover, it will be appreciated that large instruments obscure the endoscopic view of the surgical site.

Recently, PCT WO 00/78227 (NDO Surgical Inc.) has disclosed a device sized to receive an endoscope and which is purportedly capable of plicating and damaging portions of the stomach wall to effect serosa-to-serosa contact which results in stomach wall tissue adhesion. As a result, compliance of the tissue about the esophagus would be reduced and a flap (i.e., valve) would be formed about the LES. For this purpose, the plication and adhesion should preferably be created at the horseshoe-shaped tissue in the stomach surrounding the LES. The distance from the Z line (esophageal/stomach borderline) to the horseshoe-shaped target tissue is approximately 1 to 3 cm into the stomach and plication at this location permits the greatest stress to be placed on the tissue about the LES. In order to approach plication at this location the device has a particularly complicated and unwieldy multi-component end effector adapted to grab tissue, plicate the tissue, and fasten the tissue together. That is, while the above referenced device appears to offer a solution, it may not be practical to implement mechanically or operate during the procedure. Further, the above referenced device, while respectfully having a relatively smaller diameter than other prior art (approximately 18 mm in diameter and 254 mm$^2$ in cross-sectional area) maintains that cross-sectional area over its entire length. In addition to limited flexibility, the size of the device renders it difficult to traverse the tracheopharangeal passage. Moreover, while it is desirable to plicate the stomach wall in a direction parallel to the esophagus in order to satisfactorily reduce compliance of the tissue, it is noted that the end effector of the above referenced device is unable to approach the target tissue from the desired direction.

It is also preferable that any fastener used for the apposition of tissue in the stomach cavity be removable in the event of tissue ischemia, vagus nerve irritation, or continued reflux, and be relatively non-injurious to the patient should the fastener inadvertently become loose from the device or dislodged from the tissue. In addition, current fasteners are difficult to locate within the stomach via an endoscope if it becomes necessary to find the fastener for removal.

SUMMARY OF THE INVENTION

It is therefore an object of the invention to provide methods and apparatus for transoral plication and fastening of tissue of the stomach wall.

It is another object of the invention to provide an apparatus for transoral plication and fastening of tissue which is adapted to form a plication at a location substantially adjacent the lower esophageal sphincter (LES).

It is also an object of the invention to provide an apparatus for transoral plication and fastening of tissue which is adapted to approach the stomach tissue in a direction substantially parallel to the esophagus.

It is an additional object of the invention to provide an apparatus that has a relatively small cross-sectional area and is adapted for transoral plication and fastening of tissue.

It is a further object of the invention to provide an endoscopic apparatus for transoral plication and fastening of tissue which can be detached from the endoscope while the endoscope is located within the stomach.

It is a further object of the invention to provide methods and apparatus for transoral plication and fastening of tissue which damages tissue such that adhesion occurs during healing.

It is still another object of the invention to provide a tissue fastener which will not cause ischemia and which, if necessary, is relatively easily endoscopically removable from the stomach.

It is still a further object of the invention to provide a fastener which, if inadvertently released into the stomach, will not cause harm to the gastrointestinal tract.

It is yet another object of the invention to provide a fastener which can easily be identified in the stomach with an endoscope.

In accord with these objects which will be discussed in detail below, a two-part fastener, and an instrument and system for application of the fastener to the stomach wall in a manner which effectively treats gastroesophageal reflux disease (GERD) are provided.

The fastener includes male and female parts which can be adjustably coupled together to define various spaces therebetween such that depending on the amount of tissue between the components a desired amount of force can be applied to the tissue therebetween by the fastener, i.e., such that the tissue does not necrose. The male part includes a plurality of tissue-piercing posts which are spring-biased to collapse into a base of the male part to prevent injury to the patient should the male part inadvertently become separated from its respective jaw prior to coupling with the female part or separated from the female part after coupling therewith. In addition, the female part is provided with a cover which shields the piercing tips of the posts after the male and female parts are coupled together. The fastener when in a fastened configuration may be unfastened by moving portions of the cover relative to each other. This can be performed, e.g., using a snare device to lasso the device and moves portions of the female part relative to each other.

The instrument includes a relatively short distal end effector which may be coupled over a portion of the endoscope, a proximal actuation handle, and a relatively small diameter control shaft extending between the handle and the end effector. As only the control shaft extends from the handle of the instrument to the end effector, during use, the cross-sectional area of the system within the esophagus at all locations other than the distal end of the instrument, is substantially small (the sum of the areas of the endoscope and the control shaft); i.e., less than half that of other proposed systems. In addition, at the distal end of the instrument, the system cross-sectional area is also smaller than that of prior art systems.

More particularly, the distal end effector may be provided with a sleeve that can be slidably positioned over the end of the endoscope and likewise slidably removed therefrom. The sleeve is preferably proximally and distally tapered to ease insertion into and removal from the esophagus. The distal end effector also includes a clevis about which a pair of rotatable jaws are coupled. The jaws are laterally displaced relative to the control shaft. The jaws are each adapted to each hold one part of the two-part fastener. When the jaws are in a closed position with the parts of the fastener located therebetween, the jaws extend substantially parallel to the longitudinal axis of the control shaft. That is, the jaw assembly is fixed in a retroflexed or "looking back" arrangement, directed 180° from the distal end of the control shaft.

In addition, the jaws and fastener parts together define posts adapted to grab the stomach tissue, pierce and damage the serosa of the stomach tissue, and plicate the stomach tissue when the jaws are moved from an open position to a closed position.

The instrument includes a first control element that moves the jaws between open and closed positions, and a second control element that couples the fastener parts together and releases the fastener parts from the jaws.

One embodiment of using the system includes sliding the sleeve of the instrument over the distal end of the endoscope and moving the sleeve to a central location on the scope. The endoscope is next inserted through the tracheoesophageal passage and into the stomach. The distal end of the instrument, with the jaws in a closed low profile configuration, is then slid over the endoscope, through the tracheoesophageal passage, into the stomach, and off the distal end of the endoscope. The endoscope may be retroflexed during a portion of the insertion of the distal end of the instrument such that the instrument insertion is performed under view of the endoscope.

The jaws of the instrument are then opened by actuation of the handle, and the handle and/or control shaft are pulled back to cause the open jaws to forcibly contact the stomach tissue surrounding the lower esophageal sphincter; i.e., the target tissue 1 cm to 3 cm into the stomach. As the jaws contact the tissue, a post on the female jaw and the posts of the male part of the fastener pierce the mucosa, deep muscle and/or serosa of the tissue. An endoscopic grasping instrument extending through the endoscope may be used in conjunction with the end effector to aid in pulling the target tissue between the jaws. The handle is then actuated to cause the jaws to move into a closed position, pulling into apposition two portions of the tissue to form a plication. The posts of the male part of the fastener extend through both layers of tissue at the ends of the plication and enter corresponding openings in the female part as the jaws are closed and the fastener is clamped, but not locked, about the tissue. If desired, the jaws can then be opened to apply a different clamping pressure to the tissue or entirely relocate the fastener. Once the fastener is in a desired location and with a desired pressure on the tissue, the handle is actuated to lock the fastener and release the fastener from the jaws. The instrument may then be recoupled to the endoscope, and the endoscope and the instrument may be withdrawn from the patient.

Other instruments and methodologies which provide other couplings between the instrument and the endoscope, and which do not require any coupling of the instrument to the endoscope are also provided.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
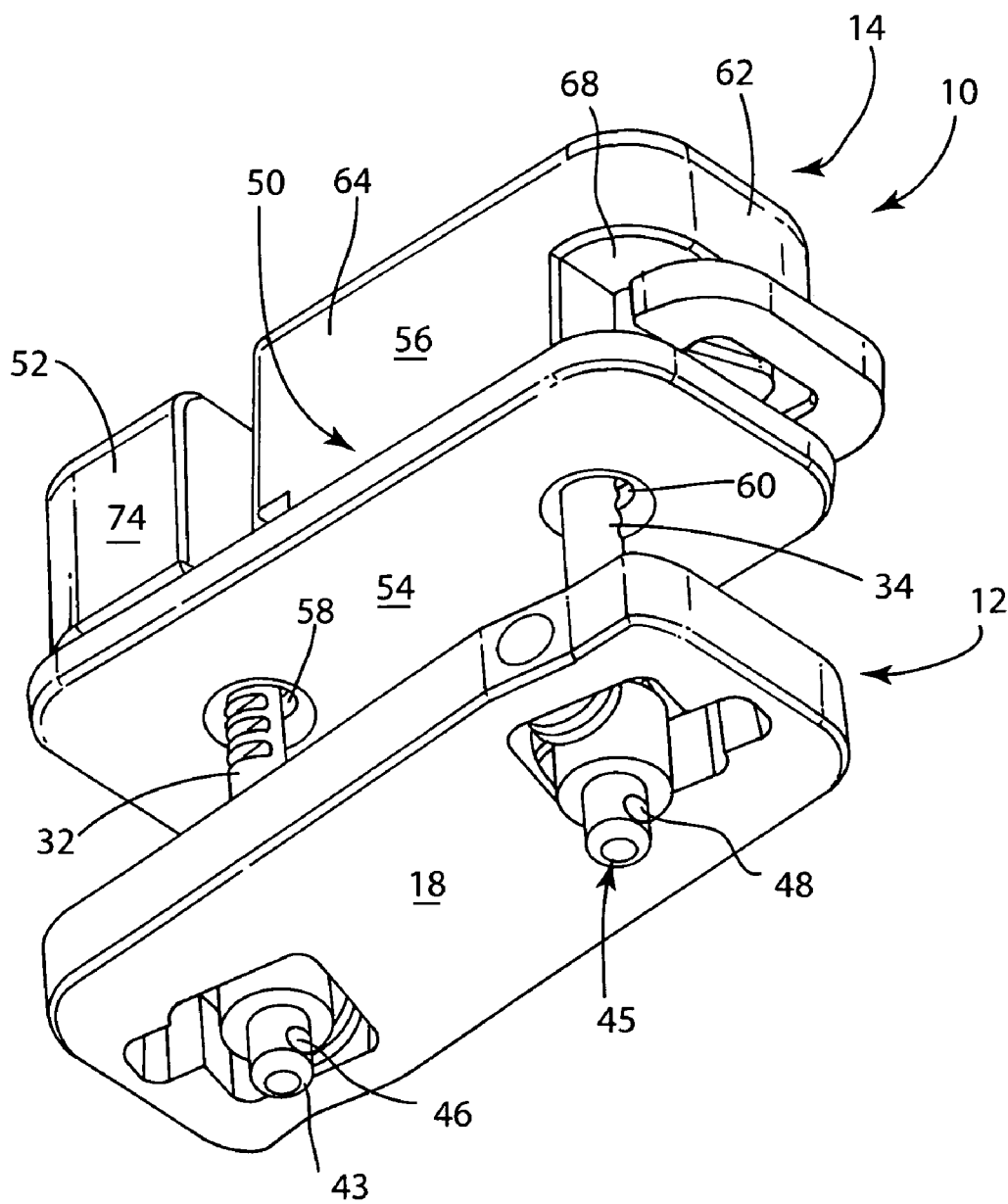
FIG. 1 is a bottom perspective view of a two-part tissue fastener with male and female parts thereof shown mated but in an unlocked configuration.
Figure 2:
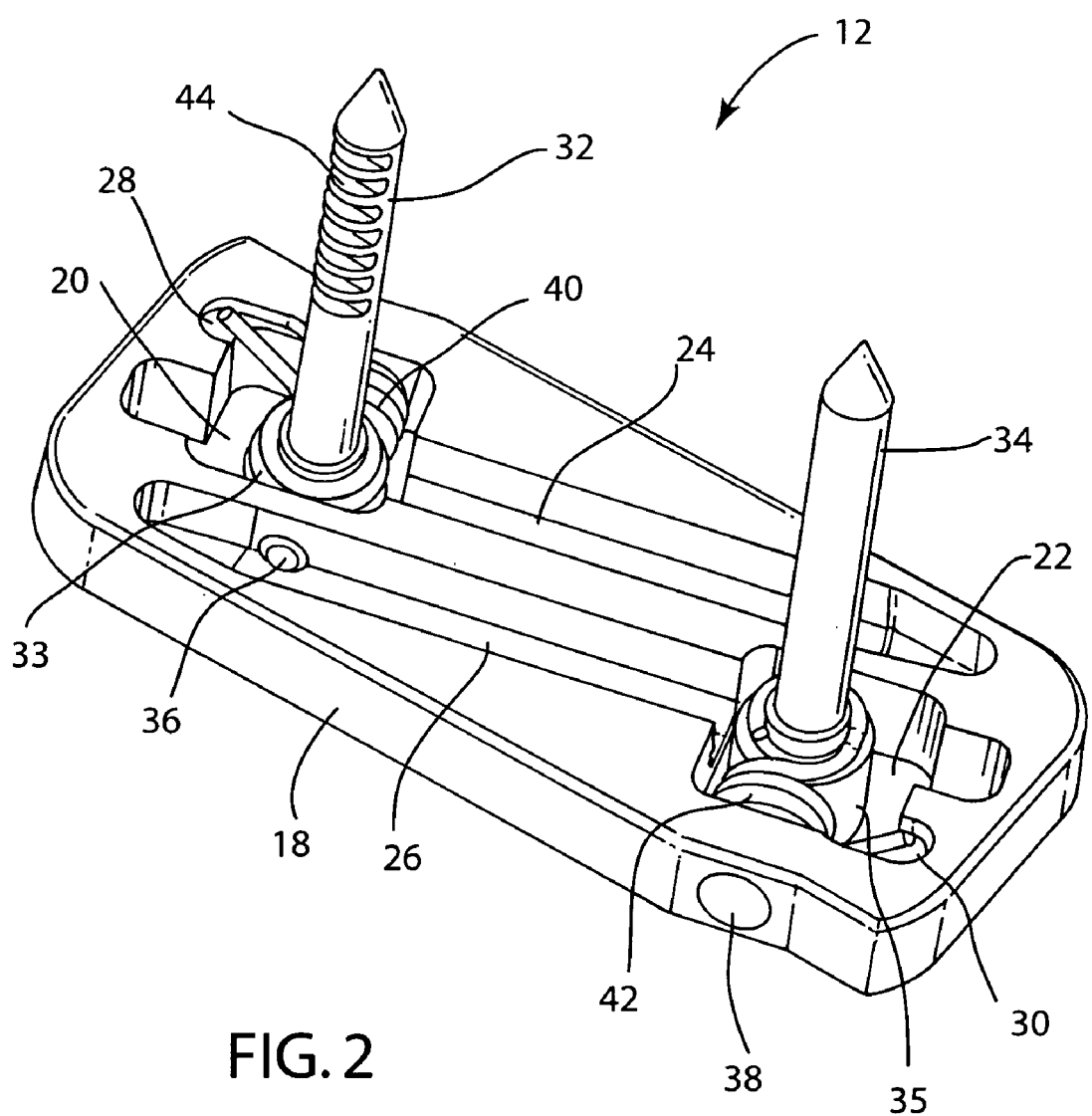
FIG. 2 is a perspective view of a male part of the two-part fastener of FIG. 1, shown with posts of the male part in an upright configuration.
Figure 3:
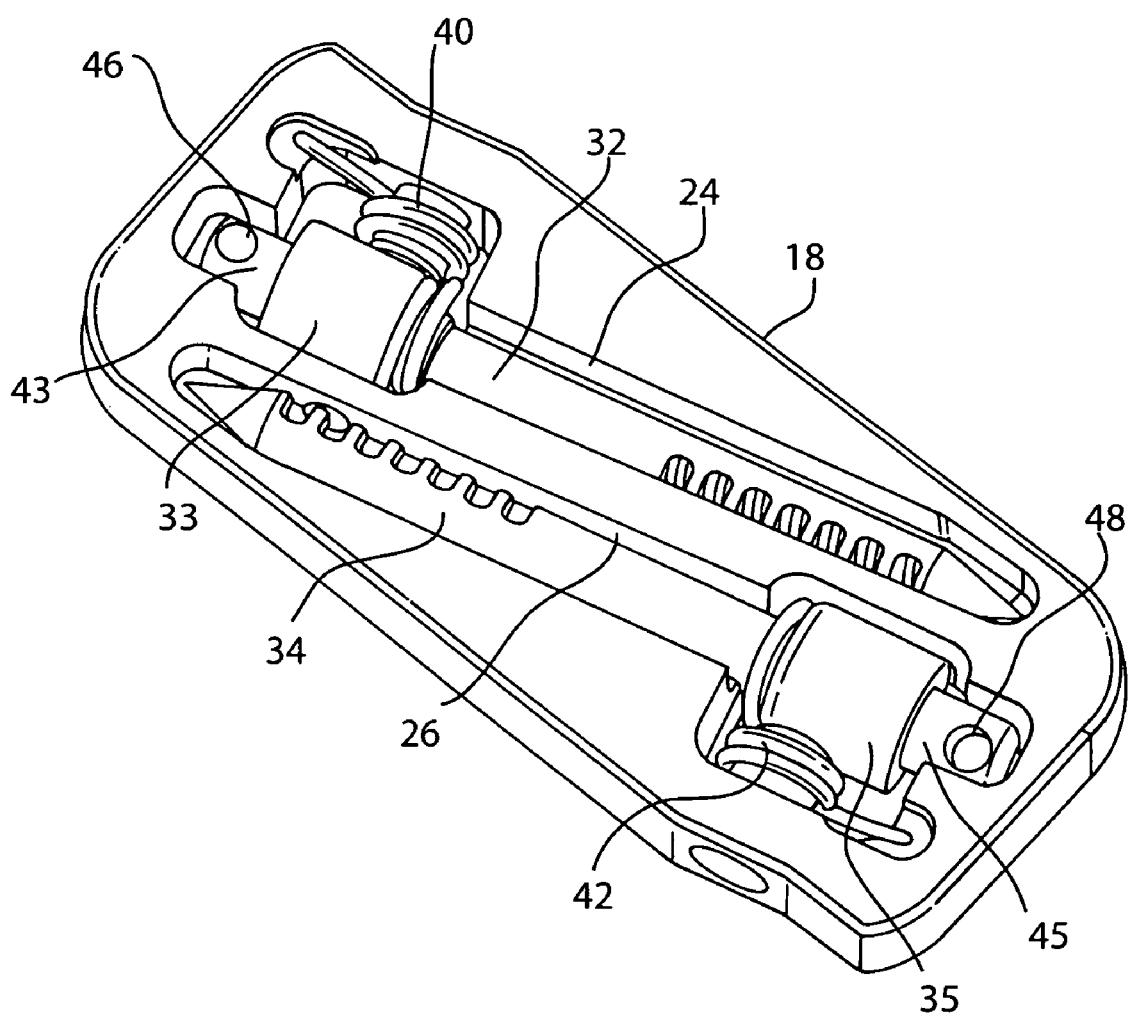
FIG. 3 is a perspective view of a male part of the two-part fastener, similar to FIG. 2, shown with posts of the male part in a collapsed configuration.

Turning now to FIG. 1, a two-part fastener 10 according to the invention is shown. The fastener 10 includes male and female parts 12, 14. Referring to FIGS. 1 and 2, the male part 12 includes a base 18 defining two openings 20, 22 therethrough and, in one side, two elongate channels 24, 26 and two spring shelves 28, 30. Two tissue-piercing posts 32, 34 are rotatably coupled to the base 18 in alignment with the channels 24, 26. Each posts includes an enlarged portion 33, 35 having a diametric bore (not shown). Axles 36, 38 extend across openings 20, 22, through the bores, and are press-fit into the base 18 such that the posts 32, 34 are rotatable thereabout. The posts 32, 34 have a length of preferably at least 2 mm such that they are adapted to penetrate the serosa of the stomach tissue, and a diameter of preferably less than 1.5 mm inch so that the holes made thereby in the stomach tissue are not prone to leakage. Furthermore, while the posts 32, 34 are adapted to pierce tissue, they are also slightly rounded at the tips so as to preferably only displace tissue rather than cut tissue. Torsion springs 40, 42 are coupled to the posts 32, 34 and are stopped against the base 18 at the shelves 28, 30. Referring to FIGS. 1 through 3, the torsion springs 40, 42 operate to bias the posts 32, 34 toward a collapsed configuration in which the posts lie within the channels 24, 26. The channels 24, 26 are oriented at an angle within the base 18 to accommodate posts 32, 34 of a maximized length for the size of the base 18. An upper portion of each post 32, 34 is provided with a plurality of slots (notches or grooves) 44 along a medial side thereof, and a lower end 43, 45 of each post is provided with a diametric bore 46, 48.

Figure 4:
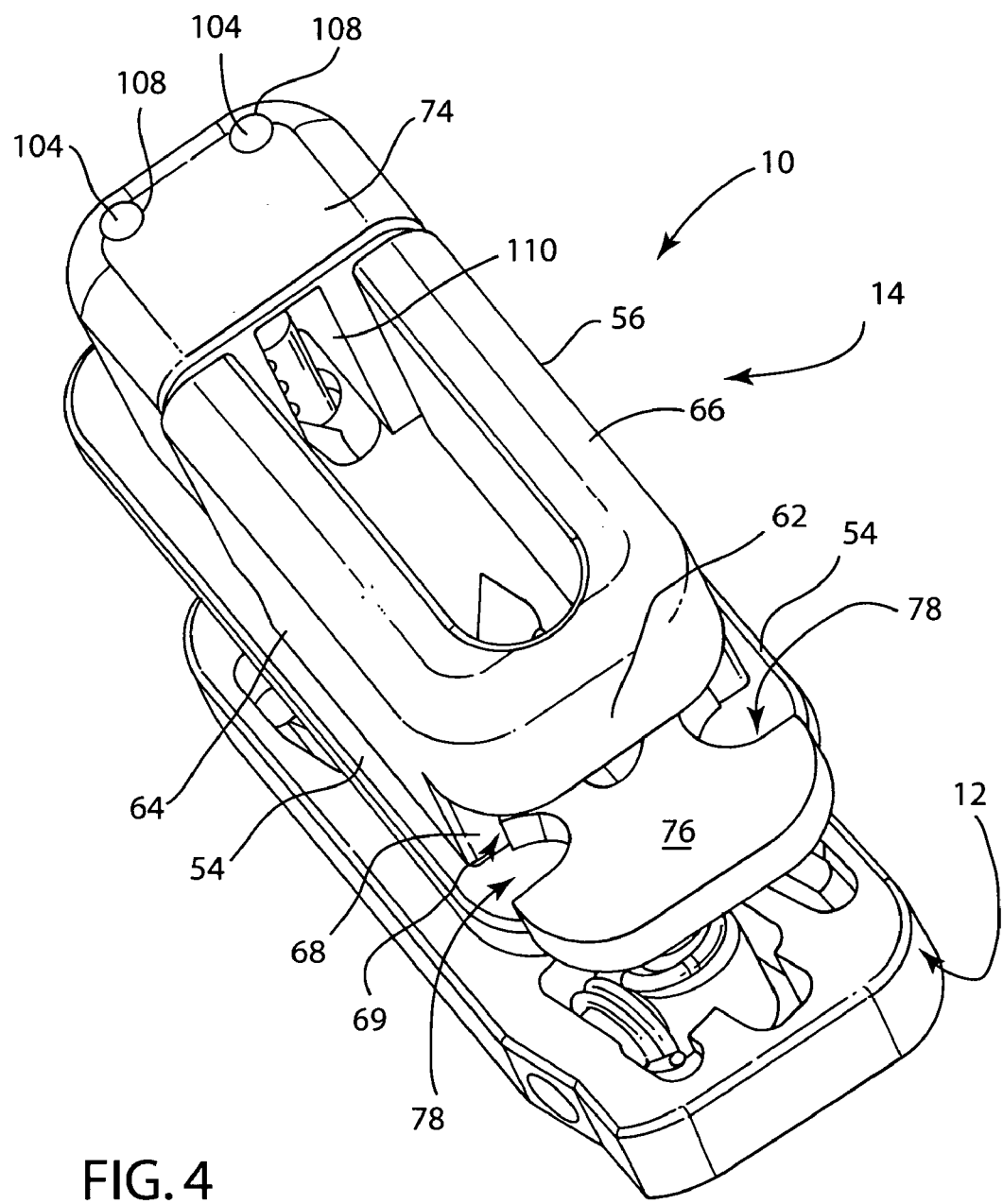
FIG. 4 is a top perspective view of the two-part tissue fastener in the same configuration as FIG. 1.
Figure 5:
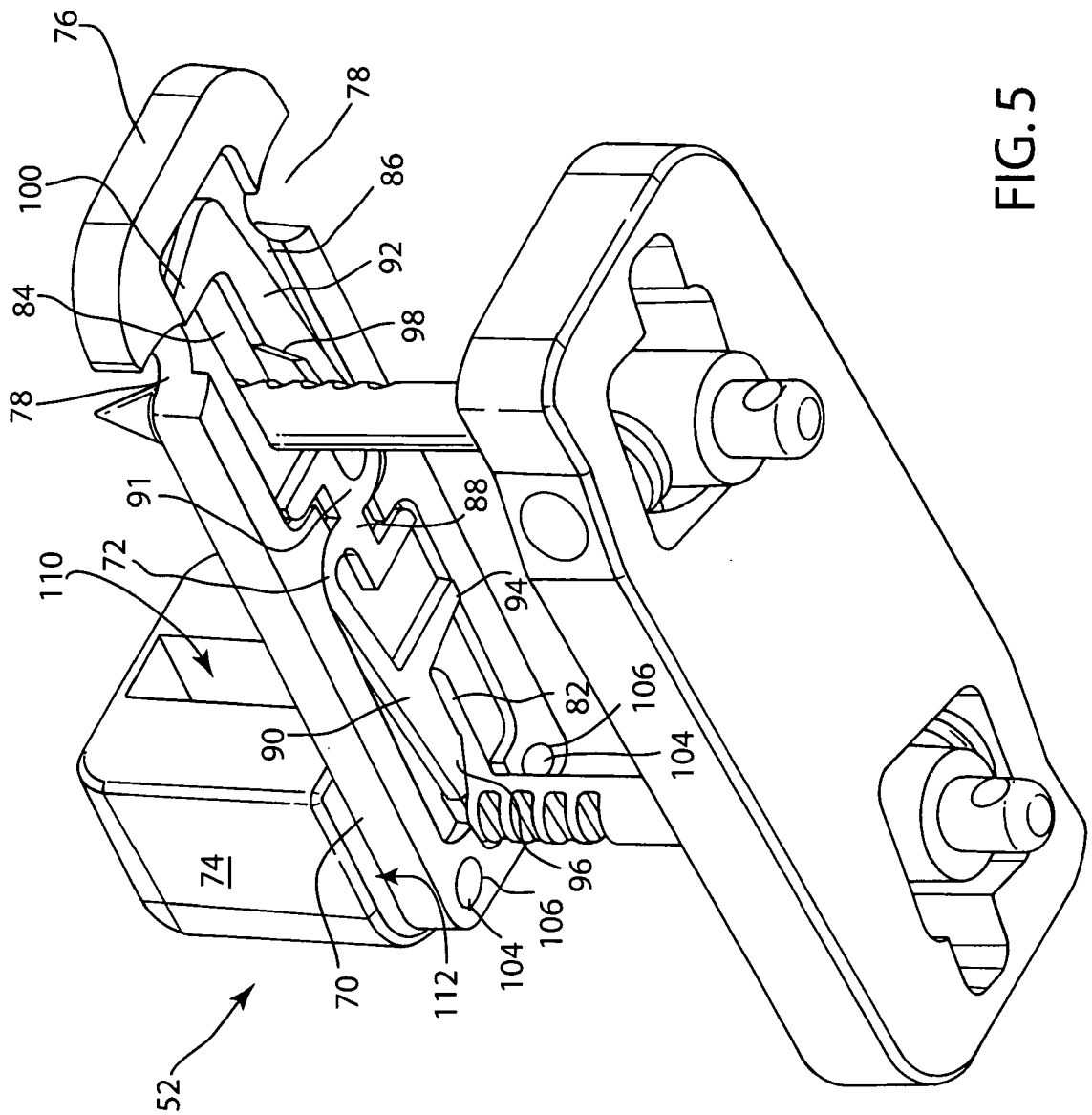
FIG. 5 is a bottom perspective view of the two-part tissue fastener in the same configuration as FIG. 1, shown with the latch body removed from the female part of the fastener to facilitate viewing the interior structure of the female part of the fastener.

Referring to FIGS. 1, 4 and 5, the female part 14 includes a latch body 50 and a sliding assembly 52 which is slidably movable relative to the latch body. Referring particularly to FIG. 1, the latch body 50 includes a base portion 54 and a cover (or shield) portion 56 which are manufactured as a single unit or a fixed assembly of separate elements. The base portion 54 includes two holes 58, 60, each sized to receive a post 32, 34 therethrough and preferably having chamfered openings. The cover portion 56 is preferably U-shaped, having an end portion 62 and two sides 64, 66 that extend around a portion of the periphery of the base portion 54. The end portion 62 of the cover portion 56 defines a lower recess 68 and opening 69 at the recess 68.

The sliding assembly 52 includes a latch slide 70, a latch lock 72, and a slide cover (or shield) 74. Referring particularly to FIG. 5, the latch slide 70 defines two elongate slots 82, 84, a lower recess 86, a head portion 76 having a relatively larger width than the remainder of the slide, and cutouts 78 between the head portion 76 and the remainder of the slide. The latch lock 72 resides in recess 86 and the recess is shaped to stably hold a central portion 88 of the lock 72 and to provide space for lateral displacement of elongate portions of the lock 72. More particularly, the lock 72 includes a generally Z-shaped central portion 88, and two arms 90, 92 extending from a central extension 91 of the central portion 88. Arm 90 includes a central laterally extending stop 94 and, at its terminus, a beveled catch 96. Arm 92 includes a central beveled catch 98, and at its terminus, a laterally extending stop 100. Each arm 90, 92 is biased in the direction of the extension of its stop 94, 100, with the bevel of its catch 96, 98 directed toward a respective slot 82, 84. The latch slide 70, with latch lock 72 positioned therein, is slidably inserted through the opening 69 of the cover portion 56 of the latch body 50, and the slide cover 74 is then fixed onto the latch slide 70 with pins 104 that are press fit into respective coupling holes 106, 108 (FIGS. 4 and 5). It is appreciated that the latch lock 72 is retained in the recess 86 by the base portion 54 of the latch body 50. The slide cover 74 defines a central space 110. In addition, referring to FIG. 5, the latch slide 70 and slide cover 74 define a setback 112 at which the female part 14 can be engaged with an applicator instrument 200 (FIG. 9), as described further below.

By way of example only, preferred dimensions for one exemplar fastener sized for being passed through the esophagus and coupling portions of the stomach tissue together are as follows. The male part 12 has a length of 15 mm, a width of 6.25 mm, and a height of 2 mm (excluding the posts). The female part 14 has a length of 15 mm, a width of 6.25 mm, and a height of 4 mm. The coupled fastener 10 has overall dimensions of a length of 15 mm, a width of 6.25 mm, and a height of 6 mm plus the thickness of the tissue between the male and female parts.

The parts 12, 14 are preferably constructed of titanium or titanium alloy, and then anodized according to processes known in the art of metallurgy to impart to the parts a color distinct from the natural tissue of the stomach cavity. Preferred colors include purple, blue and black.

As discussed in more detail below, when the male and female parts 12, 14 of the fastener 10 are brought into apposition on opposite sides of tissue located therebetween by the below described instrument 200 (FIG. 9) (with the posts 32, 34 of the male part 12 held upright against the bias of the torsion springs 40, 42, as detailed below), the posts 32, 34 of the male part 12 can pierce through tissue and extend into the holes 58, 60 of the base portion 54 of the female part 14 (FIG. 1). The chamfered openings of the holes 58, 60 facilitate this mating by guiding the posts into the holes 58, 60 even if the parts 12, 14 are slightly misaligned. The male and female parts 12, 14 of the fastener 10 are then clamped about the tissue. The slide cover 74 and cover portion 56 shield the sharp portions of posts 32, 34, respectively, which extend through the base portion 54 of the female part 14.

Figure 6:
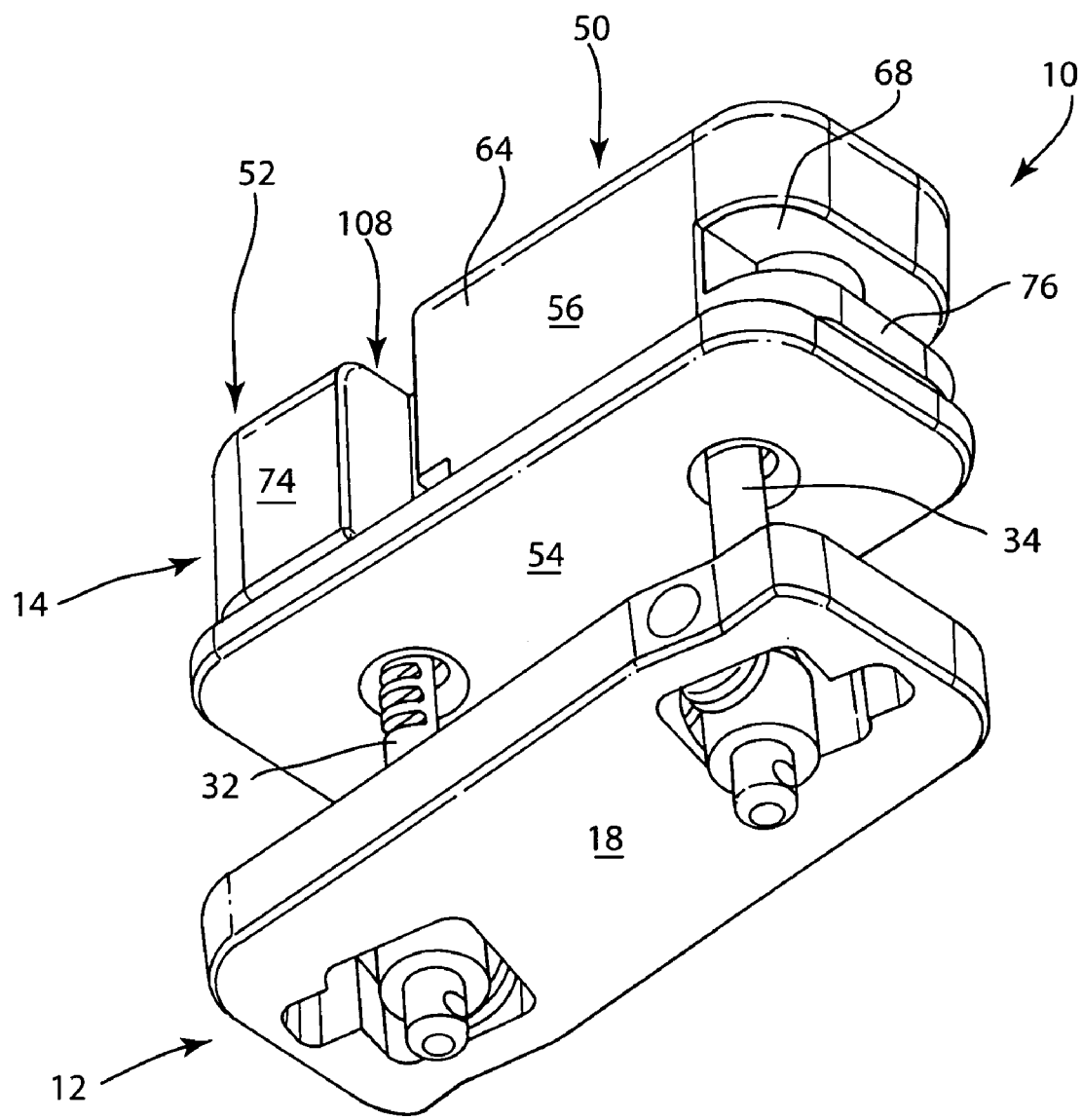
FIG. 6 is a bottom perspective view of a two-part tissue fastener with male and female parts thereof shown mated and in a locked configuration.
Figure 7:
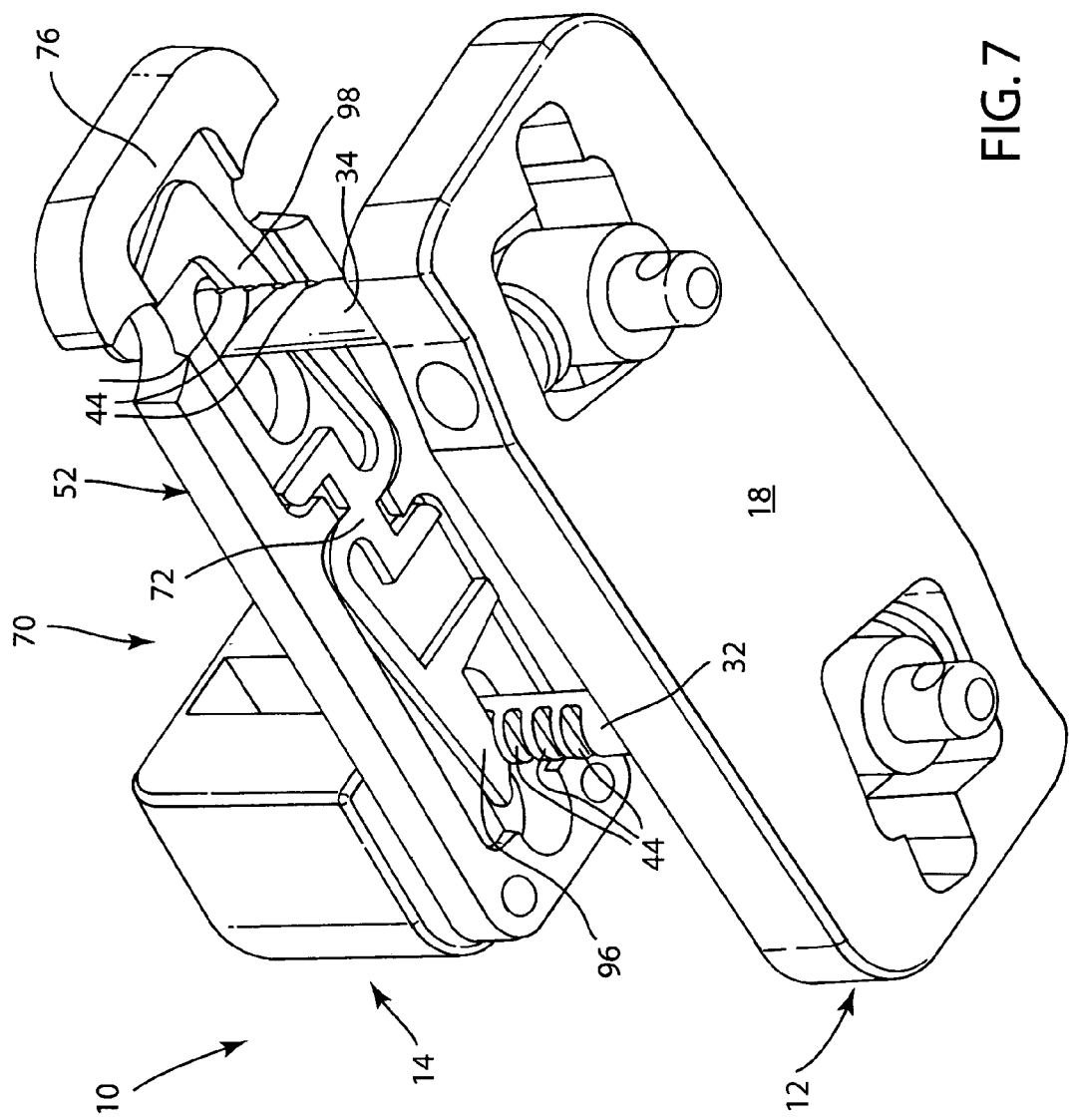
FIG. 7 is a bottom perspective view of the two-part tissue fastener in the same configuration as FIG. 6, shown with the latch body removed from the female part of the fastener to facilitate viewing the configuration of the interior structure of the female part of the fastener.

Referring now to FIGS. 6 and 7, once the fastener 10 is clamped about tissue with a desired clamping force (or desired pressure), the sliding assembly 52 is longitudinally slidable relative to the latch body 50 until the head 76 of the latch slide 70 abuts the cover portion 56 within the recess 68 and until the catches 96, 98 on the latch lock 72 ride against their bias into respective slots 44 of the posts 32, 34, thereby locking the male and female parts 12, 14 together. The plurality of slots 44 and the substantial length of the posts 32, 34 permits the base 18 of the male part 12 and base portion 54 of the female part 12, 14 to be coupled at several distances relative to each other. In addition, the base 18 and base portion 54 may even be skewed relative to each other to further accommodate various configurations of tissue therebetween, with the catches 96, 98 entering, for example, a third notch of post 32 and a fourth notch of post 34. As a result of this adjustability, a desired amount of force can be applied to tissue between the parts 12, 14, whether or not the tissue therebetween is of uniform thickness, and with such force preferably limited to prevent tissue necrosis.

Furthermore, it is noted that when the sliding assembly 52 is moved relative to the latch body 50, the catches 96, 98 will automatically find an appropriate slot 44, as the latch lock 72 is spring-loaded and compliant. That is, should a catch 96, 98 of the latch lock 72 initially contact a post 32, 34 at a non-slotted location, the compliance of the latch lock 72 will cause the catch 32, 34 to snap into an adjacent slot 44 when subject to small additional movement.

It is also noted that the movement of the sliding assembly 52 relative to the latch body 50 causes the slide cover 74 to be spaced apart from the latch body cover 56. This opens a space 108 between the slide cover 74 and the latch body cover 56.

Even after the male and female parts 12, 14 have been locked together, they may be unlocked from each other. Moving the sliding assembly 52 in an opposite direction relative to latch body 54, such that the slide cover 74 and cover portion 56 are moved relatively closer together, operates to unlock the male and female parts 12, 14 such that they may then be separated from each other. That is, this mechanism facilitates decoupling of a fastener and thereby permits atraumatic retrieval of an implanted fastener. One manner of effecting the decoupling can be performed with a standard endoscopic snare device. A loop of the snare device is provided over and about the slide cover 74 and cover portion 56 and the two parts are pulled toward each other by decreasing the size of the snare loop. A portion of the snare loop may be positioned through recess 68 to prevent the loop from slipping off the fastener 10. Moreover, it is noted that the unnatural color of the fastener 10 relative to the tissue of the stomach cavity facilitates endoscopically locating an implanted fastener for such retrieval.

As discussed above, the posts 32, 34 are spring-biased to collapse into a base of the male component when not retained against the bias. This operates to prevent injury to the patient should the male part 12 inadvertently become separated from the applicator instrument 200 or from the female part 14 after coupling therewith. Given the size of the parts and the protection of sharps from exposure to the body, the parts may be safely passed through the gastrointestinal system.

Figure 8:
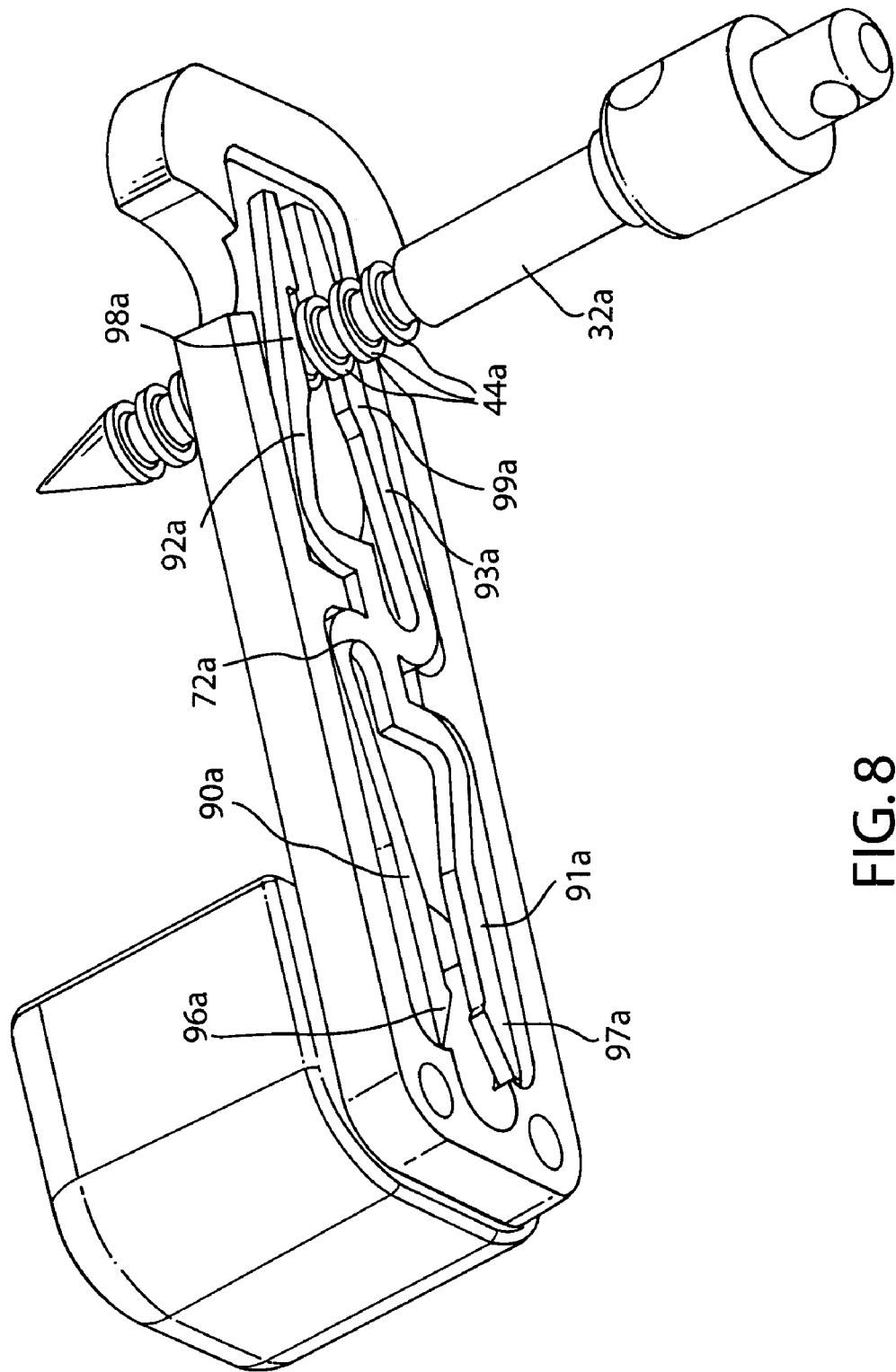
FIG. 8 is a perspective view of an alternate post of a male part of the fastener and an alternate sliding assembly of a female part of the fastener.

It is recognized that various other configurations for locking the latch lock 72 of the female part 14 relative to the posts 32, 34 of the male part 12 can be used. For example, referring to FIG. 8, the posts 32a may be provided with circumferential grooves 44a. And the latch lock 72a may have another configuration which effectively provides a catch which can be locked within the grooves 44a. In FIG. 8, the latch lock 72a includes, for post 32a, two resilient, spaced-apart, spring-biased arms 92a, 93a each with a catch 98a, 99a adapted to engage within a groove on the post 32a and, for the second post (not shown), two resilient, spaced-apart, spring-biased arms 90a, 91a each with a catch 96a, 97a adapted to engage within a groove on the post.

As further discussed below and clearly shown in the figures relating thereto, the parts 12, 14 of the fastener 10 are delivered through the esophagus in a lengthwise orientation.

Figure 9:
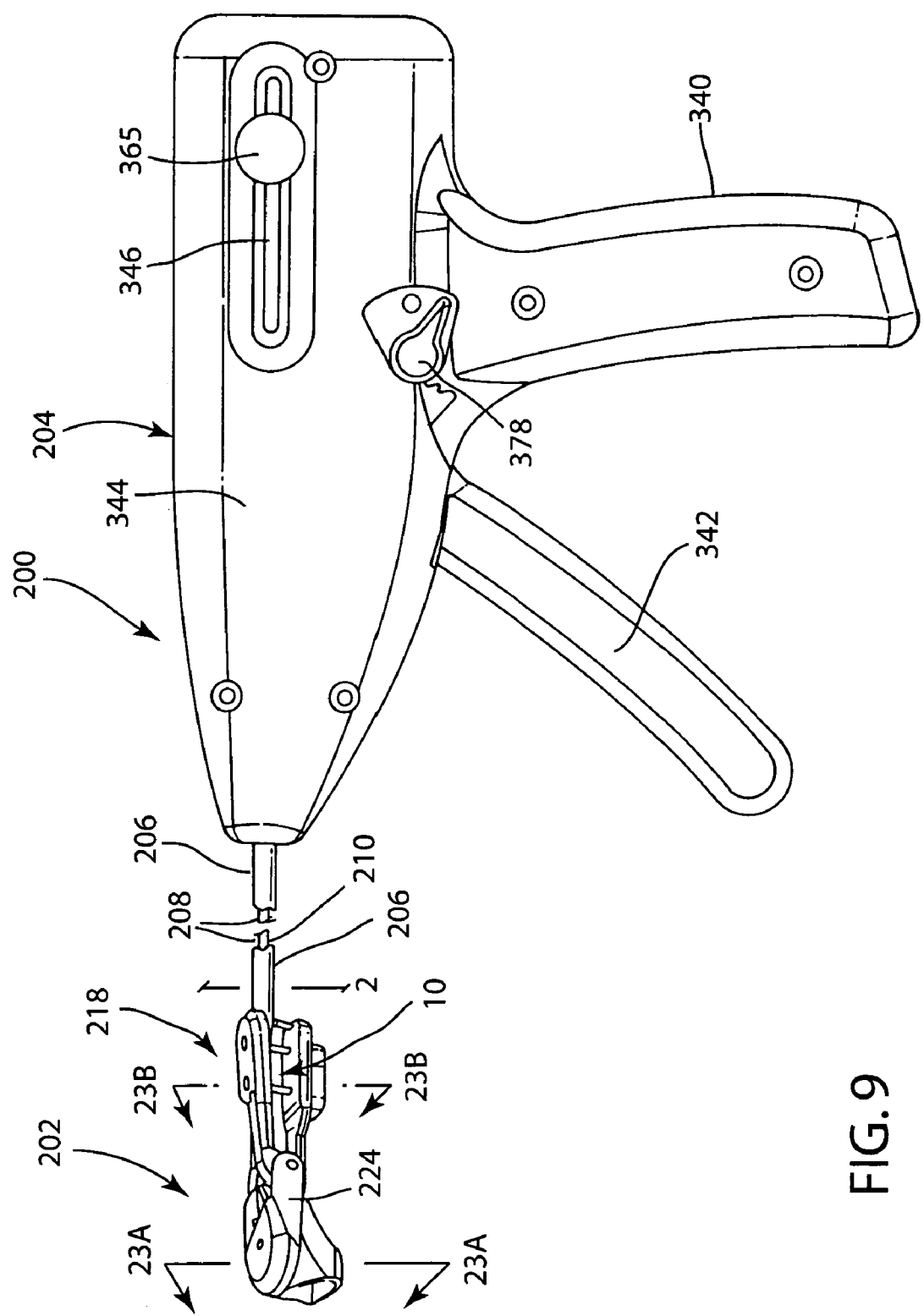
FIG. 9 is a broken side view of an endoluminal tissue plication and fastener applicator instrument according to the invention, shown with a fastener in the end effector.

Turning now to FIG. 9, an endoluminal tissue plication and fastener applicator instrument 200 is shown. The instrument 200 generally includes a distal end effector 202, a proximal actuation handle 204, and a tubular control shaft 206 housing first and second control elements 208, 210 (wire, cables, coils, ribbons, etc.) extending between the handle 204 and the end effector 202.

The control shaft 206 is preferably a stainless-steel flat wire wound coil covered in a lubricious sheath, and is substantially smaller in diameter than a conventional endoscope. The flat wire limits elongation of the control shaft when the control shaft is under tension due one or the other of the control elements 208, 210 being under compression. Alternatively, a rounded wire coil can be used which permits the control shaft to bent into a tighter radius than the flat wire wound coil. In addition, the control shaft 206 has a relatively small diameter relative to the distal end effector 202, preferably not exceeding 5 mm and more preferably approximately 4 mm.

The distal end effector 202 is adapted to plicate tissue and apply the two-part fastener 10 to opposed sections of the plicated tissue, and according to several embodiments is optionally adapted to be coupled to an endoscope, as described in detail below. The actuation handle 204 operates the control elements 208, 210 to effect clamping and opening of the jaw assembly 218 and locking and release of the fastener 10, as also described in detail below.

Figure 10:
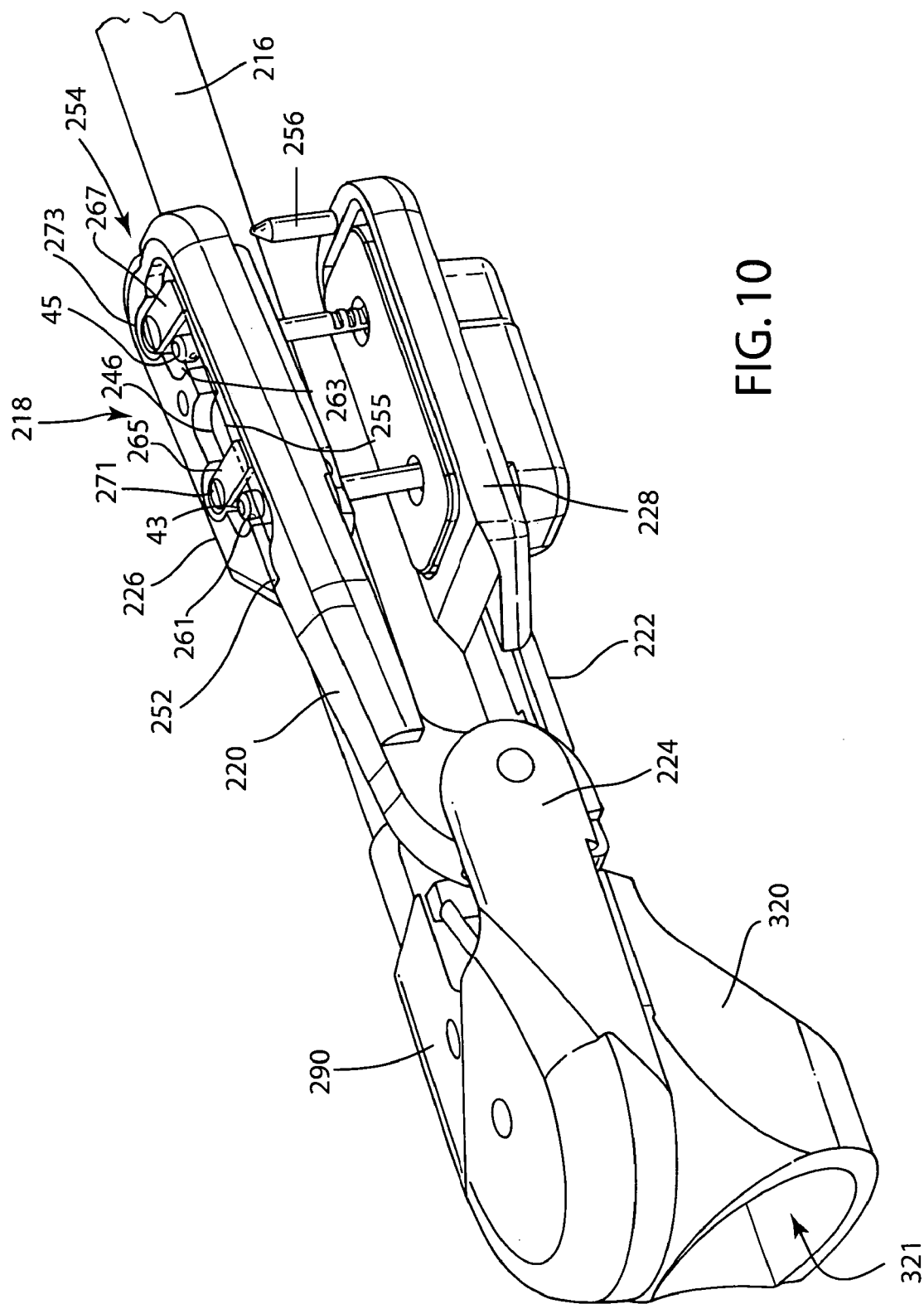
FIG. 10 is a side end perspective view of the distal end of the instrument of FIG. 9, shown with a fastener in the end effector.
Figure 11:
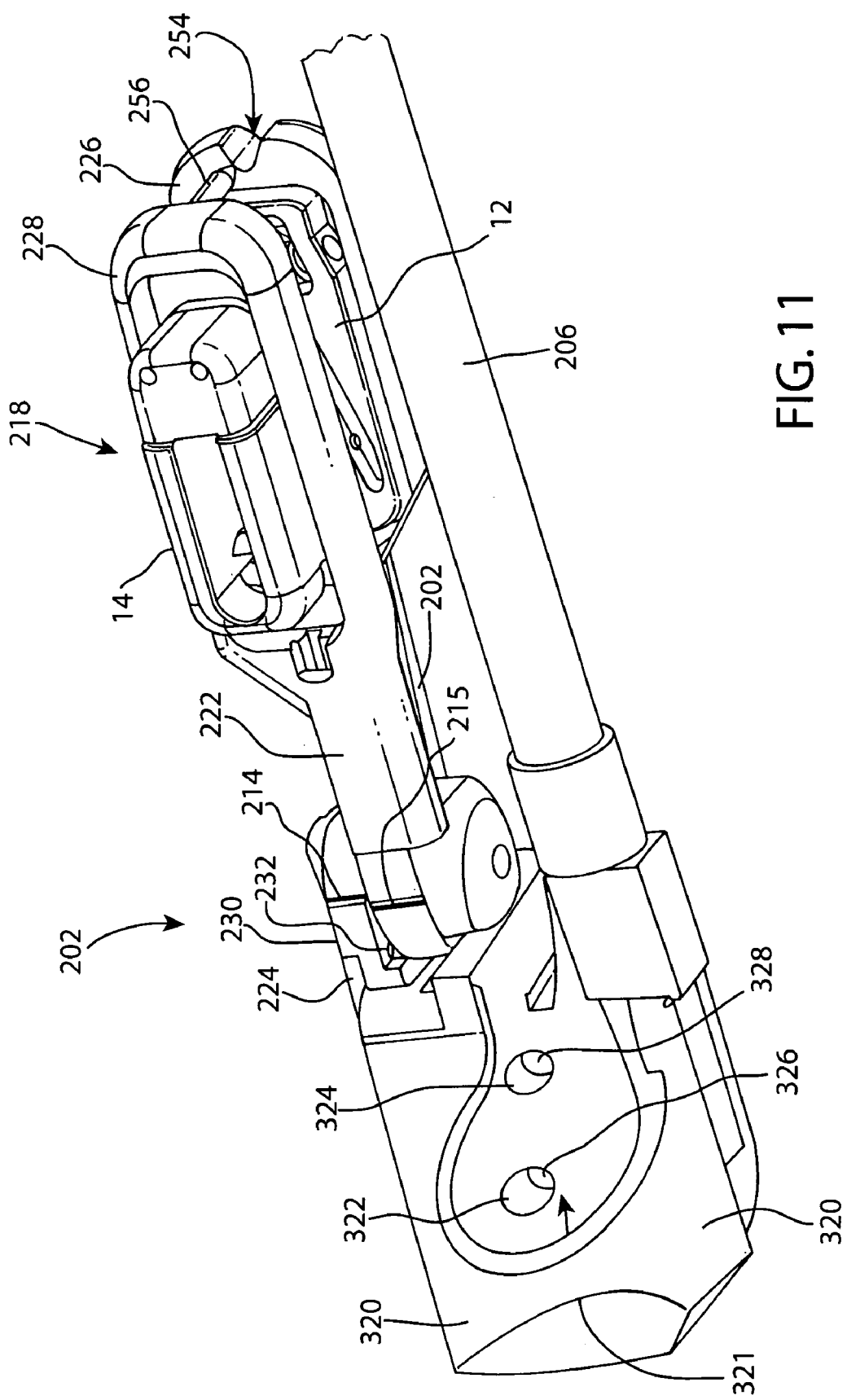
FIG. 11 is a top perspective view of the distal end of the instrument of FIG. 9, shown with a fastener in the end effector, but without the female jaw torsion spring.
Figure 12:
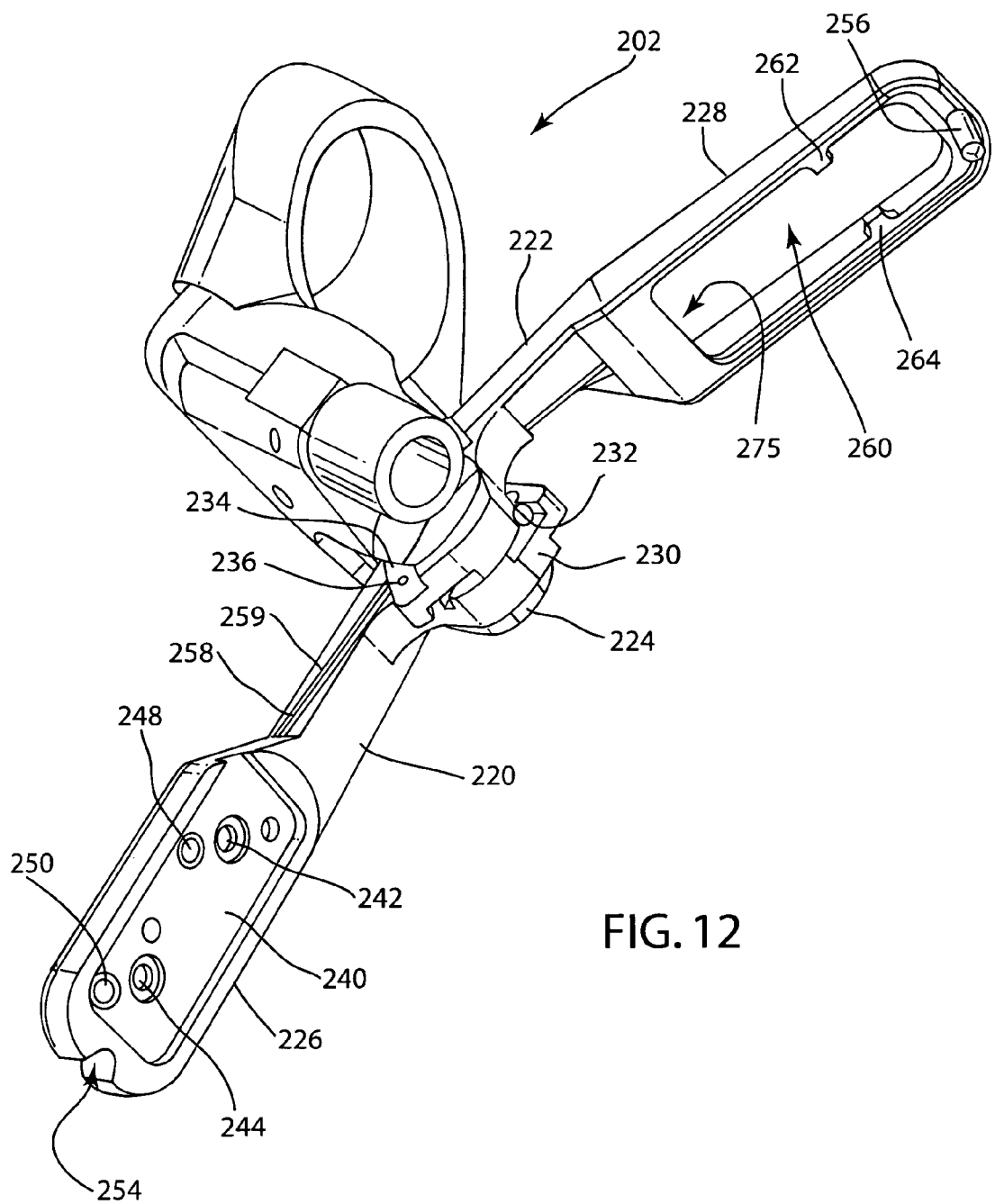
FIG. 12 is a perspective view of the distal end of the instrument, with control shaft removed for clarity, and shown with the jaws in an open configuration and without the fastener.

Referring now to FIGS. 10 through 12, the distal end effector 202 includes a jaw assembly 218 having a clevis 224, first and second arms 220, 222 mutually rotatable about the clevis 224, a housing 290, and a sleeve (continuous or slit cuff) 320 integral with the housing 290 and adapted to be slidably positioned about (or, if slit, snapped over) an end of an endoscope.

The first arm 220 of the jaw assembly 218 includes a male jaw 226 (adapted to receive the male part 12 of the fastener 10), and an opposite tang 230 having a coupling hole 232 adapted to receive a wire-like element. The second arm 222 includes a female jaw 228 (adapted to receive the female part 14 of the fastener 10), and an opposite tang 234 having a coupling hole 236.

Figure 13:
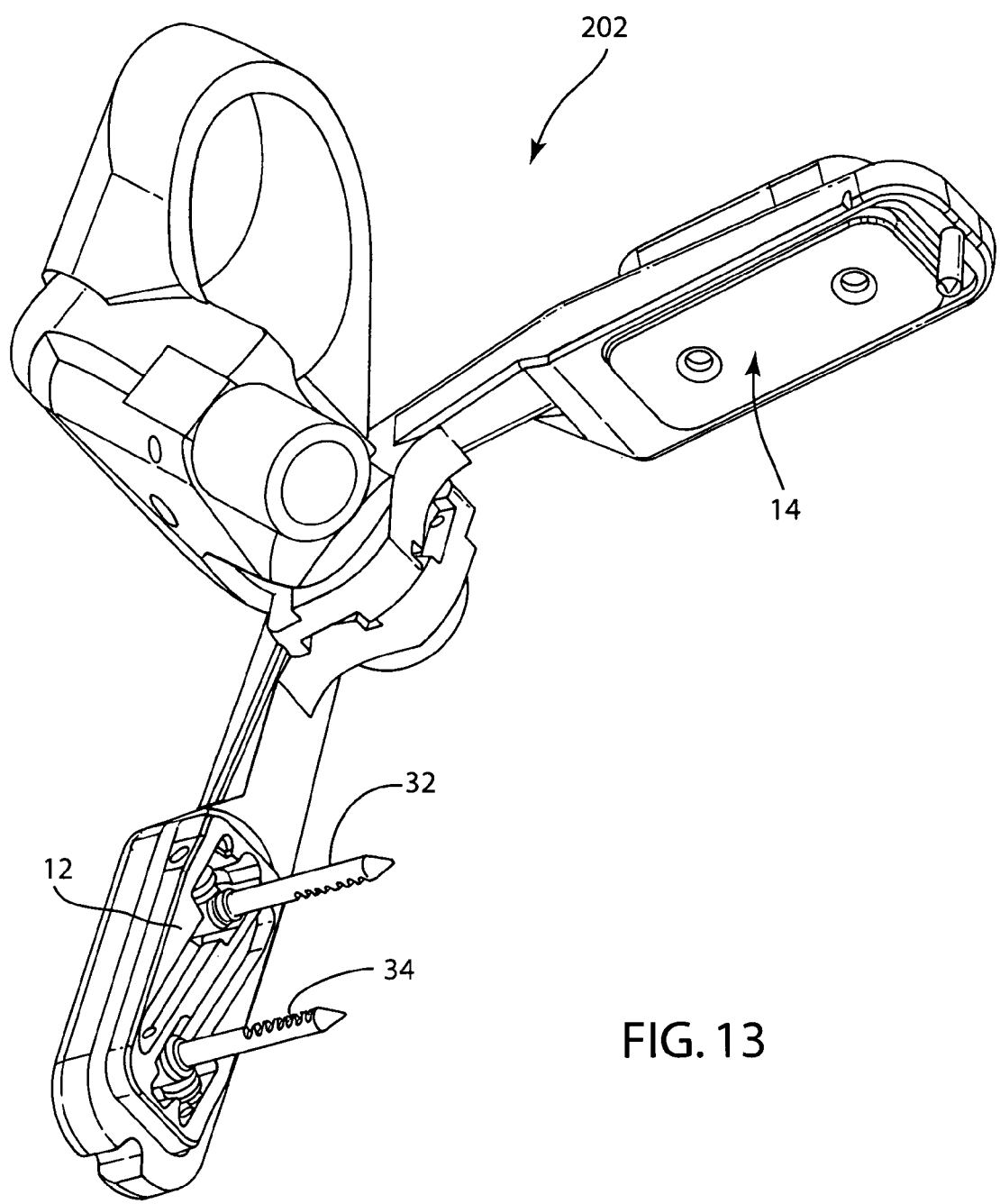
FIG. 13 is a view similar to FIG. 12, shown with the fastener.

More particularly, the inside of the male jaw 226 includes a rectangular recess 240 adapted to receive the back of the male part 12 of the fastener 10, two stepped throughbores 242, 244, and two threaded holes 248, 250. Referring to FIGS. 3 and 13, when the male part 12 is loaded into and held within the recess 240 of the male jaw 226, the lower portions 43, 45 as well as portions of the enlarged portions 33, 35 of the posts 32, 34 are received in the stepped throughbores 242, 244. This retains the posts 32, 34 in an upright configuration and consequently prevents their rotation into a collapsed configuration. Referring back FIGS. 10 and 12, the outside of the male jaw 226 also includes a recess 246 through which the threaded holes 248, 250 are accessed, and an exit opening 252 in communication with a track 258 (which carries a release element, discussed below) through the first arm 220. The end of the male jaw 226 is also provided with a groove 254, the function of which is described below.

A first release element 259 extends within the track 258 of the first arm 220 from a housing 290 of the clevis 224 and through the exit opening 252. The first release element 259 includes an actuation end 255 which is split to define two U-shaped portions 261, 263 which are respectively inserted into the bores 46, 48 (FIG. 3) of the lower end 43, 45 of the posts 32, 34 of the male part of the fastener. Friction plates 265, 267 are held over the U-shaped portions 261, 263, with screws 271, 273 inserted into the threaded holes 248, 250, to provide frictional resistance from inadvertently dislodging the U-shaped portions from within the bores 46, 48.

Figure 14:
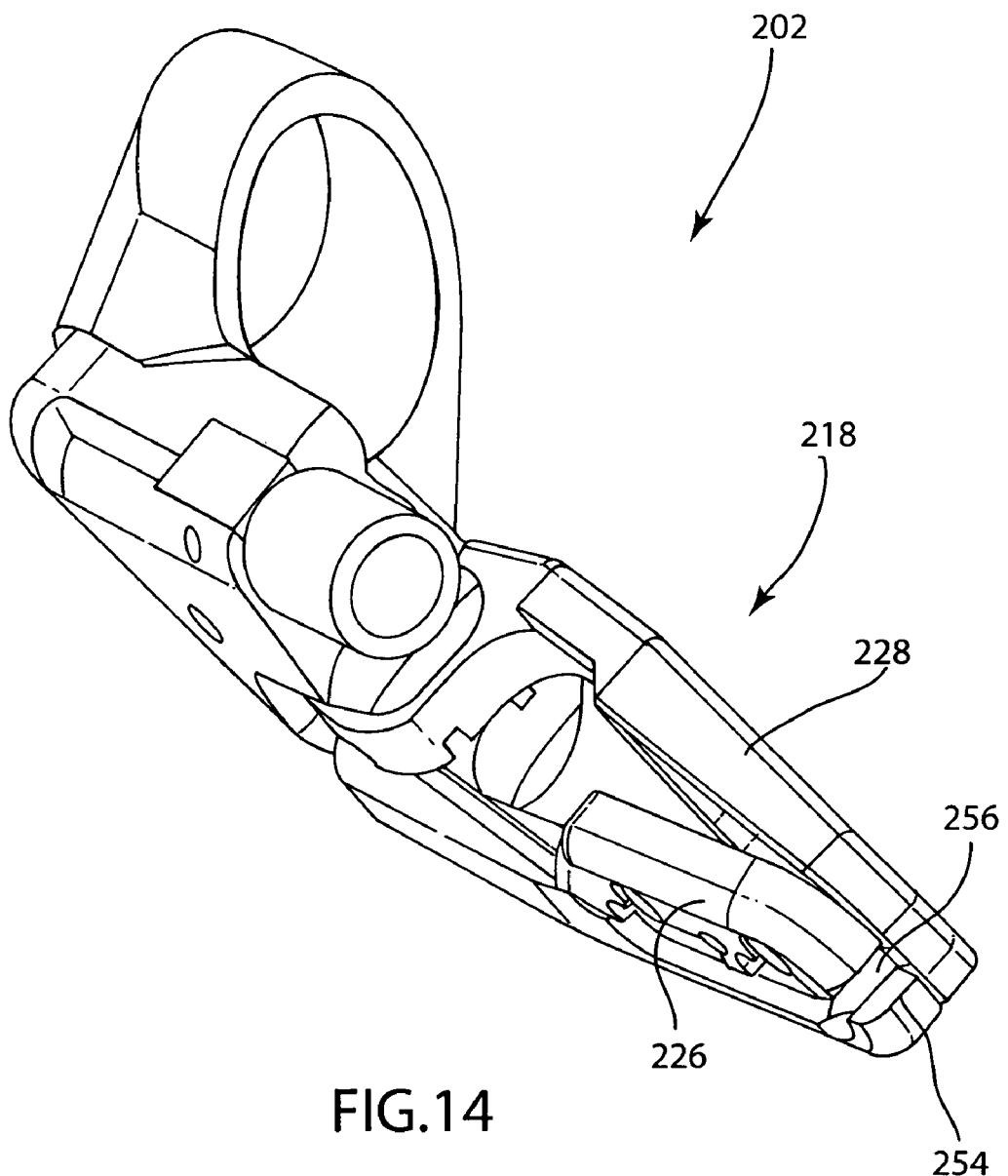
FIG. 14 is a perspective view of the distal end of the instrument, with control shaft removed for clarity, and shown with the jaws in a closed configuration and without the fastener.
Figure 15:
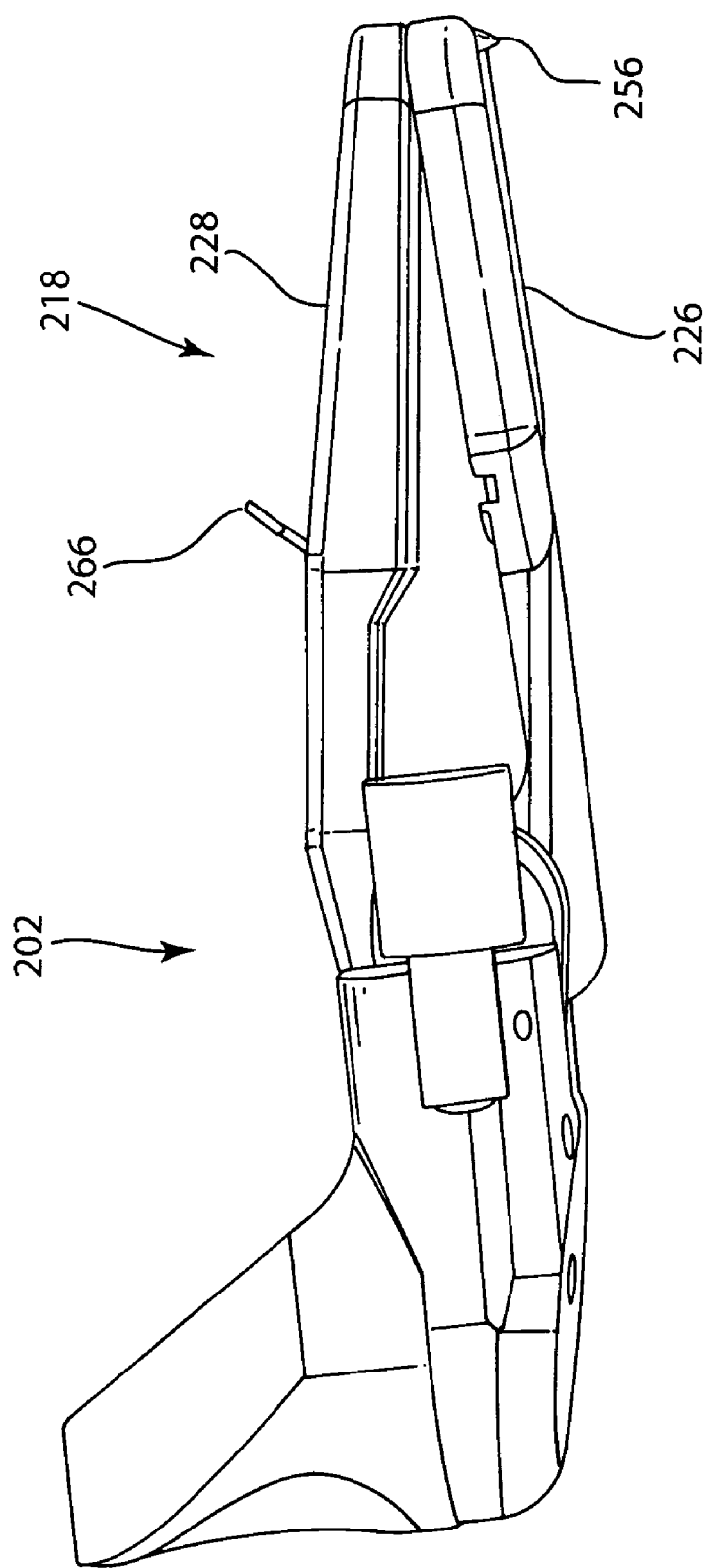
FIG. 15 is a side elevation view of the distal end of the instrument, with control shaft removed for clarity, and shown with the jaws in a closed configuration and without the fastener.

Referring to FIGS. 11 through 13, the female jaw 228 includes a relatively large generally rectangular opening 260 sized to receive the latch body cover 56 and latch slide cover 74 of the female part 14 of the fastener 10. The jaw 228 also defines a ledge 275 (FIG. 16), and two catches 262, 264 that extend into the opening. The female part 14 is inserted into the jaw 228 in the locked position and then moved into the unlocked position such that the head 76 of the latch slide 70 (FIG. 5) lies over the ledge 275 and the catches 262, 264 extend within the setback 112 (FIG. 5) to lock the part 14 in the jaw 228. A tissue piercing post 256 is provided to the terminus of the female jaw 228. Referring to FIGS. 14 and 15, when the female and male jaws 226, 228 are free of the fastener parts 12, 14 and closed together (e.g., after the fastener has been released and during retraction of the instrument), the post 256 resides in the groove 254 of the male jaw 226 to provide a more tapered configuration to aid in removal of the instrument from the patient.

Figure 16:
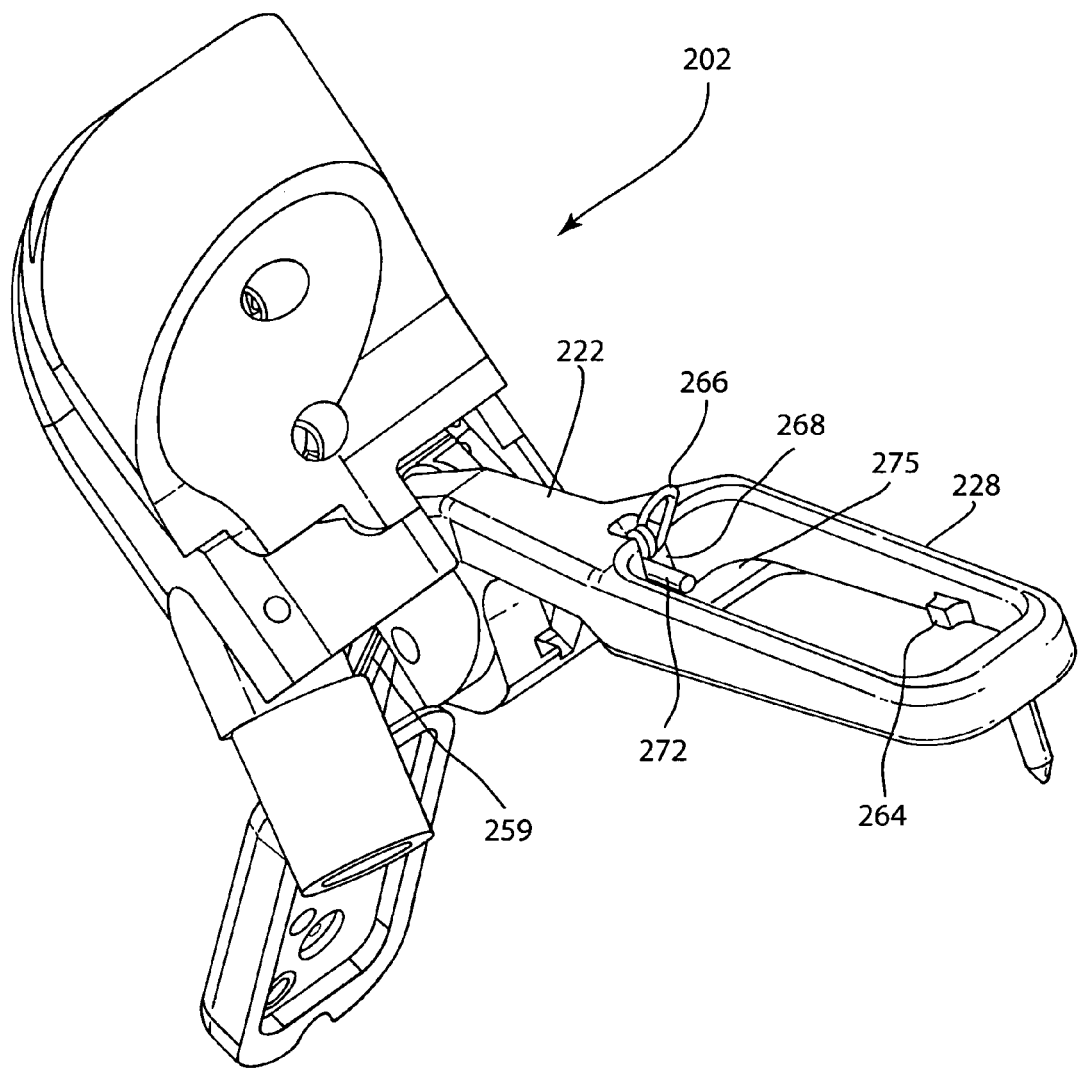
FIG. 16 is a perspective view of the distal end of the instrument, with control shaft removed for clarity, and shown with the jaws in an open configuration and without the fastener.
Figure 17:
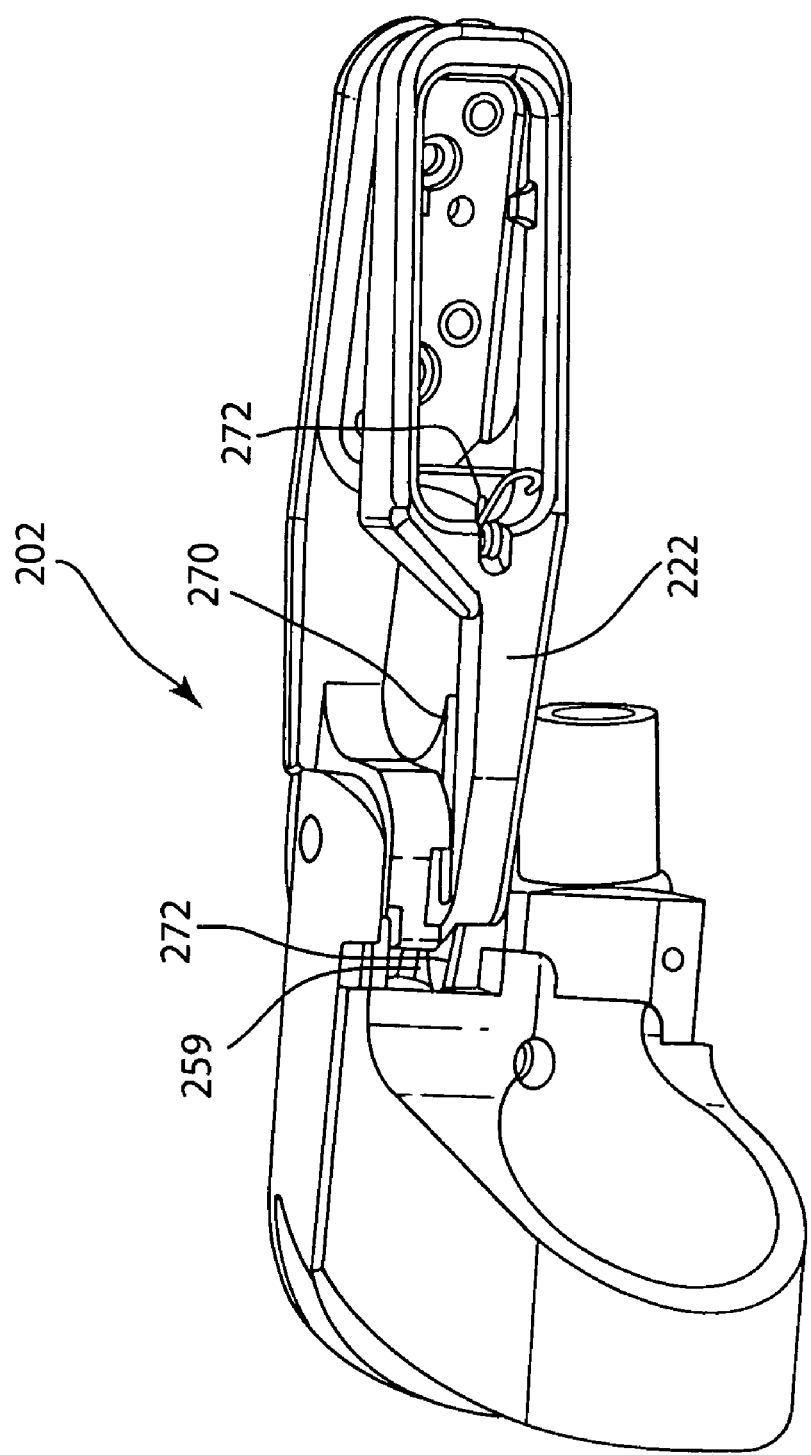
FIG. 17 is a perspective view of the distal end of the instrument, with control shaft removed for clarity, and shown with the jaws in a closed configuration and without the fastener.

Referring now to FIGS. 15 and 16, a torsion spring 266 is coupled to the female jaw 228 and adapted to force the female part 14 of the fastener 10 toward the terminus of the jaw. This operates to help align the male and female parts 12, 14 as the jaws 226, 228 are rotated toward each other through an arc. Moreover, the spring 266 permits movement of the female part 14 within the opening 260 to accommodate misalignment due to the amount of the tissue between the fastener parts. Referring to FIGS. 16 and 17, the female jaw 228 also includes an exit opening 268 for a wire track 270 extending along a side of arm 222. A second release element 272 extends within the track 270 from the housing 290 through the exit opening 268, as described further below.

Figure 18:
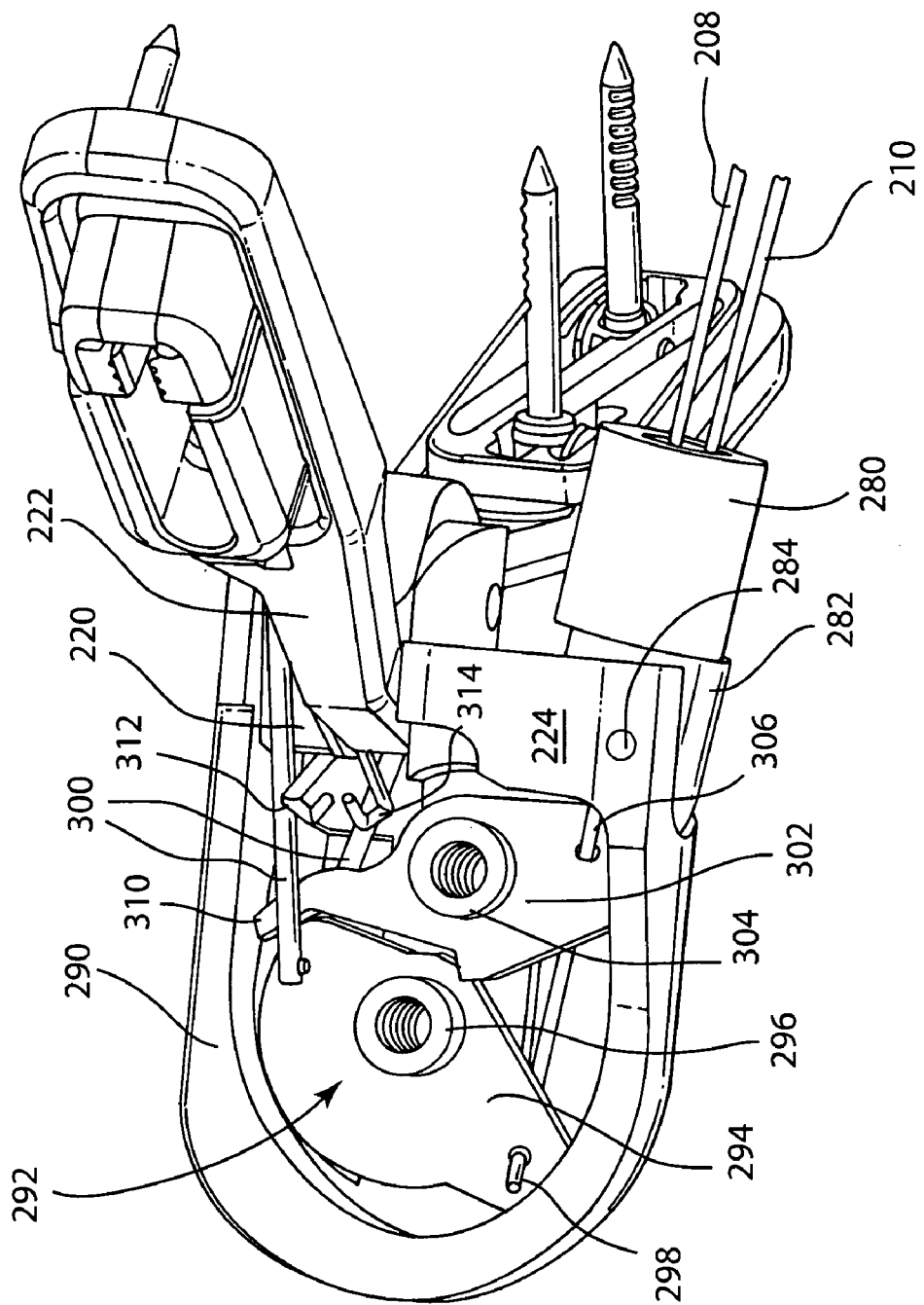
FIG. 18 is a perspective view of the distal end of the instrument, with the control shaft and the mounting sleeve removed for clarity, and shown with the jaws in an open configuration with a fastener.

Referring now to FIG. 18, the clevis 224 also includes a mount 280 at which the control shaft 206 (FIG. 9) is attached to the distal end effector 202 of the instrument 200. The mount 280 includes a bracket 282 that is coupled to the clevis 224 at pivot 284. The clevis 224 also defines a housing 290 for a mechanical assembly 292 which operates to transmit an input force on the control elements 208, 210 to the end effector 202 to effect movement of the jaw arms 220, 222 and locking and release of the fastener 10 therefrom.

Figure 19:
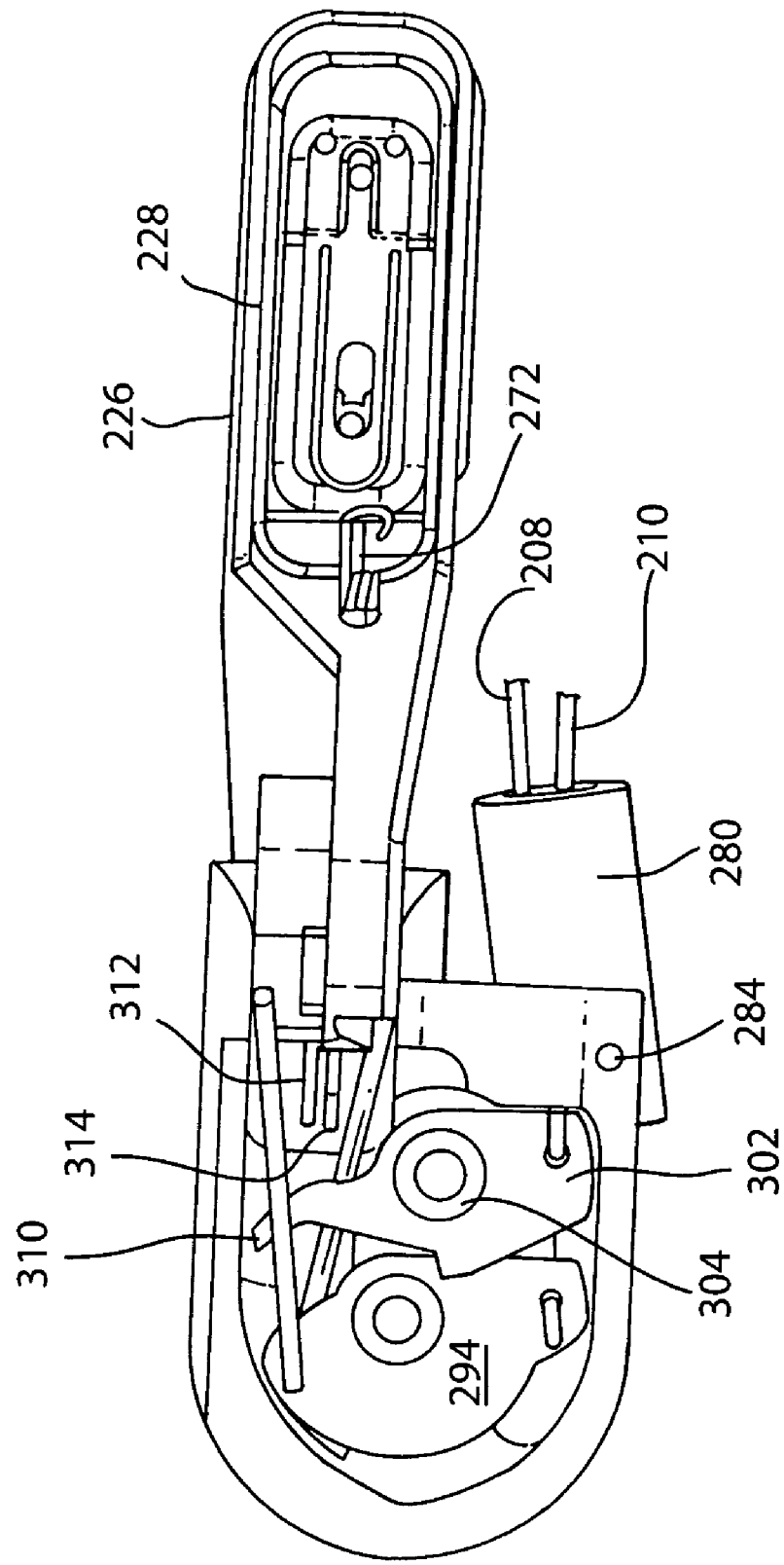
FIG. 19 is a plan view of the distal end of the instrument, with the control shaft and the mounting sleeve removed for clarity, and shown with the jaws in a closed configuration with a fastener.

More particularly, the mechanical assembly 292 preferably includes a first bell crank 294 rotatably coupled about a pivot 296 that is preferably integrally formed with the housing. A distal end 298 of control element 208 is coupled to the first bell crank 294 at an input side of the bell crank, and a V-shaped wire 300 is attached to the bell crank at an output side of the bell crank. The V-shaped wire 300 extends to and is coupled within the coupling holes 232, 236 (FIG. 12) of the tangs 230, 234 of both of the two jaw arms 220, 222. Alternatively, two separate wires can be used to extend from the output side of the bell crank to the two tangs. Referring to FIGS. 18 and 19, when control element 208 is moved distally relative to the control shaft, the first bell crank 294 is rotated, pulling the V-shaped wire 300 away from the jaws and thereby rotating the jaws 226, 228 into a closed position. Still referring to FIGS. 18 and 19, it is also noted that when the jaws 226, 228 are forced into a completely closed position, additional force on control element 208 causes rotation of the mount 280 about the pivot 284 to cause the jaws to move closer to the control shaft 206. This reduces the profile of the end effector to aid in removal of the instrument from the stomach and esophagus after a fastener 10 has been released from the instrument 200. When control element 208 is moved proximally relative to the control shaft 206, the first bell crank 294 is rotated to cause the V-shaped wire 300 to forcibly rotate the jaws 226, 228 into an open position. In addition, referring back to FIG. 18, when the jaws 226, 228 are in a fully opened position, additional force on control element 208 causes rotation of the mount 280 about the pivot 284 which pushes the jaw assembly 218 away from the control shaft 206. This provides additional space between the jaw assembly 218 and the control shaft 206 to facilitate grabbing tissue between the jaws 226, 228.

Referring still to FIGS. 18 and 19, the mechanical assembly 292 also includes a second bell crank 302 that is rotatably coupled about a pivot 304 which is also preferably integrally formed with housing 290. A distal end 306 of control element 210 is attached to one side of the second bell crank 302. Another side of the second bell crank 302 defines a push bar 310. The ends of release elements 259, 272 (FIG. 17) terminating within the housing 290 are preferably bent or otherwise formed at an angle such as to define contact portions 312, 314 (FIGS. 18 and 19) which, when the jaw arms 220, 222 are in a closed position (FIG. 19), are oriented substantially perpendicular to the orientation of the push bar 310.

Figure 20:
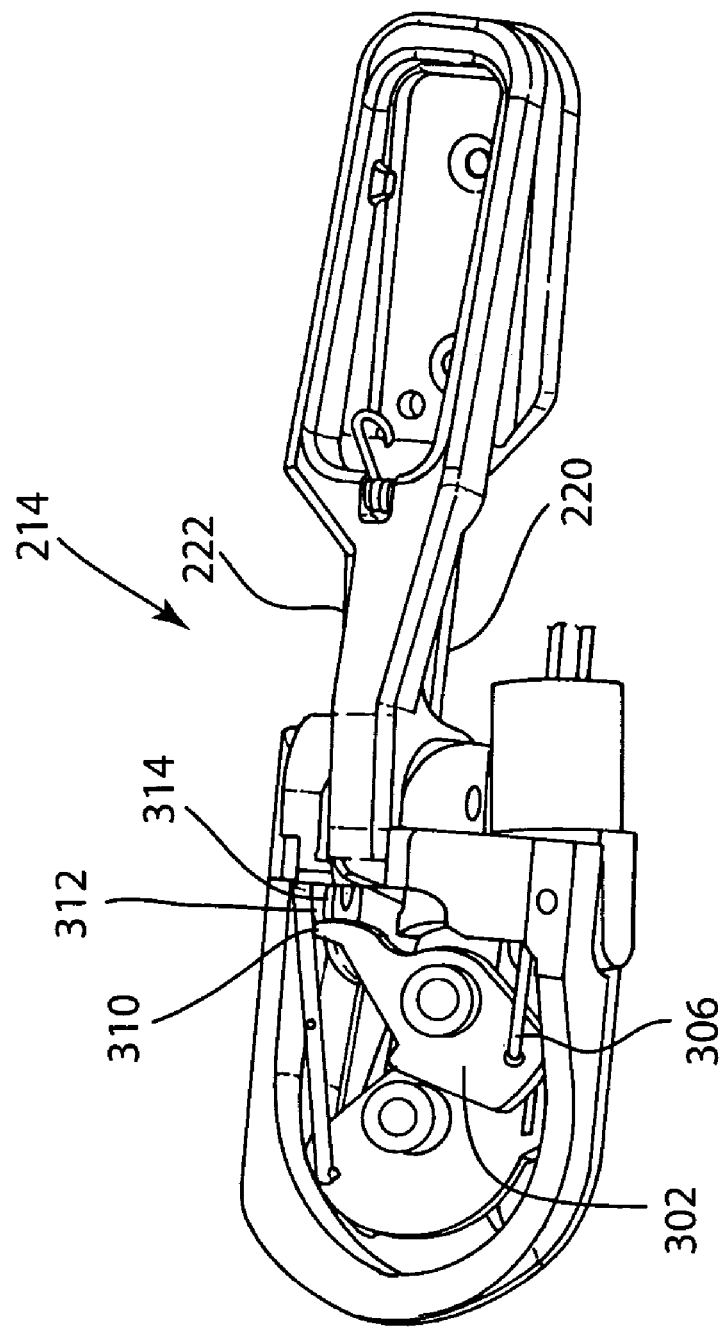
FIG. 20 is a perspective view of the distal end of the instrument, with the control shaft and the mounting sleeve removed for clarity, and shown with the jaws in a closed configuration without a fastener.

Referring now to FIGS. 19 and 20, when the jaws are in a closed position and control element 210 is pushed distally relative to the control shaft 206 to apply a pushing force to the second bell crank 302, the push bar 310 is forced against the contact portions 312, 314 and moves the release elements 259, 272 (FIG. 16) into the respective jaws 226, 228. This effects both locking together the male and female parts 12, 14 of the fastener 10 and release of fastener 10 from the jaws 226, 228, as follows. First, when the end of release element 272 is pushed against the sliding assembly 52, the sliding assembly is forced to move relative to the latch body 50. This locks the catches 96, 98 of the latch lock 72 relative to the posts 32, 34, and thereby locks the male and female parts 12, 14 of the fastener together. Second, movement of the sliding assembly spaces moves the latch slide cover 74 to free the head 76 of the latch slide from the ledge 275 and free the catches 262, 264 of the female jaw 228 from the setback 112 (aligning space 108 (FIG. 6) with the catches 262, 264), to thereby release the female part 14 from the female jaw 228. Third, the U-shaped ends 261, 263 (FIG. 10) of the bifurcated release element 255 are moved out of the bores 46, 48 of the posts 32, 34 to release the male part 12 from the male jaw 226. It is noted that the force on release element 255 is sufficient to overcome the friction created by plates 265, 267.

It is noted that the push bar 310 is decoupled from the release elements 259, 272 as the contact portions 312, 314 of the release elements will be differently located relative to the push bar 310 based upon whether large or small amounts of tissue are located between the closed jaws 226, 228 and to what degree the jaws are closed. This decoupled adjustable mechanism operates to effect the appropriate amount of movement to the release elements regardless of the exact closed jaw configuration.

Alternatively, rather than use a bell crank system in which control element 208 is placed under tension to close the jaws and control element 210 is placed under compression to operate the lock the fastener parts and release the fastener from the jaws, another system may be used to couple the control elements 208, 210 to the jaws 226, 228 and release elements 259, 272, respectively. For example, each of the control elements may include an end provided with a U-shape in which the end of the control element defines a return extending non-coaxial but parallel to the remainder of the control element. For example, the U-shaped end of the control element 208 can be coupled to the jaws such that when control element is placed under compression the return portion of the U-shape pulls the jaws closed. Similarly, the U-shaped end of the control element 210 can be configured to act on release elements 259, 272 such that control element is placed under tension to the U-shaped portion pushed on the release elements 259, 272. Other mechanisms may likewise be used.

Referring back to FIGS. 10 and 11, the sleeve 320 of the distal end effector 218 preferably has an opening 321 with a diameter of approximately 9 mm, corresponding to the diameter of a relatively small endoscope. The exterior dimensions of the sleeve 320 are minimized to provide as low a profile as possible to facilitate passage of the distal end effector 218 through the tracheoesophageal passage of a patient. The sleeve 320 may also be provided with a slant nose or other tapered or otherwise streamlined shape that further facilitates introduction and withdrawal of the distal end effector 202 through the tracheoesophageal passage. In addition, the sleeve 320 is preferably constructed of a preferably soft, low friction, lubricious material such as polytetrafluoroethylene (PTFE), nylon, or silicone to aid in movement over the endoscope and prevent injury to the human body. The sleeve 320 is coupled over the housing 290 to enclose the mechanical assembly 292 (FIG. 18). To facilitate the coupling of the sleeve 320 to the end effector 202, it is preferable that the sleeve 320 be provided with two holes 322, 324 and that pivots 296 and 304 (FIG. 18) for the first and second bell cranks 294, 302 be provided with an internal thread (FIG. 18). Screws 326, 328 are inserted in holes 322, 324 and thread into the pivots 296, 304 to lock the sleeve over the housing 290.

Figure 21:
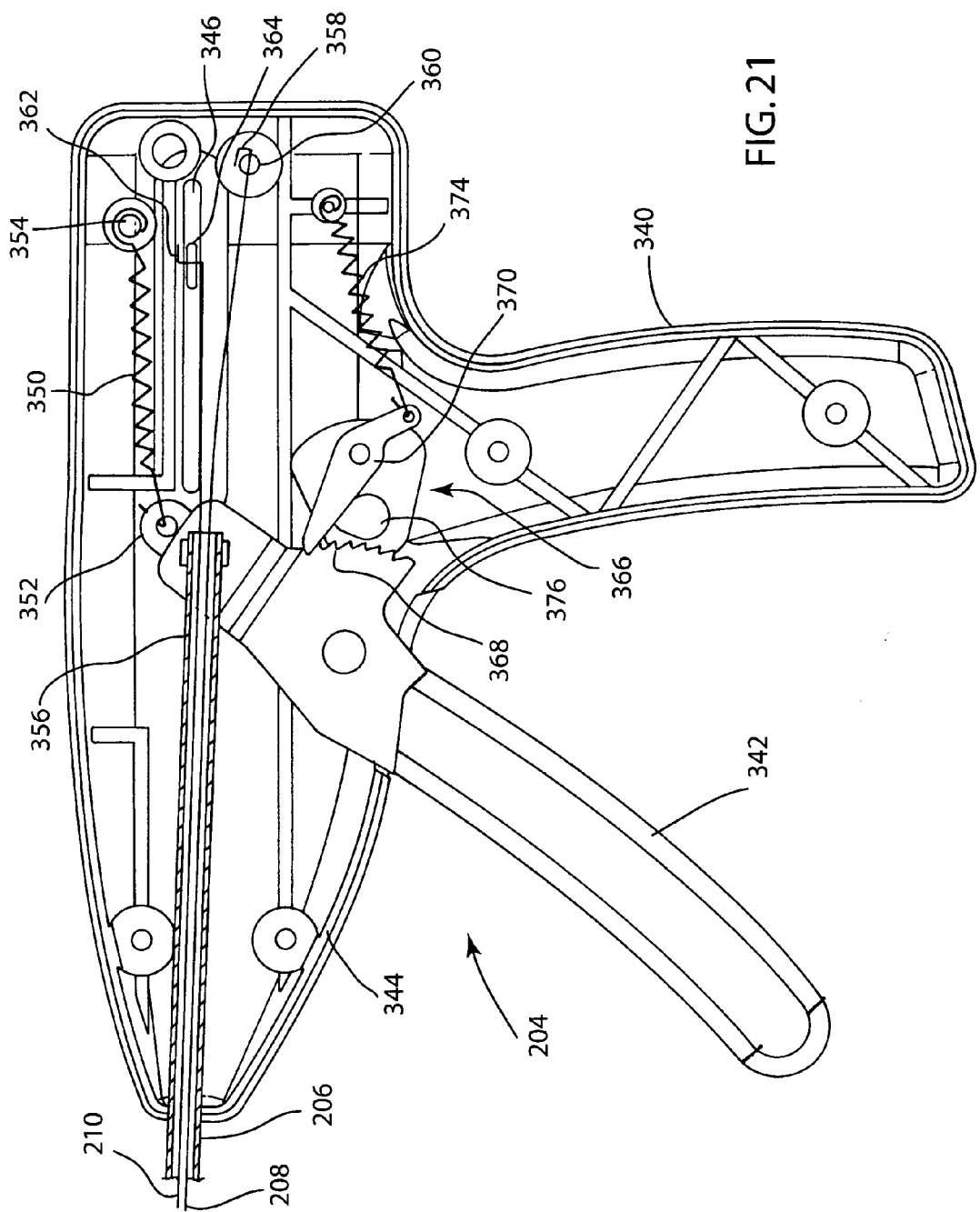
FIG. 21 is a partial view of the proximal actuation handle of the instrument of the invention.

Referring now to FIGS. 9 and 21, the proximal actuation handle 204, which according to one embodiment is a pistol-grip style handle, includes a stationary handle 340, and a lever 342 rotatable relative thereto. The stationary handle 340 is integral with a housing 344 which defines a longitudinal slot 346. A proximal end 356 of the control shaft 206 extends into the housing 344 and is coupled to an upper portion of the lever 342. The first control element 208, which is coupled at its distal end 298 to the jaw arms 220, 222 via the first bell crank 294, includes a proximal end 358 that extends out of the proximal end 356 of the control shaft 206 and is fixed at a second mount 360 within the housing 344. The second control element 210, which operates to lock and release the fastener 10 via the second bell crank 302, includes a proximal end 362 that is coupled to a cross bar 364 movable within the longitudinal slot 346. The cross bar 364 includes a handle portion 365 (FIG. 9) located external the housing 344. The lever 342 is biased into an open position with a first spring 350 that is coupled between a lever mount 352 on the lever and a first mount 354 within the housing 344. The lever 342 is also provided with a locking system 366 that operates to lock the position of the lever relative to the handle 340. The locking system 366 includes a plurality of teeth 368 on the lever, a pawl 370 mounted on a pivot 372 and biased with a second spring 374 toward the teeth 368, and a cam 376 that can be manually rotated with an external knob 378 (FIG. 9) to contact the pawl 370 and effect disengagement of the pawl from the teeth 368.

In operation, when the handle lever 342 is rotated toward to the stationary handle 340, the control shaft 206 is moved distally relative to the first control element 208 to effect closing the jaws 226, 228. With the jaws in a closed position, the cross bar 364 can be moved distally relative to the stationary handle 340 in order to operate the second bell crank 302 (via control element 210) to cause lock and release of the fastener 10. After a fastener 10 is released, the cam 376 can be operated to release the handle locking system 366 and permit the handle lever 342 to rotate relative to the stationary handle 340, thereby allowing the jaws to reopen.

While a pistol-grip embodiment of the handle 340 has been shown for operation of the instrument 200, as such a handle includes significant mechanical advantage, it may be preferred to use an inline-type handle or other handle configured to also provide the desired mechanical advantage.

The instrument 200 is highly torqueable with great ability to direct the end effector via manipulation of the handle in gross. That is, the instrument 200 has a torsionally rigid flexible shaft particularly for its length of at least approximately 150 cm, and more likely 190 cm length. This torqueability permits the end effector assembly 212 to be rotated through 180° (for any approach toward the target tissue) via rotation of the handle preferably by no more than approximately 180°. This is facilitated, in part, by control element 208 being rotational fixed to the handle 340. Control element 208 is relatively large in diameter, and is most preferably an approximately 0.035 inch stainless steel wire. A wire of similar construct having a diameter preferably between approximately 0.020 inch and approximately 0.062 inch should also be suitable.

Figure 22:
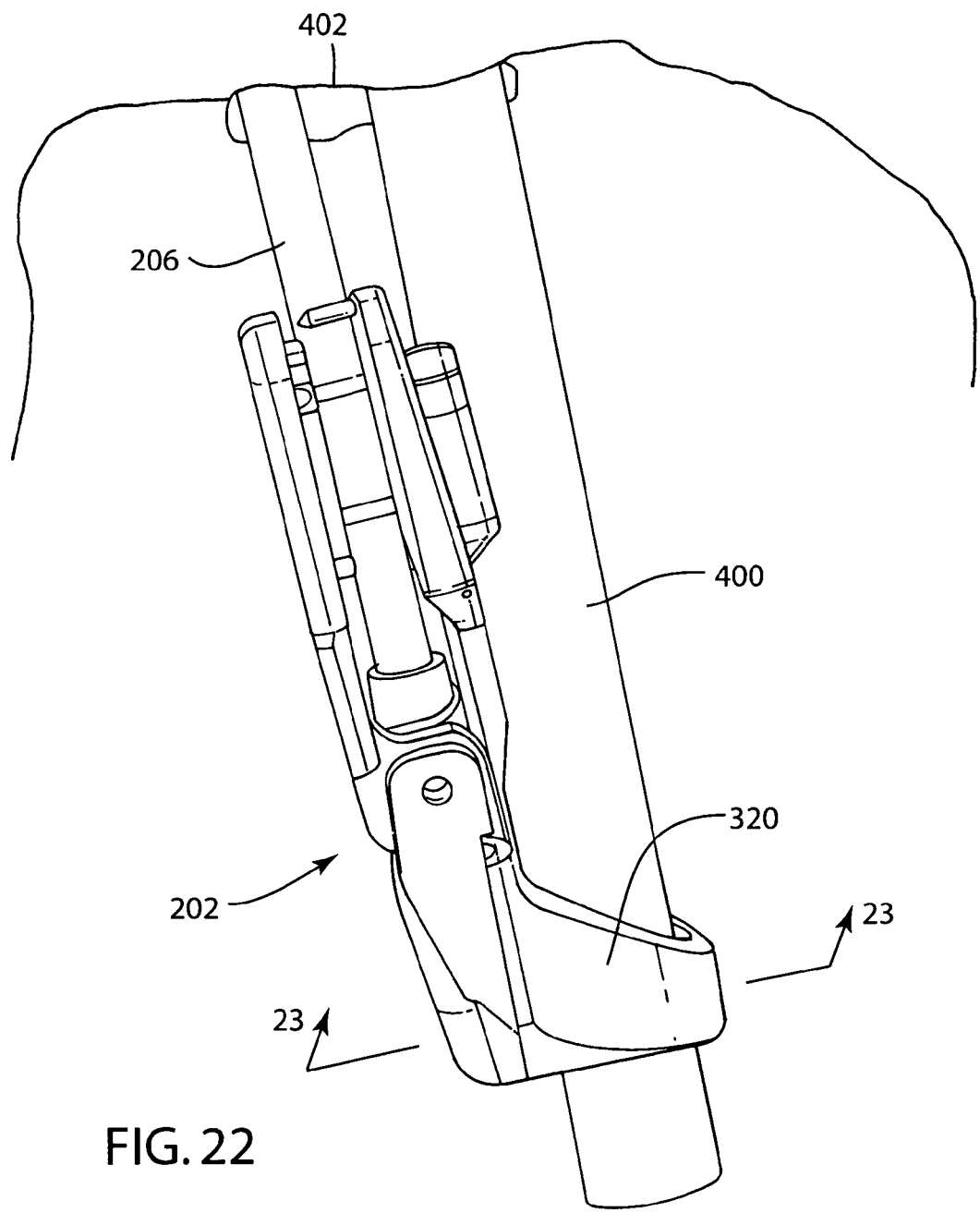
FIG. 22 illustrates the instrument of the invention coupled to an endoscope during insertion of the two into the stomach.

According to one embodiment of the method of the invention, the instrument 200 may be operated as follows with respect to the treatment of GERD. Turning to FIG. 22, the sleeve 320 of the distal end effector 202 is slidably coupled over the distal end of an endoscope 400 and the end effector is slid proximally over the endoscope. The distal end of the endoscope 400 is then inserted into the tracheopharangeal passage and moved through the esophagus and into the stomach, with the end effector 202 of the instrument 200 mounted preferably approximately 20 cm back from the distal end of the endoscope 400. The handle 204 and/or control shaft 206 are then manipulated in gross to slide the distal end effector 202 over the distal end of the inserted endoscope 400 and into the stomach, with the endoscope 400 functioning as a guidewire for the sleeve 320. The endoscope 400 may optionally be retroflexed to look back toward to the LES 402 of the esophagus and visualize the advancement of the end effector 202.

Figure 23A:
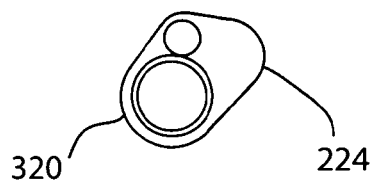
FIG. 23A is an end view schematic illustration of a cross-sectional area across line 23A—23A in FIG. 9 across a portion of the distal end effector of the instrument.
Figure 23B:
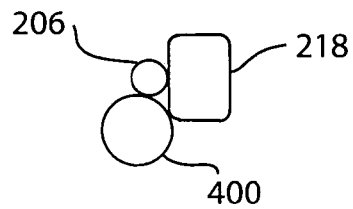
FIG. 23B is an end view schematic illustration of a cross-sectional area across line 23B—23B in FIG. 9 across a portion of the distal end effector of the instrument.
Figure 24:
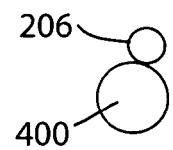
FIG. 24 is a schematic illustration of the cross-sectional area of the endoscope and the control shaft.

Referring to FIG. 23A, it is particularly noted that during insertion of the end effector over the endoscope and into the patient (and later withdrawal of the end effector from the patient), the maximum cross-sectional area of the system extending within the esophagus occurs with the combined area of the sleeve 320 and the portion of the clevis 224 that extends outside the footprint of the sleeve; i.e., approximately 188 mm$^2$, smaller than any of the existing or proposed devices in the prior art. The second largest cross-sectional area of the system within the esophagus is at the location of the jaws 226, 228 with the jaws loaded with a fastener 10. Referring to FIG. 23B, this area includes the footprint of the jaw assembly 218 loaded with a fastener as well as the control shaft 206 and the endoscope 400, and is approximately 178 mm$^2$. The portions of the system having the cross-sectional areas of FIGS. 23A and 23B are located within the esophagus only during insertion and removal of the end effector into the patient. Referring to FIG. 24, at all other times and along all other portions of the present system proximal the distal end effector, the cross-sectional area of the system in the esophagus is substantially smaller, limited to the combined cross-sectional areas of the endoscope 400 (approximately 63.6 mm$^2$ for a 9 mm scope) and the control shaft 206 (approximately 12.6 mm$^2$ for a 4 mm control shaft); i.e., a total cross-sectional area of approximately 76.2 mm$^2$ or less.

Figure 25:
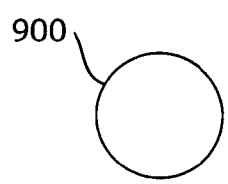
FIG. 25 is a schematic illustration of the cross-sectional area of a prior art device.

In contrast, prior art FIG. 25 shows the relative size of a cross-sectional area corresponding to a prior art device 900 having an 18 mm diameter (254 mm$^2$), such as the NDO device described above in the State of the Art section. This relatively larger area obstructs the esophagus throughout the procedure.

Figure 26:
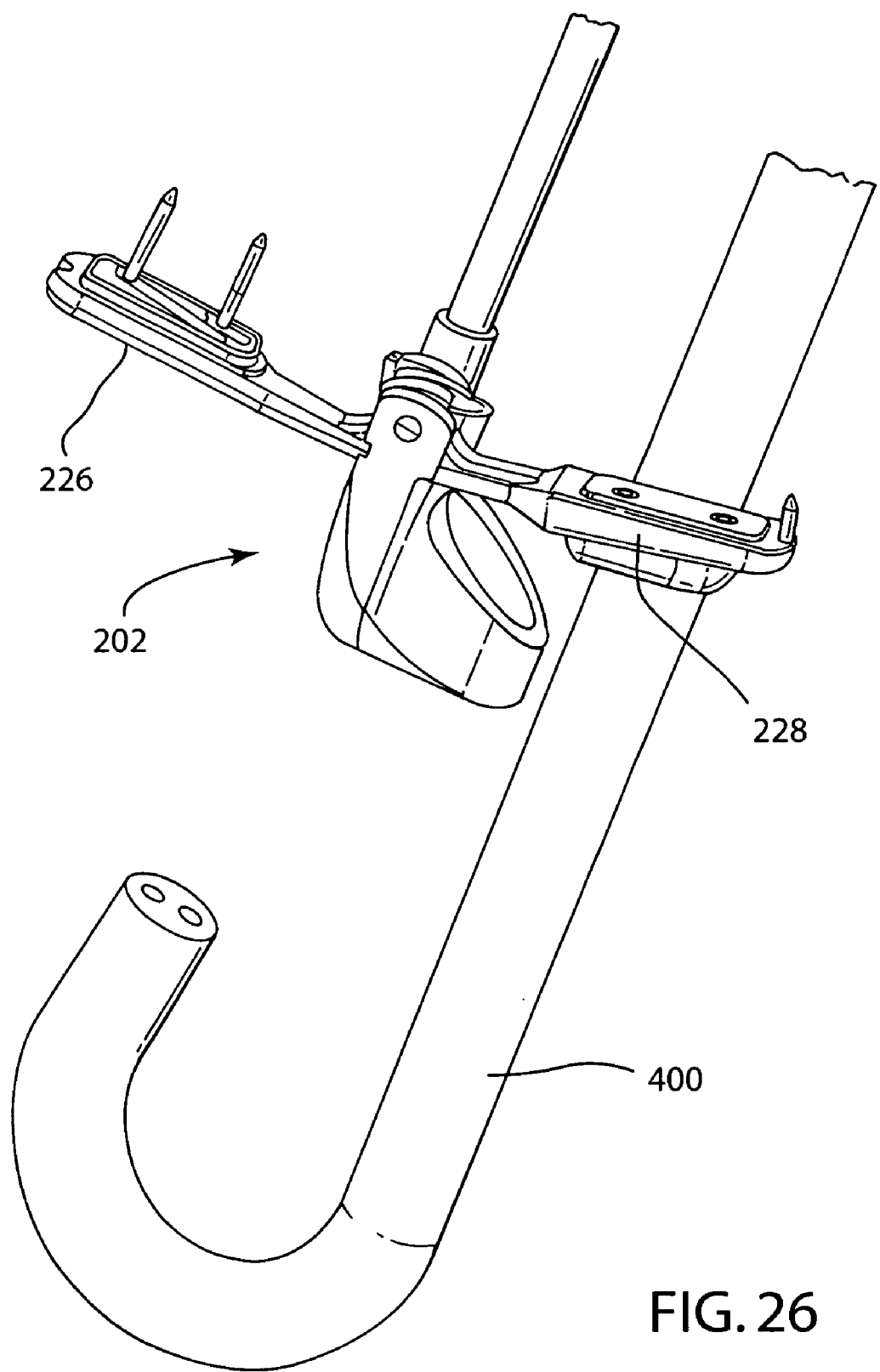
FIG. 26 illustrates the instrument separated from the endoscope and shown with the jaws in an open position.

If the endoscope is retroflexed during insertion of the distal end effector 202, the passage of the distal end effector into the stomach is performed under view of the endoscope 400. Once the distal end effector is located in the stomach, the endoscope is preferably straightened if it was retroflexed, and the end effector is moved distally off the endoscope such that the endoscope 400 and instrument 200 are completely separated. Referring to FIG. 26, the endoscope 400 is then again retroflexed and the instrument handle 204 is operated to open the jaws 226, 228 of the end effector 202, as described above.

Figure 27:
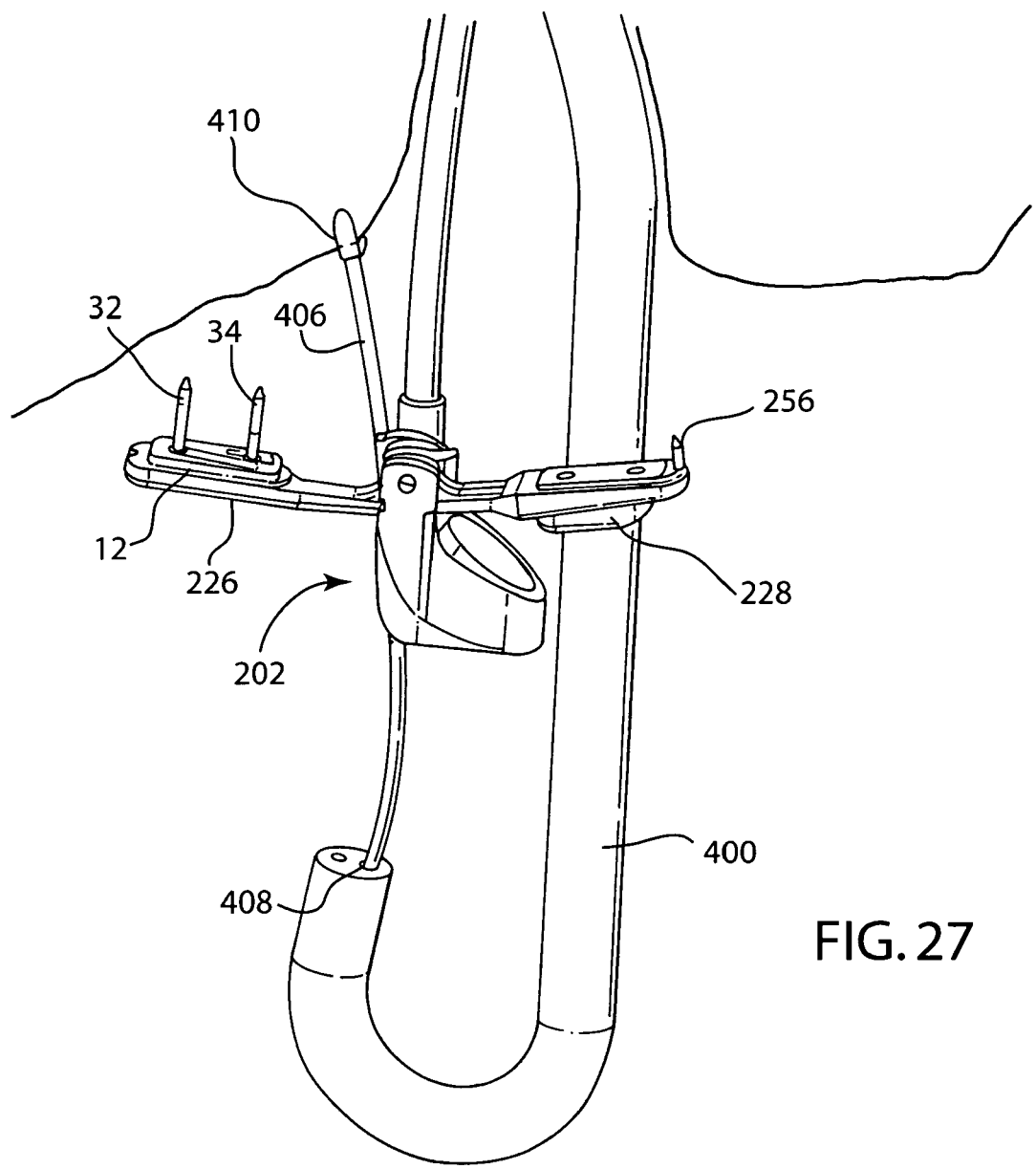
FIG. 27 is a view similar to FIG. 26, and additionally shows a grasping instrument advanced through the endoscope and engaging the target tissue at which a plication is desired to be made.
Figure 28:
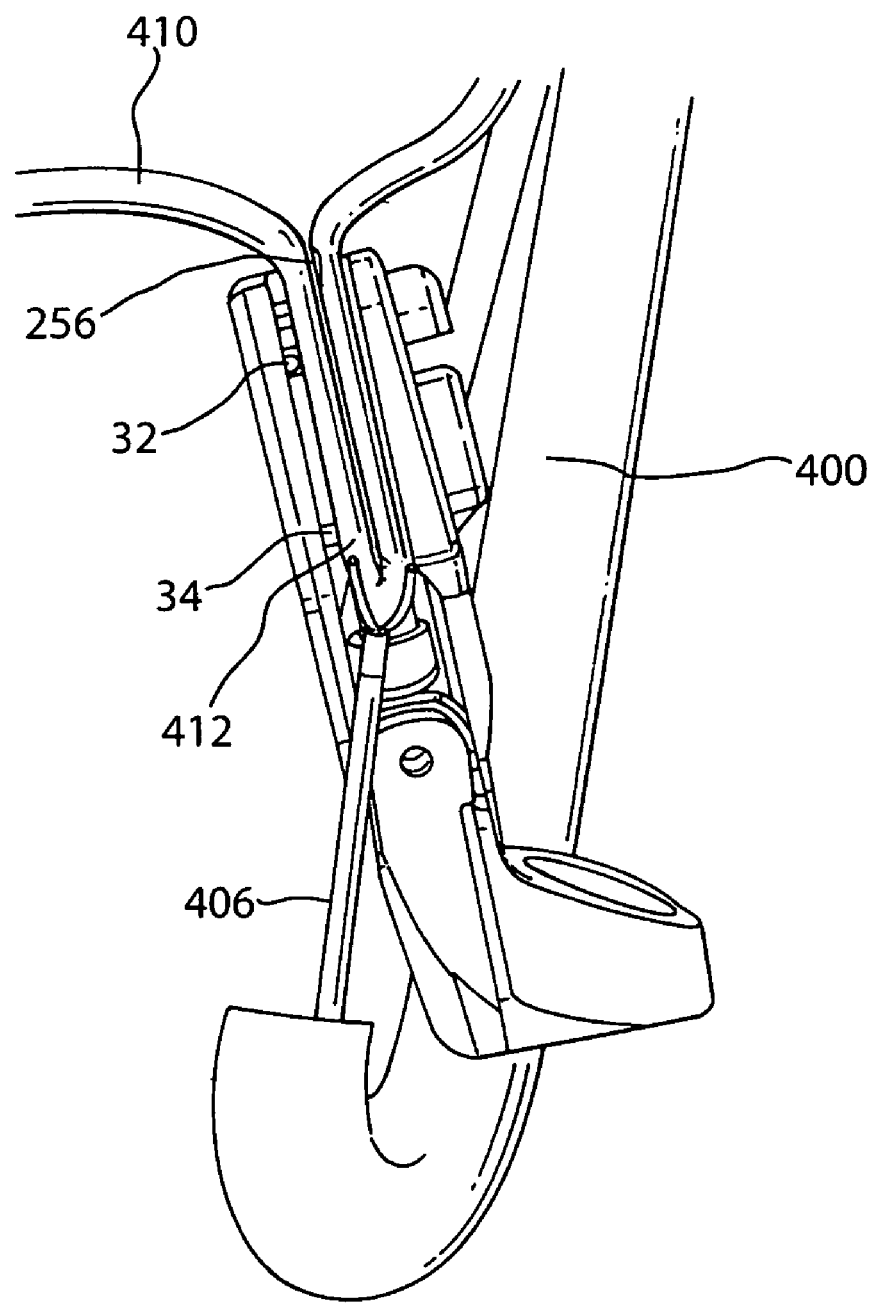
FIG. 28 illustrates the jaws of the instrument plicating the target tissue and the fastener in a locked configuration.

Referring to FIG. 27, a tissue grasping instrument 406, e.g., a forceps, helical needle, or tagging device, is preferably then inserted through a working channel 408 of the endoscope 400 and directed at target tissue 410 one to three centimeters into the stomach adjacent the LES where the center of a plication is to be located. The grasping instrument 406 engages the tissue 410 and pulls the tissue back between the jaws 226, 228 of the end effector 202 of the instrument 200. In addition, the handle 204 and/or control shaft 206 of the instrument 200 are pulled back in gross (i.e., in the direction of withdrawing the instrument) such that the jaws approach the tissue 410 in a direction substantially parallel to the esophagus. This is a highly desirable angle of approach that has been previously unattainable with endoscopic GERD treatment instruments. That is, any device that retroflexes must extend through an arc. It is not possible for a retroflexed device to be both parallel to an entry path and also displaced a couple of centimeters away from the entry path.

The proximal actuation handle 204 is then operated to cause the jaws 226, 228 to close. As a central point of the tissue 410 is held in a fixed location between the jaws by the grasping instrument 406 during movement of the jaws, a tissue plication 412 if formed by the jaws and the male and female parts 12, 14 of the fastener 10 are brought together with the plication 412 clamped therebetween. When the jaws 226, 228 are closed about the tissue plication 412, the posts 32, 34 of the male part 12 of the fastener 10 preferably pierce the tissue down to the serosa, and the piercing post 256 of the female jaw 228 preferably pierces through the deep muscle of the tissue and sufficiently to damage the tissue to cause serosa to serosa contact. Experimental procedures have shown that this contact results in tissue adhesion after healing, such that the tissue is permanently reconfigured; i.e., even if the fastener 10 is later removed. In this manner, a zone of reduced compliance is created about the LES.

The location and size of the plication as well as the relative positions of the fastener parts are observed via the scope. Moreover, more or less clamping pressure can be applied to the plicated tissue by control of the proximal actuation handle 204.

Figure 29:
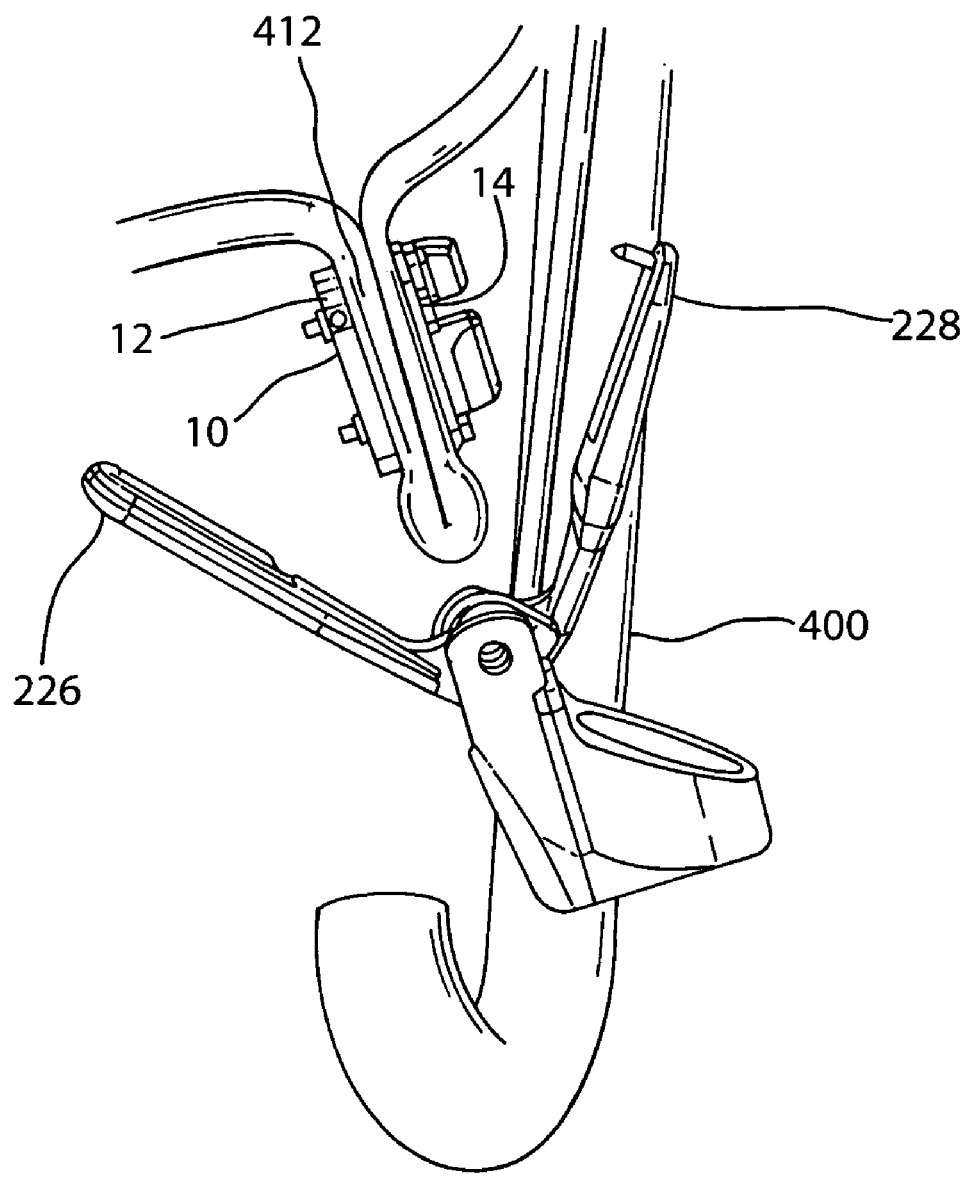
FIG. 29 illustrates the jaws of the instrument in an open position and the fastener holding the plicated tissue together.

Referring to FIG. 29, if the plication 412 appears satisfactory, the proximal actuation handle 204 is then operated, as described above, to lock the male and female parts 12, 14 of the fastener 10 and release the coupled fastener from the jaws 226, 228. If the plication or fastener position is not satisfactory, prior to locking and release, the jaws can be opened, reoriented if necessary, and another plication can be formed.

After the fastener is applied, the jaws are then closed, the endoscope is straightened, and the end effector is preferably re-docked over the distal end of the endoscope. The instrument and endoscope are preferably together withdrawn through the esophagus and out of the patient. Alternatively, the endoscope may be withdrawn first, followed by the withdrawal of the instrument preferably under visualization.

As discussed above, if at any time the fastener or either of the parts thereof become loose during the implantation procedure or any time after the procedure, the sharps on the fastener elements are adapted to assume a safe configuration or are permanently covered. As such, the fastener or its parts may be safely passed through the gastrointestinal system of the patient.

Figure 30:
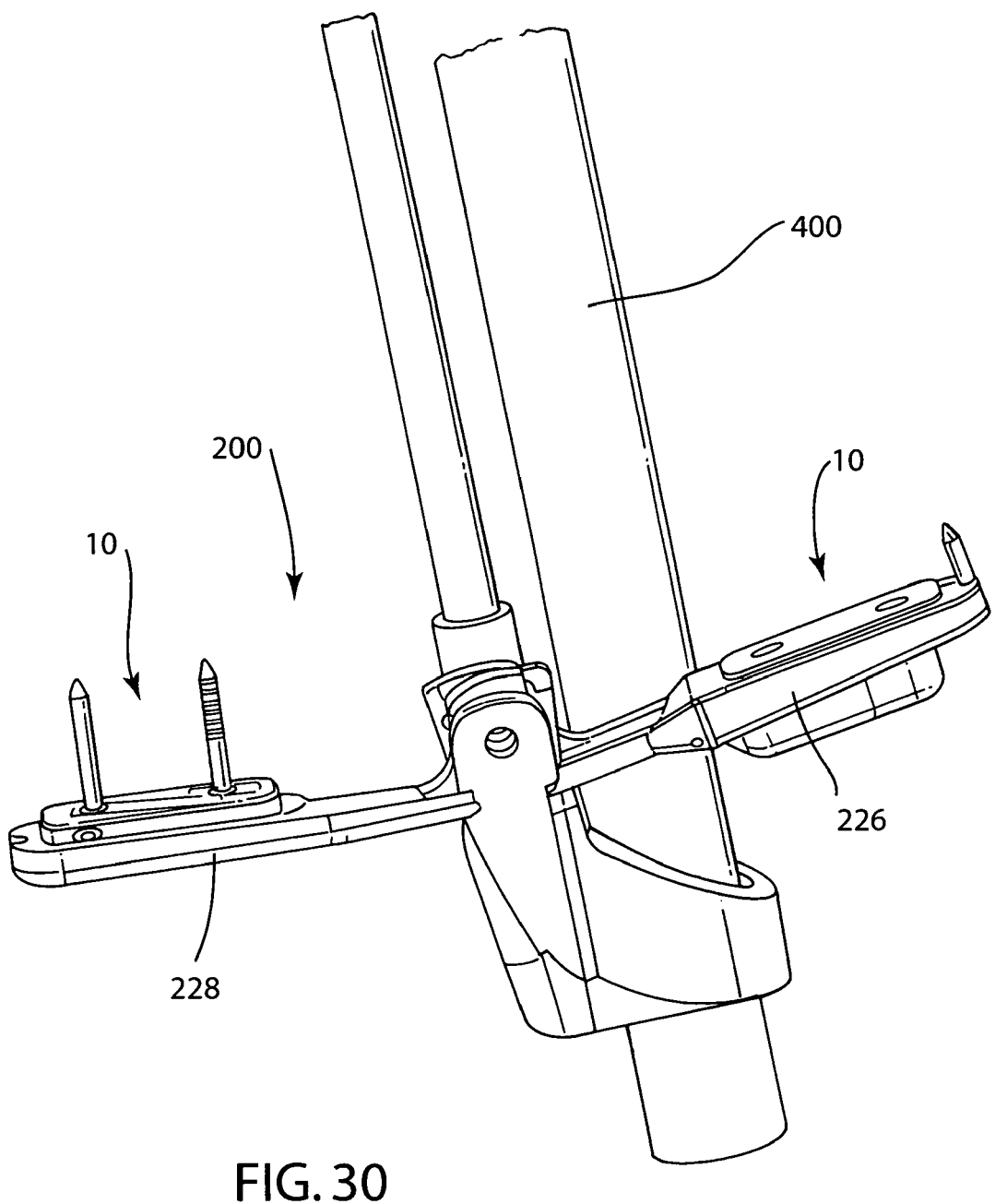
FIG. 30 illustrates an alternate embodiment of the procedure in which the end effector is operated while coupled to an endoscope.

While it is preferable to decouple the instrument from the endoscope during the procedure, it is appreciated that the instrument may be operated while coupled to the endoscope. That is, referring to FIG. 30, the target tissue is approached by opening the jaws 226, 228 and simply retracting the instrument 200 along the endoscope 400 until the tissue about the LES is contacted. The jaws 226, 228 are then closed and the fastener 10 applied, as described above. In order to utilize this procedure, the sleeve 320 of the instrument should be offset relative to the jaws 226, 228 so that the jaws can clear the endoscope when opening and closing.

Figure 31:
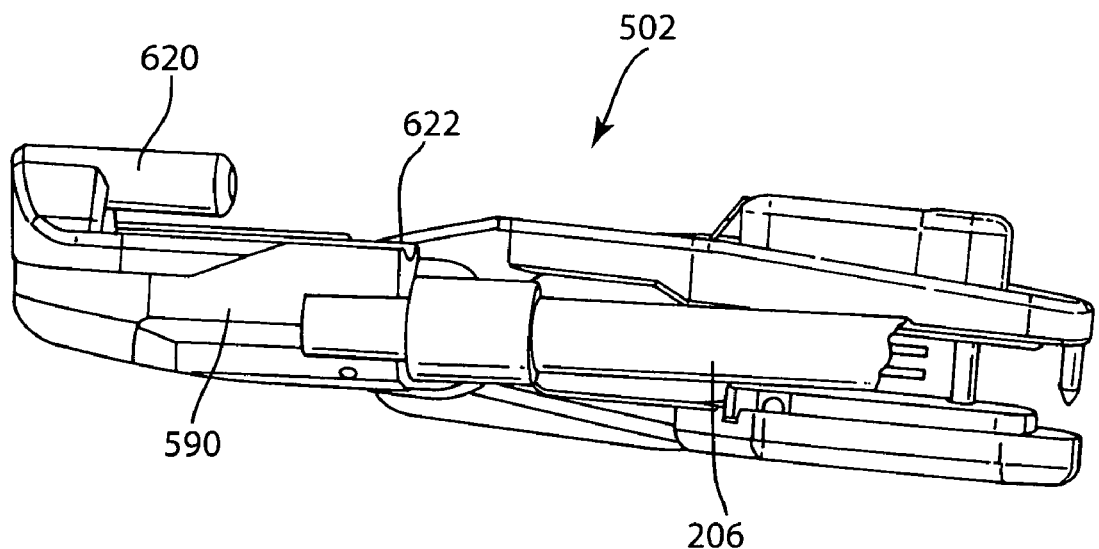
FIG. 31 is a side elevation of a second embodiment of the distal end effector adapted to be coupled in the distal opening of a working channel of an endoscope.
Figure 32:
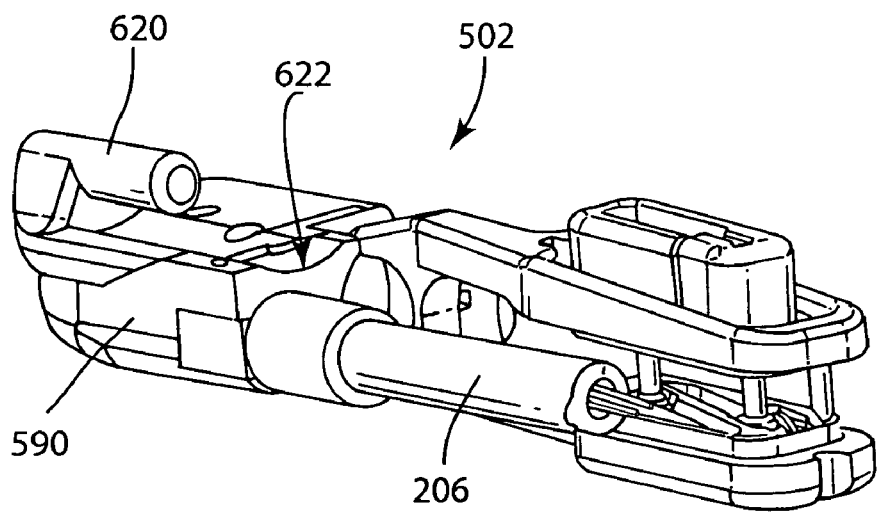
FIG. 32 is a perspective view of the second embodiment of the distal end effector shown in FIG. 31.

Turning now to FIGS. 31 and 32, a first alternative embodiment of a distal end effector 502 of the instrument 200 according to the invention is shown. The end effector 502 is adapted to couple within the distal end of a working channel of an endoscope, rather than be coupled about the endoscope with a sleeve. To that end, the housing 590 of the end effector 502 is provided with a proximally directed peg 620 preferably located above, but in line with the control shaft 206, and sized to be received within the distal end of a working channel of an endoscope. In addition, the housing 590 also includes a concave surface 622 permitting the housing 590 and endoscope to be adjacent in a minimized profile.

In use, the end effector is docked with the distal end of the endoscope using the peg 620, and the control shaft 206 is held taught relative to the endoscope to maintain the coupling. The cross-sectional area for the system at the end effector (end effector and endoscope coupled together) is approximately 150 mm$^2$. It is noted that the cross-sectional area of the system is smaller than the area defined by a system utilizing a sleeve, as the endoscope is close fitting with the end effector and the sleeve dimensions are eliminated. The endoscope, with end effector 502 attached at its distal end, is then inserted into the patient's stomach. The proximal handle 204 and/or control shaft 206 is then manipulated in gross to disengage the end effector. Thereafter, the procedure continues, preferably as discussed above, until plication and fastener application is achieved. Then, prior to removal of the instrument and endoscope, the end effector 502 is preferably re-docked with the endoscope, and the instrument and endoscope are withdrawn from the patient. Alternatively, the endoscope and instrument are separately removed.

Figure 33:
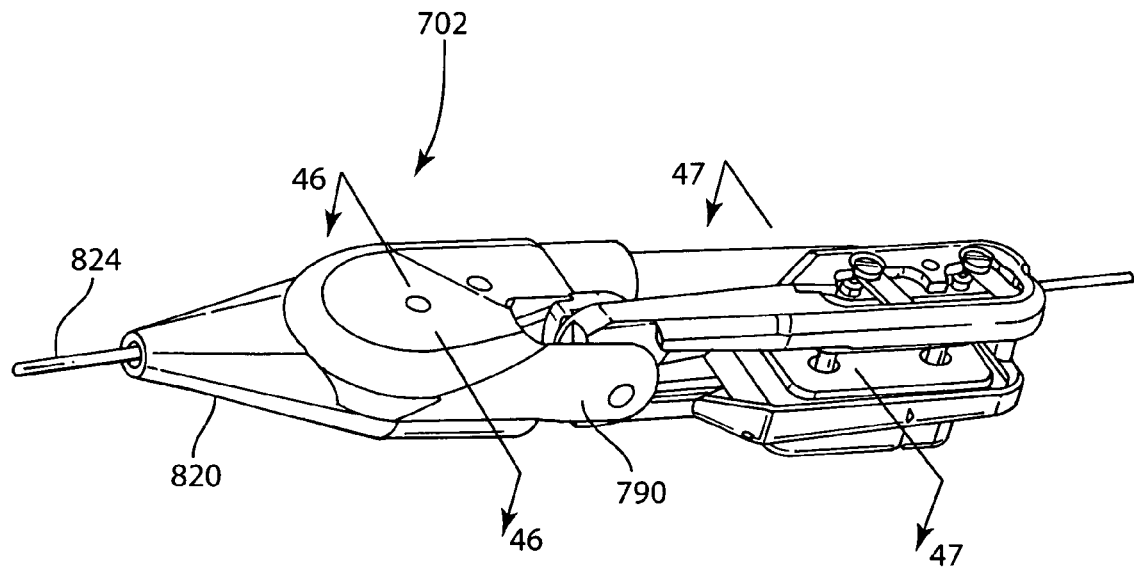
FIG. 33 is a side perspective view of a third embodiment of the distal end effector adapted to be advanced over a guidewire.
Figure 34:
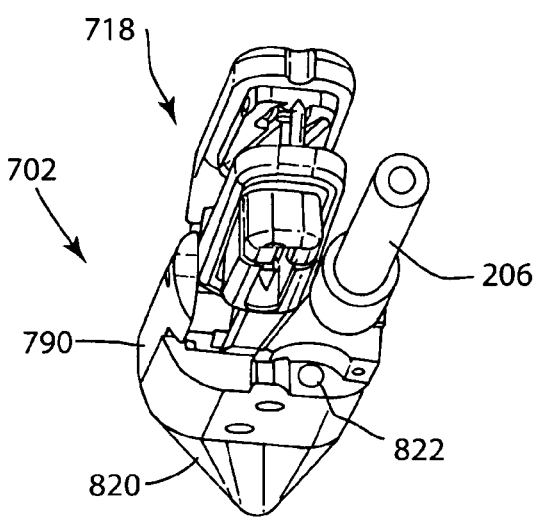
FIG. 34 rear perspective view of the third embodiment of the distal end effector shown in FIG. 33.

While the instrument has been shown adapted to be coupled to an endoscope, it is recognized that the instrument may be modified for use in a manner in which it is always decoupled from an endoscope. Referring now to FIGS. 33 and 34, a second alternate embodiment of the distal end effector 702 of the instrument 200 is shown. The housing 790 of the end effector 702 is provided with a tapered nose piece 820 defining a longitudinal passage 822 sized to receive a guidewire 824. The guidewire may have a diameter less than one millimeter. The nose piece 820 is preferably formed from a highly flexible material such as silicone.

Figure 35:
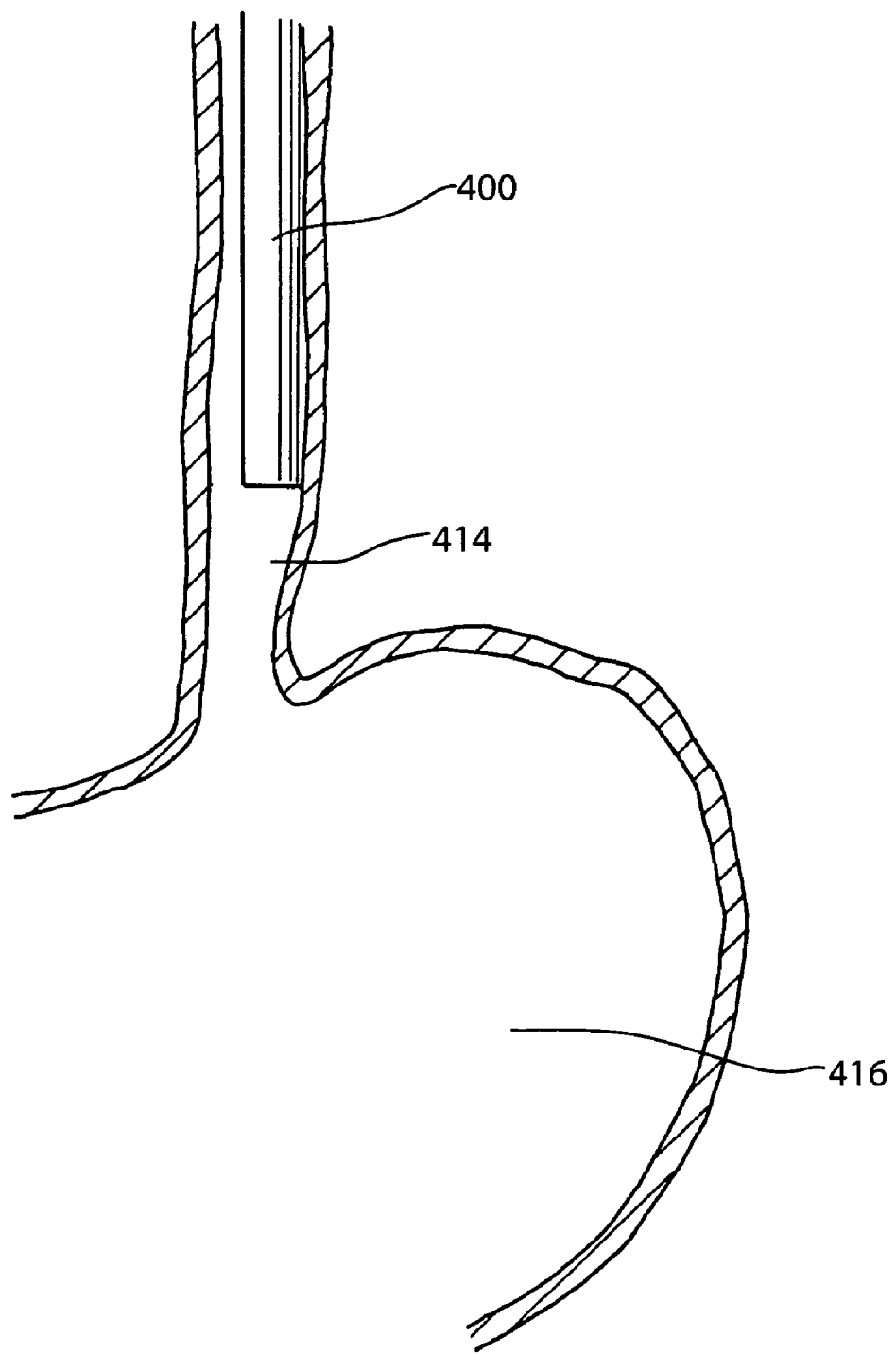
FIGS. 35 through 45 illustrate a second embodiment of the procedure in which the end effector is advanced over a guidewire into the stomach and operated under view of an endoscope.
Figure 36:
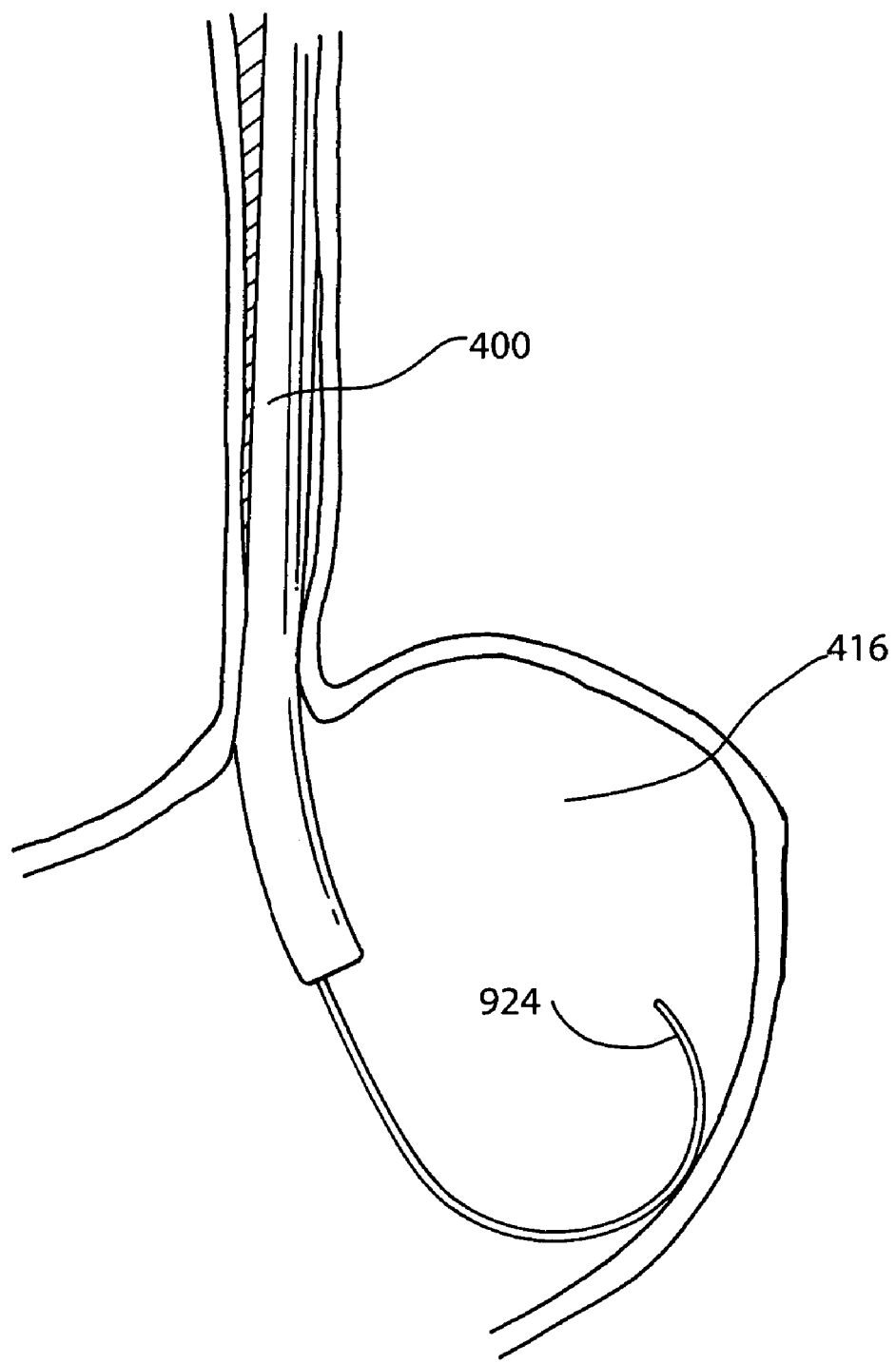
Figure 37:
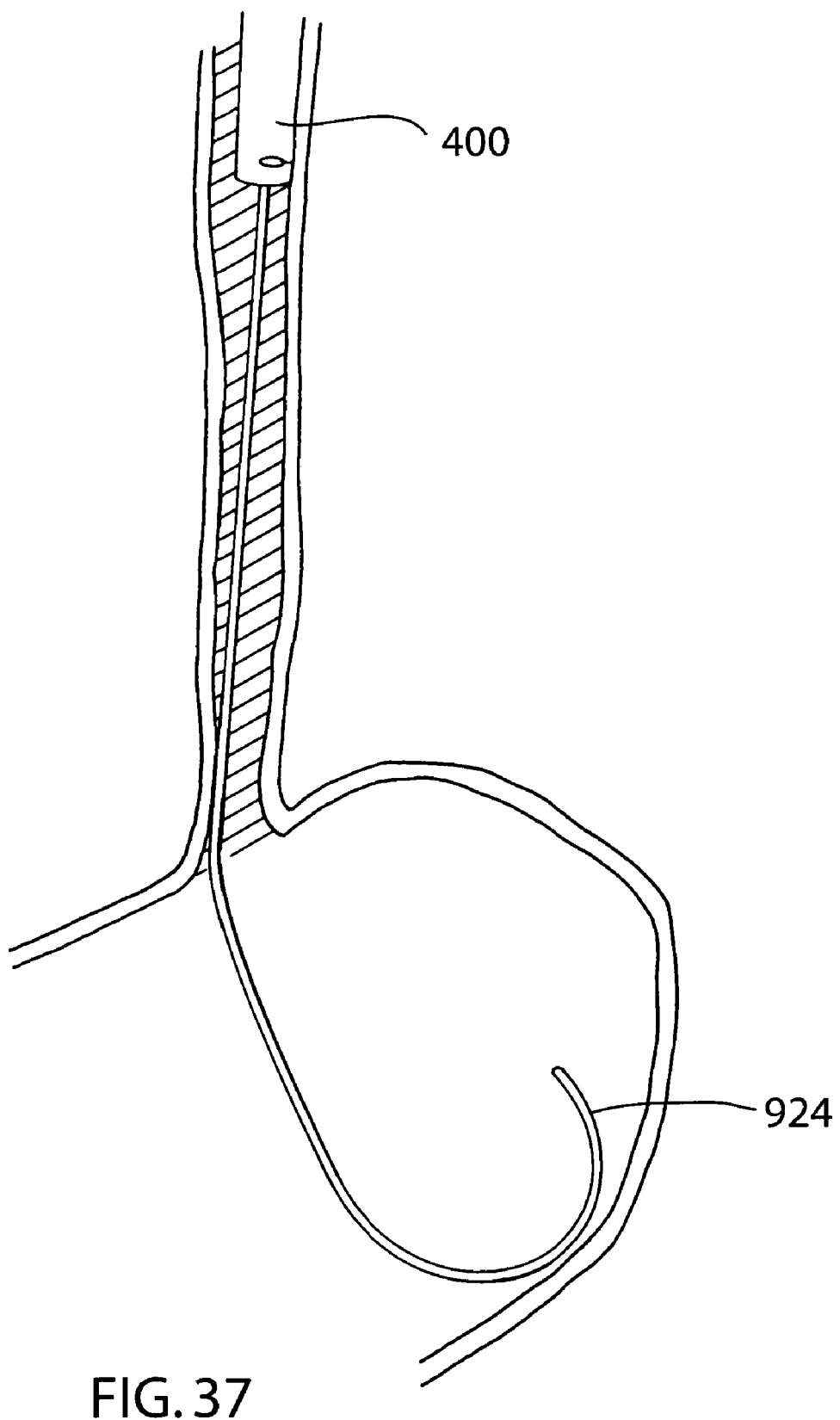
Figure 38:
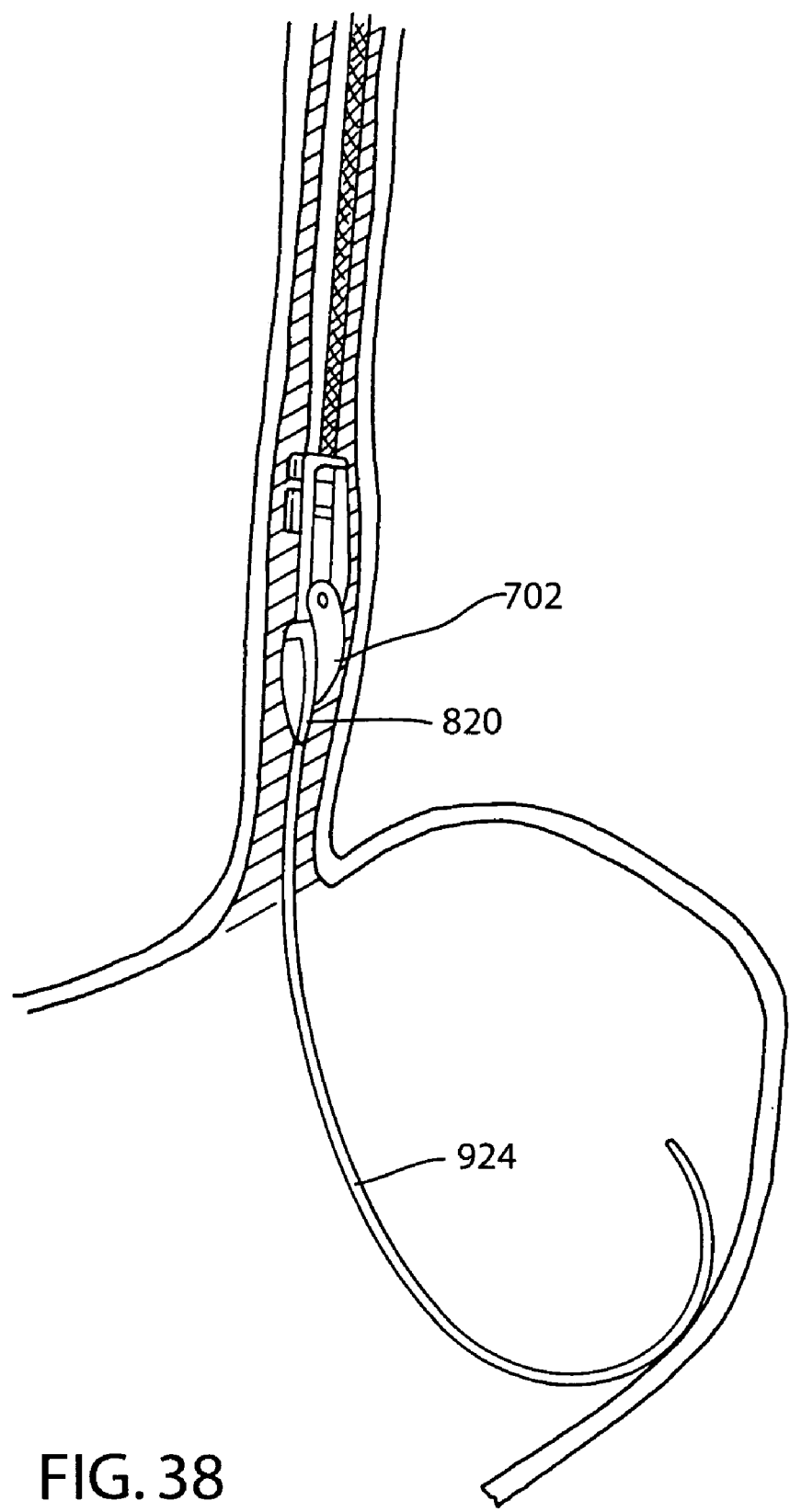
Figure 39:
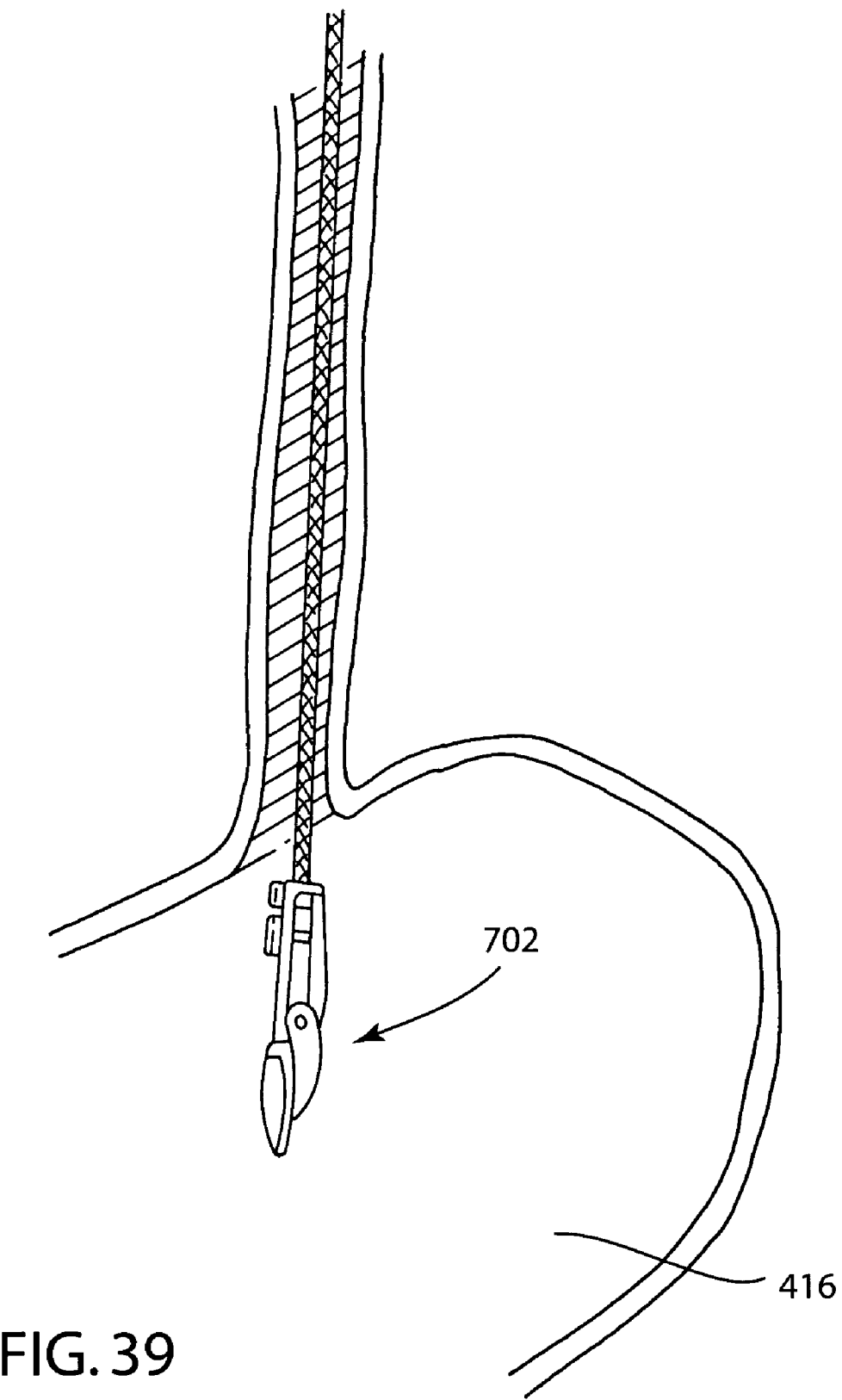
Figure 40:
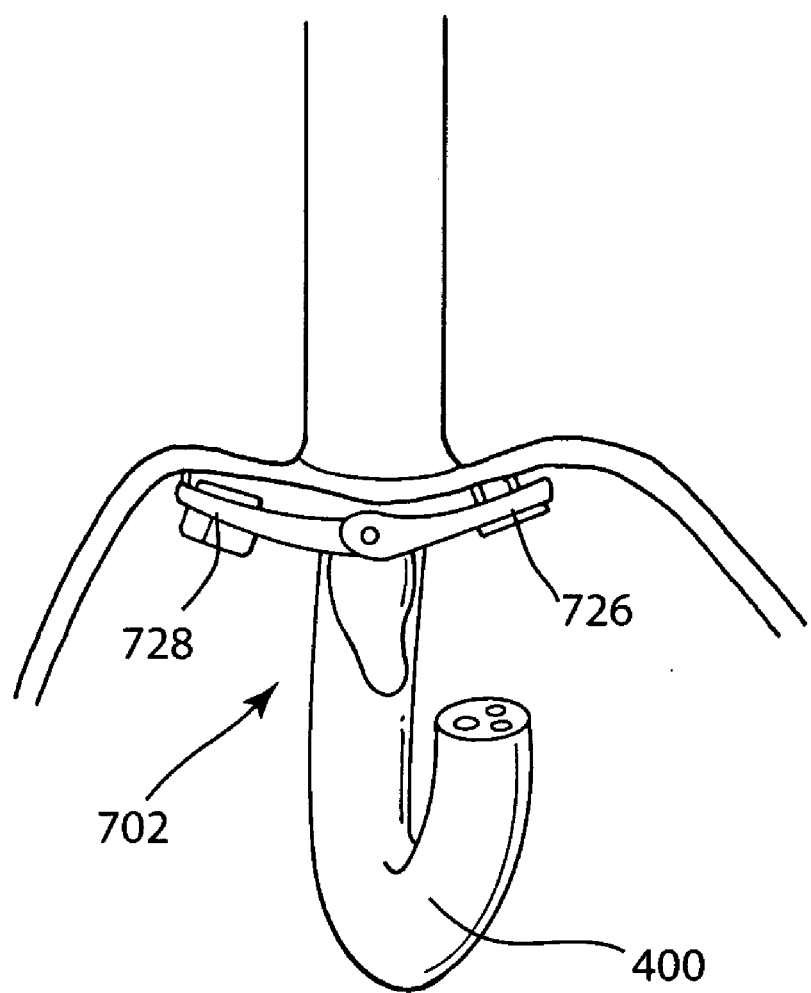
Figure 41:
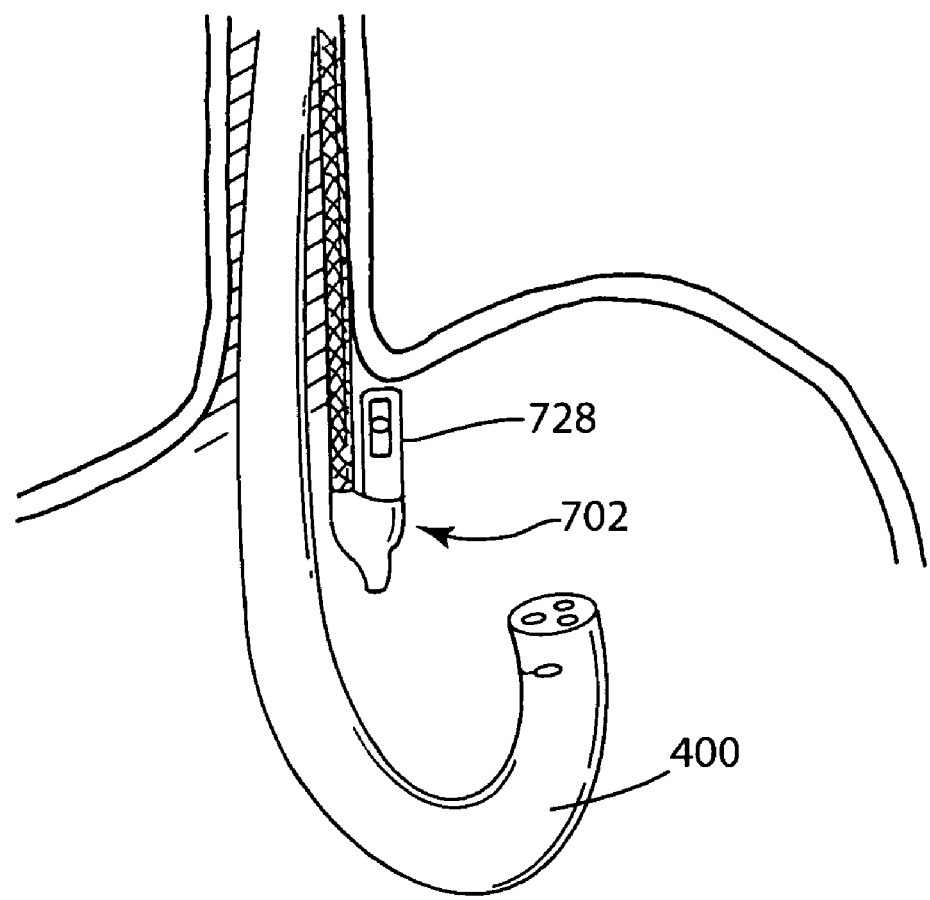
Figure 42:
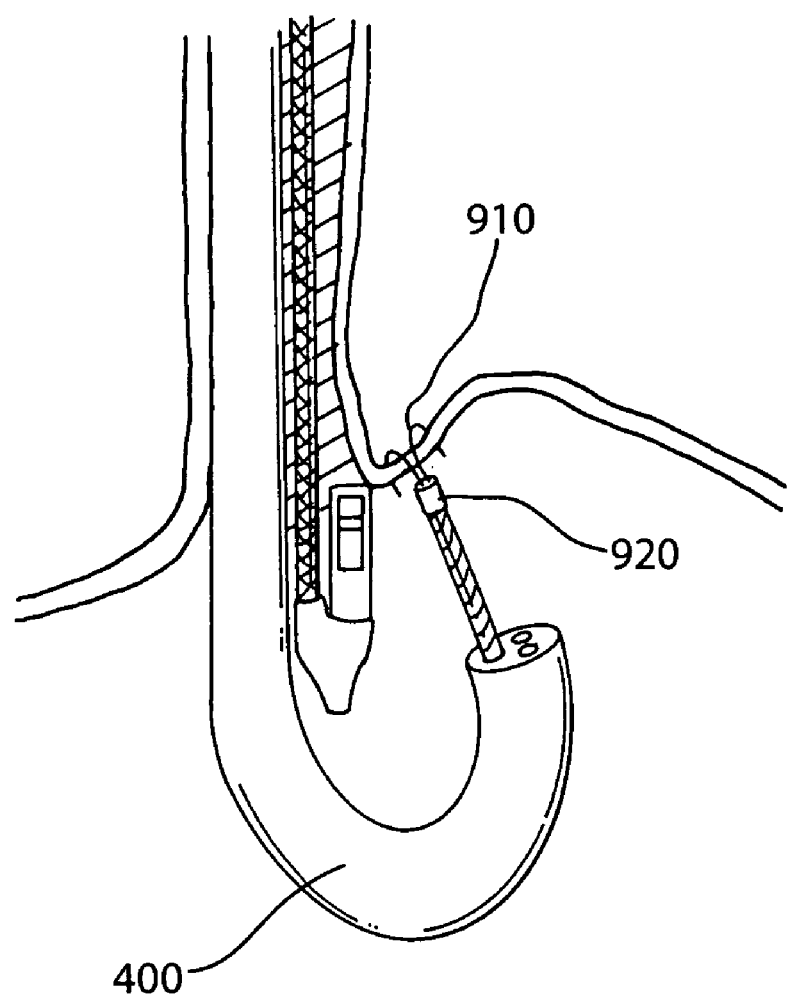
Figure 43:
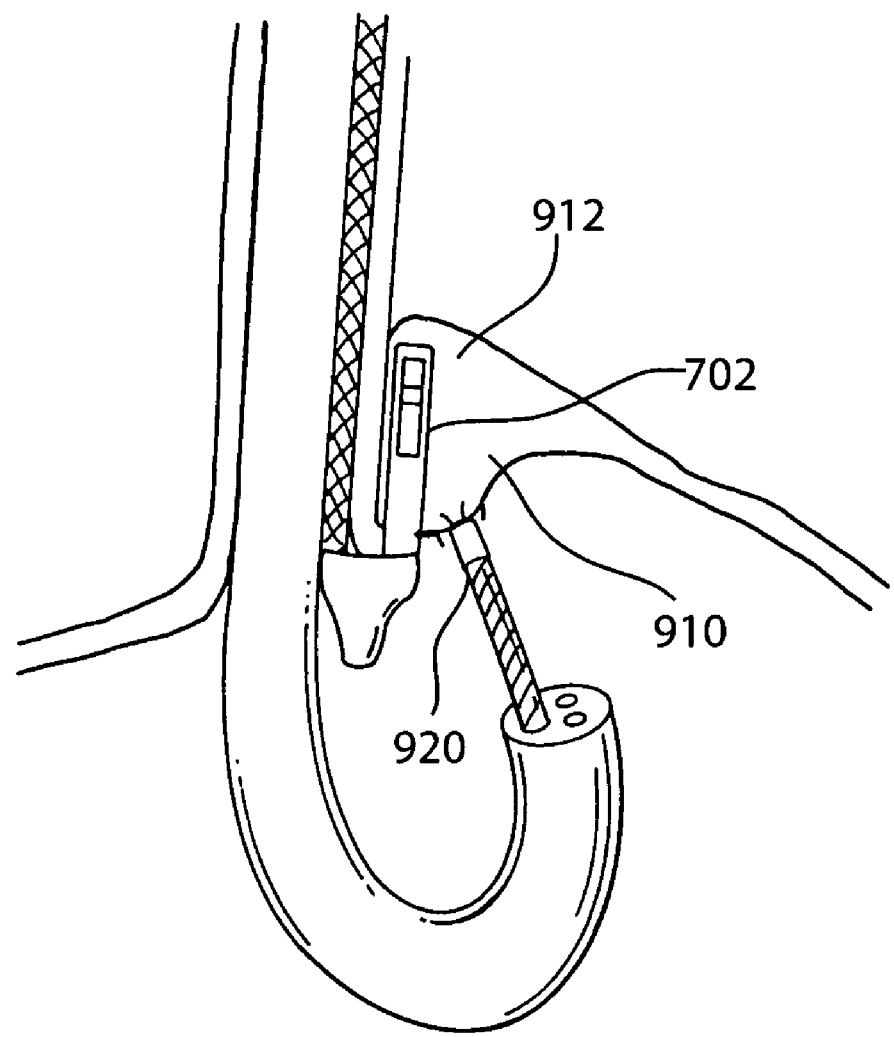
Figure 44:
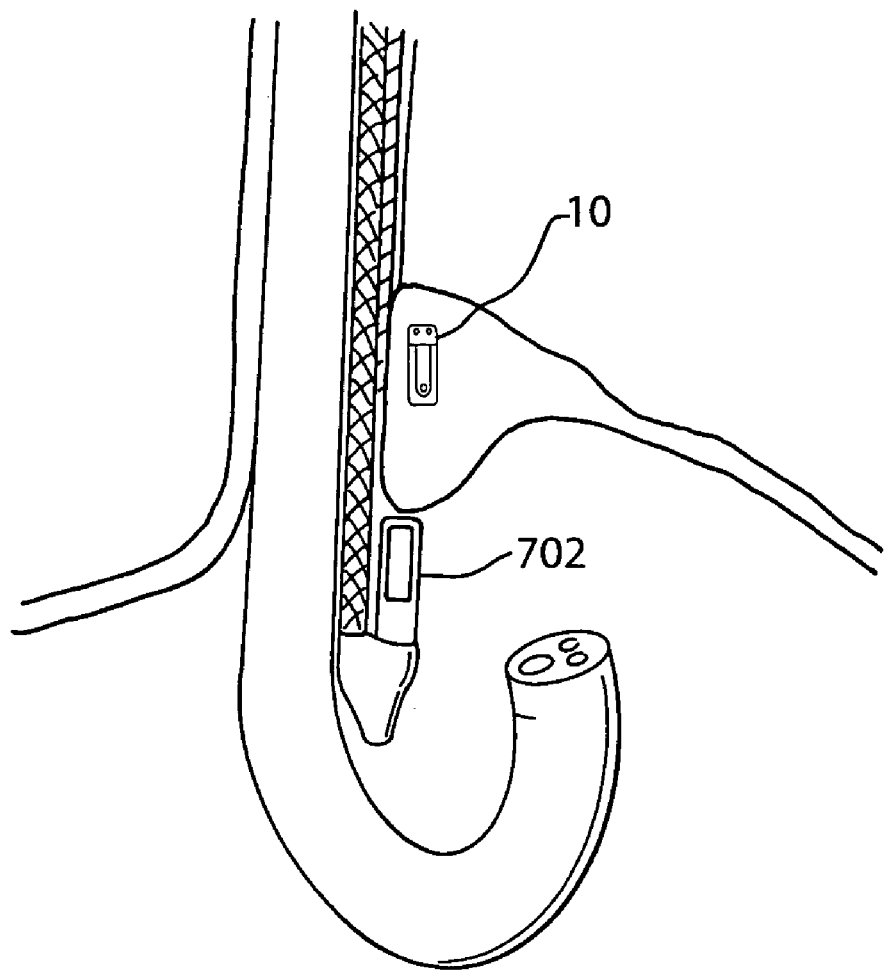
Figure 45:
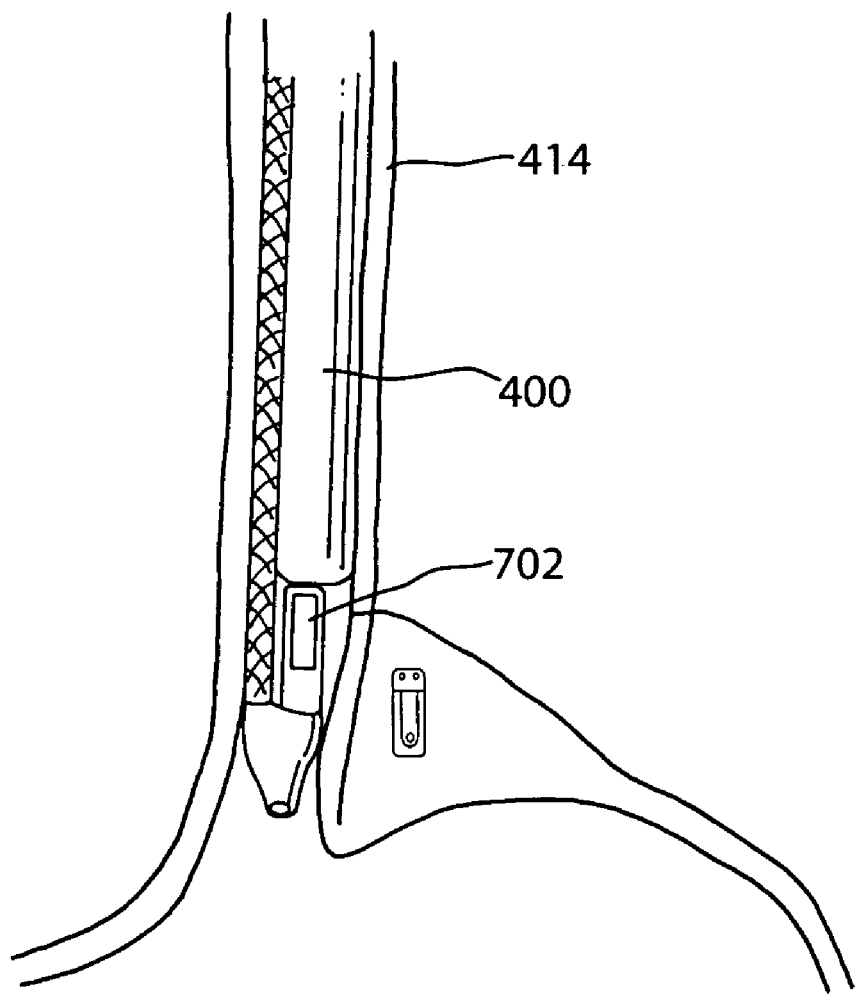

According to a preferred method of use, referring to FIG. 35, an endoscope 400 is preferably first inserted through the tracheopharangeal passage 414 and into the stomach 416 in accord with a well-known procedure. Next, referring to FIG. 36, a guidewire 924 is advanced through the endoscope into the stomach. Referring to FIG. 37, the endoscope 400 is then preferably withdrawn from over the guidewire 824. Referring to FIG. 38, the end effector 702 is then blindly advanced over the guidewire 924 and introduced into the stomach 416. The tapered nose piece 820 and relatively small head-on cross-sectional area of the system facilitate the introduction. Referring to FIG. 39, after the end effector 702 is located in the stomach 716, the guidewire 824 is preferably withdrawn from the stomach. Referring now to FIGS. 40 and 41, the endoscope is then reintroduced alongside the control shaft of the instrument, advanced into the stomach and retroflexed to view the end effector 702. The jaws 726, 728 of the end effector 702 are also opened and brought adjacent the tissue which is to be plicated. Referring to FIG. 42, a tissue grabbing device 920 is deployed through a working channel of the endoscope 400 and operated to engage tissue 910 at a location at which the fold of a plication is desired. The tissue grabbing device preferably includes piercers which extend through the mucosa and the muscularis (deep muscle) to thereby hold these layers together and prevent delamination. Turning to FIG. 43, the jaws of the end effector 702 are closed, forming a plication 812 about the engaged tissue 910, the plication 912 being substantially parallel to the esophagus. The plication extends from the location held by the device 920 to the end of the jaws of the instrument. Referring to FIG. 44, the fastener 10 is deployed and the jaws of the end effector 702 are opened. Referring to FIG. 45, the jaws of the end effector 702 are closed, and the end effector 702 is withdrawn through the esophagus 414 under visualization of the endoscope 400. That is, the closed jaws of the end effector 702 are preferably positioned directly distal of the endoscope 400 to minimize the cross-sectional area of the endoscope/instrument system as well as to permit constant visualization of the end effector during the retraction of the end effector through the esophagus.

Figure 46:
FIG. 46 is an end view schematic illustration of a cross-sectional area across line 46—46 in FIG. 33.
Figure 47:
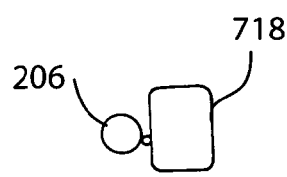
FIG. 47 is an end view schematic illustration of a cross-sectional area across line 46—46 in FIG. 33.

It is noted that this embodiment provides the smallest cross-sectional area for the system in the esophagus, as the area is limited to either (1) the end effector, or (2) the endoscope and control shaft, but never both (1) and (2) at the same time. Referring to FIG. 46, for (1), the end effector cross-sectional area across the clevis 790 distal of the jaw assembly is approximately 75 mm$^2$. Also for (1), the end effector cross-sectional area proximal of the clevis and across the jaw assembly 718 is (with the jaw assembly in a closed position) is approximately 115 mm$^2$ (calculated as the approximately 102 mm$^2$ cross-sectional area of the jaw assembly 718 plus the 12.6 mm$^2$ cross-sectional area of a 4 mm control shaft). For (2), the combined cross-sectional area of the endoscope and control shaft is 76.2 mm$^2$, calculated as 63.6 mm$^2$ for a 9 mm endoscope and 12.6 mm$^2$ for a 4 mm control shaft.

There have been described and illustrated herein several embodiments of fasteners, instruments, systems, and methods for the endoluminal treatment of gastroesophageal reflux disease (GERD). While particular embodiments of the invention have been described, it is not intended that the invention be limited thereto, as it is intended that the invention be as broad in scope as the art will allow and that the specification be read likewise. For example, while particular preferred dimensions have been provided for both elements of the instrument and fastener, as well as cross-sectional areas of the system, it is appreciated that the system and its elements may have different relative sizes. For example, the cross-sectional areas can be decreased further if a pediatric endoscope (4 to 6 mm) is used. Also, while a "looking back" instrument has been disclosed particularly for fastener application designed to treat GERD, it is appreciated that a "forward looking" straight instrument with similar jaw assembly can be used to apply the fastener for treatments of other conditions, e.g., obesity, ulceration, stomach cancer, implantation of pH measurement or monitoring devices, feeding tubes, etc. Moreover, a straight device can be smaller in diameter and be operated through a working channel of an endoscope. It will therefore be appreciated by those skilled in the art that yet other modifications could be made to the provided invention without deviating from its spirit and scope as so claimed.

What is claimed is:

1. A surgical instrument, comprising:
   a) a tubular control shaft having proximal and distal ends and defining a longitudinal axis;
   b) a first control element extending through said control shaft and having proximal and distal ends;
   c) a proximal handle including a stationary portion and a first movable portion movable relative to said stationary portion, one of said stationary portion and said first movable portion coupled to said proximal end of said control shaft and the other of said stationary portion and said first movable portion coupled to said proximal end of said first control element, wherein actuation of said handle moves said first movable portion relative to said stationary portion and thereby causes said control shaft and said first control element to be longitudinally moved relative to each other; and d) a distal end effector coupled to said distal end of said control shaft and said first control element, said end effector including a clevis and first and second jaws mutually rotatable on said clevis between open and closed positions, said first and second jaws having terminal ends and said first and second jaws substantially oriented so that said terminal ends configured to are proximally directed away from said distal end of said control shaft while said first and second jaws are introduced into a said first and second jaws being laterally displaced relative to said longitudinal axis of said control shaft, wherein actuation of said handle effects rotation of said first and second jaws between said open and closed positions.

2. A surgical instrument according to claim 1, wherein: said first and second jaws are fixed in said proximally directed orientation.

3. A surgical instrument according to claim 1, wherein: said control shaft and said first control element are flexible.

4. A surgical instrument according to claim 1, further comprising:
e) a two-part fastener comprising first and second parts, wherein said first part is coupled to said first jaw, and said second part is coupled to said second jaw, said first and second parts are adapted to be locked together.

5. A surgical instrument according to claim 4, wherein: said first part of said fastener includes at least one tissue piercing post and said second jaw includes a tissue piercing post.

6. A surgical instrument according to claim 4, further comprising:
f) means for locking said first and second parts of said fastener together; and
g) means for releasing said locked fastener from said first and second jaws.

7. A surgical instrument according to claim 4, further comprising:
f) a second control element having proximal and distal ends,
wherein said control handle includes a second movable portion movable relative to said stationary member, said proximal end of said second control element being coupled to said second movable member and said distal end of said second control element extending to said distal end effector.

8. A surgical instrument according to claim 7, wherein: relative movement of said first control element and said control shaft in a first direction operates to move said jaws into a closed position, and
relative movement of said second control element and said control shaft in a second direction operates to reconfigure said first and second parts of said two-part fastener relative to each other such that said first and second parts are locked relative to each other.

9. A surgical instrument according to claim 8, wherein: relative movement of said second control element and said control shaft in a second direction is adapted to decouple the first and second parts of the fastener from said first and second jaws.

10. A surgical instrument according to claim 8, wherein: said second direction is opposite said first direction.

11. A surgical instrument according to claim 1, wherein: said first and second jaws include respective first and second tangs, and said end effector is provided with a mechanical assembly including a first bell crank having first and second sides, and at least one second control element,
said first side being coupled to said distal end of said first control element, and said at least one second control element extending between said second side and said first and second tangs,
wherein relative movement of said first control element and said shaft causes said first control element to apply a force in a first direction to said first bell crank that operates to rotate said first bell crank and apply a force in an opposite second direction to said at least one second control element such that said jaws are rotated.

12. A surgical instrument according to claim 1, further comprising:
e) a sleeve coupled to said end effector and adapted in size to be positioned over a portion of an endoscope.

13. A surgical instrument according to claim 12, wherein: said sleeve is adapted in size to be slidably positioned over a distal end of the endoscope.

14. A surgical instrument according to claim 1, further comprising:
e) a nose piece integrated with said end effector, said nose piece defining a longitudinal passage for a guidewire.

15. A surgical instrument according to claim 1, further comprising:
e) a connector coupled to said end effector and adapted to couple said end effector to an endoscope at a working channel of the endoscope.

16. A surgical instrument according to claim 1, wherein: said control shaft comprises a flat wound wire coil.

17. A surgical instrument for use in applying a fastener to tissue, the fastener including first and second parts lockable relative to each other, the first part having a structure adapted to enter an opening in the second part, said surgical instrument comprising:
a) a tubular control shaft having proximal and distal ends;
b) a first control element extending through said control shaft and having proximal and distal ends;
c) a second control element extending through said control shaft and having proximal and distal ends;
d) a proximal handle including a stationary portion and first and second movable portions movable relatative to said stationary portion, one of said stationary portion and said first movable portion being coupled to said proximal end of said control shaft, the other of said stationary portion and said first movable portion being coupled to said proximal end of said first control element, and said second movable portion being coupled to said proximal end of said second control element; and
e) a distal end effector assembly coupled to said distal ends of said control shaft and said first and second control elements, said end effector assembly including a clevis and first and second jaws mutually rotatable on said clevis between open and closed positions, said first jaw adapted to be coupled to the first part of the fastener, and said second jaw adapted to be coupled to the second part of the fastener,
wherein first actuation of said handle which moves said first movable portion relative to said stationary portion effects rotation of said first and second jaws between said open and closed positions, and
wherein when said first and second jaws are in said closed position, second actuation of said handle which moves said second movable portion relative to said stationary portion is adapted to lock the first and second parts of the fastener together.

18. A surgical instrument according to claim 17, wherein: said second actuation is adapted to decouple the first and second parts of the fastener from said first and second jaws.

19. A surgical instrument according to claim 17, wherein: said control shaft defines a longitudinal axis, and said first and second jaws are proximally directed and laterally displaced relative to said longitudinal axis of said control shaft.

20. A surgical instrument according to claim 17, wherein: said first and second jaws include respective first and second tangs, and
said end effector is provided with a mechanical assembly including a bell crank having first and second sides, and at least one third control element,
said first side being coupled to said distal end of said first control element, and said at least one third control element extending between said second side and said first and second tangs,
wherein relative movement of said first control element and said shaft causes said first control element to apply a force in a first direction to said first bell crank that operates to rotate said first bell crank and apply a force in an opposite second direction to said at least one third control element such that said jaws are rotated.

21. A surgical instrument according to claim 17, wherein: said first and second jaws are respectively provided with first and second release elements respectively movable relative to said first and second jaws,
said end effector includes a housing provided with a bell crank having first and second sides, said first side coupled to said distal end of said second control element and said second side decoupled from said first and second release elements,
wherein when said first and second jaws are in said closed position and second control element is moved distally relative to said control shaft, said second side of said bell crank contacts and moves said first and second release elements.

22. A surgical instrument according to claim 17, further comprising:
f) a sleeve coupled to said end effector and adapted in size to be positioned over an endoscope.

23. A surgical instrument according to claim 22, wherein: said sleeve is adapted in size to be slidably received over a distal end of the endoscope.

24. A surgical instrument according to claim 17, further comprising:
f) a nose piece integrated with said end effector, said nose piece defining a longitudinal passage for a guidewire.

25. A surgical instrument according to claim 17, further comprising:
f) a connector coupled to said end effector and adapted to couple said end effector to an endoscope at a working channel of the endoscope.

26. A surgical instrument according to claim 17, further comprising:
f) said fastener, wherein said first part of said fastener is coupled to said first jaw and said second part of said fastener is coupled to said second jaw, and wherein when said first and second jaws are in said closed position, said structure on said first part enters said opening in said second part.

27. A surgical instrument for use in applying a fastener to tissue, the fastener including first and second parts lockable relative to each other, said surgical instrument comprising:
a) an end effector including a shaft having a distal end first and second jaws, coupled to said distal end of said at least one of said jaws being movable relative to the other, said first jaw adapted to be coupled to the first part of the fastener and said second jaw adapted to be coupled to the second part of the fastener, said first and second jaws being continuously and movably directed towards a proximal end of said
b) first means for moving said first and second jaws relative to each other; and
c) second means for reconfiguring the first and second parts of the fastener relative to each other, wherein said first and second means are distinct from each other.

28. A surgical instrument, comprising:
a) an end effector including first and second jaws, configured to be proximally directed while said first and second jaws are introduced into a body at least one of said jaws being movable relative to the other, said end effector defining a greatest cross-sectional area;
b) a proximal handle; and
c) an elongate flexible tubular member extending between said end effector and said handle and defining a greatest outer area of said instrument between said end effector and said handle, said greatest outer area defining a second cross-sectional area,
wherein said second cross-sectional area is at least ten percent smaller than said greatest cross-sectional area of said end effector.

29. A surgical instrument according to claim 28, wherein: said second cross-sectional area is less than one half said greatest cross-sectional area.

30. A surgical instrument according to claim 28, wherein: said second cross-sectional area is less than one tenth said greatest cross-sectional area.

31. A surgical instrument according to claim 28, wherein: said instrument is for use with a tissue fastener having first and second parts which are couplable together, and wherein said first and second jaws are adapted to be coupled to said first and second parts, respectively and apply a clamping force to tissue located between said first and second parts.

32. A surgical instrument according to claim 28, wherein: said tubular member defines a longitudinal axis, and said first and second jaws are proximally directed and laterally displaced relative to said longitudinal axis.

33. A surgical instrument, comprising:
a) a tubular member having proximal and distal ends;
b) a control element having proximal and distal ends and extending through and longitudinally movable relative to said tubular member;
c) an end effector coupled to said distal ends of said tubular member and said control element, said end effector including first and second jaws provided with tangs, at least one of said jaws being movable relative to the other between open and closed positions,
wherein said jaws are urged into a closed position when said tangs are subject to a force in a first direction; and
d) means for applying a force in said first direction to said tangs when said control element is moved relative to said tubular member in a second direction opposite said first direction.

34. A surgical instrument according to claim 33, wherein said tubular member and said control element are flexible.

35. A surgical instrument according to claim 33, wherein:
said tubular member defines a longitudinal axis, and said first and second jaws are proximally directed and laterally displaced relative to said longitudinal axis of said tubular member.

36. A surgical instrument, comprising:
a) a flexible tubular control shaft having a proximal end, a distal end, and defining a longitudinal axis;
b) a distal end effector coupled to said distal end of said control shaft and including first and second jaws that are configured to be proximally directed and laterally displaced relative to said longitudinal axis while said first and second jaws are introduced into a said jaws having ends;
c) a shaft mount rotatably coupled to said distal end effector and fixed to said distal end of said control shaft;
d) a control element extending through said control shaft and having proximal and distal ends, said distal end coupled to said distal end effector; and
e) a handle means for moving said proximal end of said control element relative to said proximal end of said shaft,
wherein when said control element is moved relative to said control shaft to provide an amount of tension on said control element, said distal end effector rotates relative to said mount toward said longitudinal axis.

37. A surgical instrument according to claim 36, wherein:
when said control shaft and said control element are moved relative to each other to provide an amount of tension on said control element, said distal end effector rotates relative to said mount away from said longitudinal axis.

38. A surgical instrument according to claim 37, wherein:
said first and second jaws of said end effector assembly are fixed in a proximal facing direction.

39. A surgical instrument, comprising:
a) a flexible tubular control shaft having a proximal end, a distal end, and a length of at least 30 cm;
b) a distal end effector coupled to said distal end of said control shaft including first and second jaws continuously and directed towards said proximal end of said shaft, said end effector being substantially larger in diameter than said control shaft;
c) a control element extending through said control shaft and having proximal and distal ends, said distal end coupled to said distal end effector; and
d) a handle means for moving said proximal end of said control element relative to said proximal end of said shaft, said proximal end of said control element being rotationally fixed relative to said handle means,
wherein rotation of said handle means provides sufficient torque along a length of said instrument to rotate said distal end effector in a substantially 1:1 ratio relative to said rotation of said handle means.

40. A surgical instrument according to claim 39, wherein:
said control element is a stainless steel wire having a diameter between approximately 0.020 inch and 0.062 inch.

41. A surgical instrument according to claim 40, wherein:
said control element has a diameter of approximately 0.035 inch.

42. A surgical instrument, comprising:
an end effector including first and second jaws configured to be proximally directed while said first and second jaws are introduced into a, at least one of said jaws being movable relative to the other,
said end effector defining a greatest cross-sectional area;
a proximal handle; and
an elongate, flexible, tubular member extending between said end effector and said handle and defining an outer area of said instrument between said end effector and said handle, said outer area being at least ten percent smaller than said greatest cross-sectional area of said end effector.

43. A surgical instrument, comprising:
a flexible, tubular control shaft having a proximal end, a distal end, and a length of at least 25 cm;
a distal end effector coupled to said distal end of said control shaft including first and second jaws directed towards said proximal end of said shaft, said end effector being larger in diameter than said control shaft;
a control element extending through said control shaft and having proximal and distal ends, said distal end coupled to said distal end effector;
an actuator for moving said proximal end of said control element relative to said proximal end of said shaft, said proximal end of said control element being rotationally fixed relative to said actuator; and
upon rotation of said actuator, said actuator providing sufficient torque along a length of the instrument to rotate said distal end effector in a substantially 1:1 ratio relative to said rotation of said actuator.

* * * * *